US011459370B2

(12) United States Patent
Arnett et al.

(10) Patent No.: US 11,459,370 B2
(45) Date of Patent: Oct. 4, 2022

(54) BTNL3 PROTEINS, NUCLEIC ACIDS AND ANTIBODIES AND USES THEREOF

(71) Applicant: Amgen Inc., Thousand Oaks, CA (US)

(72) Inventors: Heather Arnett, Seattle, WA (US); Sabine Schadow Escobar, Sammamish, WA (US); Ryan Michael Swanson, Seattle, WA (US); Joanne Louise Viney, Belmont, MA (US)

(73) Assignee: Amgen Inc., Thousand Oaks, CA (US)

( * ) Notice: Subject to any disclaimer, the term of this patent is extended or adjusted under 35 U.S.C. 154(b) by 195 days.

(21) Appl. No.: 16/256,951

(22) Filed: Jan. 24, 2019

(65) Prior Publication Data
US 2019/0169259 A1 Jun. 6, 2019

Related U.S. Application Data

(62) Division of application No. 14/407,904, filed as application No. PCT/US2013/051097 on Jul. 18, 2013, now abandoned.

(60) Provisional application No. 61/673,639, filed on Jul. 19, 2012.

(51) Int. Cl.
C07K 14/705 (2006.01)
C07K 16/46 (2006.01)
A61K 38/00 (2006.01)
A61K 39/00 (2006.01)
A61K 39/395 (2006.01)

(52) U.S. Cl.
CPC ........ C07K 14/705 (2013.01); A61K 39/0013 (2013.01); A61K 39/3955 (2013.01); C07K 14/70503 (2013.01); C07K 16/46 (2013.01); A61K 38/00 (2013.01); C07K 2319/30 (2013.01)

(58) Field of Classification Search
CPC .. C07K 14/705; C07K 216/46; C07K 319/30; A61K 38/00
USPC ............................................ 424/133.1, 174.1
See application file for complete search history.

(56) References Cited

U.S. PATENT DOCUMENTS

| 4,474,893 | A | 10/1984 | Reading |
| 4,751,180 | A | 6/1988 | Cousens et al. |
| 4,935,233 | A | 6/1990 | Bell et al. |
| 4,946,778 | A | 8/1990 | Ladner et al. |
| 4,965,195 | A | 10/1990 | Namen et al. |
| 4,968,607 | A | 11/1990 | Dower et al. |
| 5,457,035 | A | 10/1995 | Baum et al. |
| 5,807,706 | A | 9/1998 | Carter et al. |
| 5,837,821 | A | 11/1998 | Wu |
| 6,060,285 | A | 5/2000 | Lenz et al. |
| 6,106,833 | A | 8/2000 | Ring et al. |
| 6,150,584 | A | 11/2000 | Kucherlapati et al. |
| 6,261,804 | B1 | 7/2001 | Szostak et al. |
| 6,699,473 | B2 | 3/2004 | Raisch et al. |
| 6,972,295 | B2 | 12/2005 | Hagmann et al. |
| 7,244,822 | B2 | 7/2007 | Baum et al. |
| 7,563,443 | B2 | 7/2009 | Grant et al. |
| 8,193,322 | B2 | 6/2012 | Yan et al. |
| 10,357,561 | B2 * | 7/2019 | Arnett .................. C07K 14/435 |
| 2015/0344554 | A1 * | 12/2015 | Arnett .............. C07K 14/70503 424/139.1 |

FOREIGN PATENT DOCUMENTS

| EP | 0 367 566 B1 | 5/1997 |
| EP | 0 460 846 B1 | 2/2002 |
| EP | 2 221 063 A1 | 8/2010 |
| WO | WO 1991/18982 A1 | 12/1991 |
| WO | WO 1993/10151 A1 | 5/1993 |
| WO | WO 1997/034631 A1 | 9/1997 |
| WO | WO 1999/31241 A1 | 6/1999 |
| WO | WO 2000/24782 A2 | 5/2000 |
| WO | WO 2000/32823 A1 | 6/2000 |
| WO | WO 2000/34784 A1 | 6/2000 |
| WO | WO2006/097327 A2 | 9/2006 |
| WO | WO 2008/016356 A2 | 2/2008 |
| WO | WO 2009/089004 A1 | 7/2009 |
| WO | WO 2011/127418 A1 | 10/2011 |

OTHER PUBLICATIONS

Advanced search—Protein—NCBI ((murine or mouse) and "BTNL3") p. 1; Nov. 4, 2021)).*
Manning et al (www.rndsystems.com/resources/posters/butyrophilin-and-butyrophilin-proteins-b7-related-modulators-t-cell-function; poster; p. 1; May 16, 2022).*
Abeler-Dörner et al., Butyrophilins: an emerging family of immune regulators, Trends in Immunology (2012), 33(1):34-41.
Adams et al., Generating Improved Single-Chain Fv Molecules for Tumor Targeting, *J. Immunol. Methods* (1999), 231:249-260.
Arnett et al., Cosignaling Complexity Gets More Convoluted: the Emerging Importance of the B7-Like Butyrophilin Family of Immune Regulators, *Current Immunology Reviews* (2008), 4:43-52.
Arnett et al., Regulation of Costimulation in the Era of Butyrophilins, *Cytokine* (2009), 46:370-375.
Ashkenazi et al., Protection Against Endotoxic Shock by a Tumor Necrosis Factor Receptor Immunoadhesin, Proc. Natl. Acad. Sci USA (1991), 88:10535-10539.
Baum et al., Molecular Characterization of Murine and Human OX40/OX40 Ligand Systems: Identification of a Human OX40 Ligand as the HTLV-1-Regulated Protein gp34, *EMBO J.* (1994), 13(17):3992-4001.
Bird et al., Single-Chain Antigen-Binding Proteins, *Science* (1988), 242:423-426.
Bork et al., The Immunoglobulin Fold-Structural Classification, Sequence Patterns and Common Core, *J. Mol. Biol.* (1994), 242:309-320.

(Continued)

Primary Examiner — Lynn A Bristol
(74) Attorney, Agent, or Firm — Henry P. Wu

(57) ABSTRACT

The invention provides novel BTNL3 proteins, including multimers, fragments, fusion proteins, and variants. In addition, antibodies that can bind to BTNL3 proteins and nucleic acids encoding BTNL3 proteins are provided. Methods of making BTNL3 proteins using such nucleic acids are also provided. Uses for BTNL3 proteins, and agonists or antagonists thereof, are described.

1 Claim, 6 Drawing Sheets

Specification includes a Sequence Listing.

(56) References Cited

OTHER PUBLICATIONS

Bosher et al., RNA Interference: Genetic Wand and Genetic Watchdog, *Nature Cell Biol.* (2000), 2(2):E31-E36.
Boulianne et al., Production of Functional Chimaeric Mouse/Human Antibody, *Nature* (1984), 312:643-646.
Brake, Secretion of Heterologous Proteins Directed by the Yeast Alpha-Factor Leader, *Biotechnology* (1989), 13:269-280.
Brewer et al., Engineering Proteins to Enable Their Isolation in a Biologically Active Form, *Purification and Analysis of Recombinant Proteins* (1991), 11:239-266.
Byrn et al., Biological Properties of a CD4 Immunoadhesin, *Nature* (1990), 344:667-670.
Cole et al., The EBV-Hybridoma Technique and its Application to Human Lung Cancer, *Monoclonal Anitbodies and Cancer Therapy*, Alan R. Liss, Inc. (1985), 77-96.
Cosman et al, Cloning, Sequence and Expression of Human Interleukin-2 Receptor, *Nature* (1984), 312(5996):768-771.
Cosman et al., High Level Stable Expression of Human Interleukin-2 Receptors in Mouse Cells Generates Only Low Affinity Interleukin-2 Binding Sites, *Mol. Immunol.* (1986), 23:935-941.
Cosman et al., ULBPs, Novel MHC Class I-Related Molecules, Bind to CMV Glycoprotein UL16 and Stimulate NK Cytotoxicity Through the NKG2D Receptor, *Immunity* (2001), 14:123-133.
Desmyter et al., Antigen Specificity and High Affinity Binding Provided by One Single Loop of a Camel Single-Domain Antibody, *J. Biol. Chem.* (2001), 276:26285-26290.
Devereux et al., A Comprehensive Set of Sequence Analysis Programs for the VAX, *Nucleic Acids Res.* (1984), 12(Part 1):387-395.
Elmark et al., In Vitro Molecular Evolution of Antibody Genes Mimicking Receptor Revision, *Mol. Immunol.* (2002), 39(5-6):349.
Fisher et al., The Pattern of Protein Synthesis in SV40-Infected CV-1 Cells, *Int. J. Cancer* (1970), 5:21-27.
Fjose et al., RNA Interference: Mechanisms and Applications, *Biotechnol. Ann. Rev.* (2001), 7:31-57.
Gambari, Peptide-Nucleic Acids (PNAs) : a Tool for the Development of Gene Expression Modifiers, *Curr. Pharm. Des.* (2001), 7(17):1839-1862.
Gilliland et al., Rapid and Reliable Cloning of Antibody Variable Regions and Generation of Recombinant Single Chain Antibody Fragments, *Tissue Antigens* (1996) 47:1-20.
Gluzman et al., SV-40-Transformed Simian Cells Support the Replication of Early SV40 Mutants, *Cell* (1981), 23(1):175-182.
Gribskov et al., Sigma Factors from *E. coli*, B. Subtilis, Phage SP01, and Phage T4 are Homologous Proteins, *Nucleic Acids Res.* (1986), 14:6745.
Guggenmos et al., Sustained Il-12 Signaling is Required for Th1 Development, *J. Immunol.* (2004), 172 :61-68.
Hanes et al., In vitro Selection and Evolution of Functional Proteins by Using Ribosome Display, *Proc. Natl. Acad. Sci.* (1997), 94:4937-4942.
Harel-Bellan et al., Specific Inhibition of C-Myc Protein Biosynthesis Using an Antisense Deoxy-Oligonucleotide in Human T Lymphocytes,, *J. Immunol.* (1988), 140(7):2431-2435.
Harel-Bellan et al., Specific Inhibition of Lymphokine Biosynthesis and Autocrine Growth Using Antisense Oligonucleotides in Th1 and Th2 Helper T Cell Clones, *J. Exp. Med.* (1988), 168(6):2309-2318.
Harly, Key Implication of CD277/Butyrophilin-3 (BTN3A) in Cellular Stress Sensing by a Major Human T-Cell Subset, *Blood* (2012), 120(11):2269-2279.
Harpaz et al., Many of the Immunoglobulin Superfamily Domains in Cell Adhesion Molecules and Surface Receptors Belong to a New Structural Set Which is Close to that Containing Variable Domains, *J. Mol. Biol.* (1994), 238:528-539.
He et al., Antibody-Ribosome-mRNA (ARM) Complexes as Efficient Selection Particles for In Vitro Display and Evolution of Antibody Combining Sites, *Nucleic Acids. Res.* (1997), 25(24):5132-5134.
Henry et al., B30.2-like Domain Proteins: Update and New Insights into a Rapidly Expanding Family of Proteins, *Mol. Biol. Evol.* (1998), 15:1696-1705.
Hopp et al., A Short Polypeptide Marker Sequence Useful for Recombinant Protein Identification and Purification, *Bio/Technology* (1988), 6(10):1204.
Huls et al., Tumor Cell Killing by in Vitro Affinity-Matured Recombinant Human Monoclonal Antibodies, *Cancer Immunol. Immunother.* (2001), 50:163-171.
Hunkapiller et al., Diversity of the Immunoglobulin Gene Superfamily, *Adv. Immunol.* (1989), 44:1-63.
Huston et al., Protein Engineering of Antibody Binding Sites: Recovery of Specific Activity in an Anti-Digoxin Single-Chain Fv Analogue Produced in *Escherichia coli.*, *Proc. Natl. Acad. Sci. USA* (1988), 85:5879-5883.
Izant et al., Constitutive and Conditional Suppression of Exogenous and Endogenous Genes by Anti-Sense RNA, *Science* (1985), 229(4711):345-352.
Izant et al., Inhibition of Thymidine Kinase Gene Expression by Anti-Sense RNA: A Molecular Approach to Genetic Analysis, *Cell* (1984), 36(4):1007-1015.
Jackson et al., In Vitro Antibody Maturation. Improvement of a High Affinity, Neutralizing Antibody Against IL-1 Beta, *J. Immunol.* (1995), 154(7) :3310-3319.
Janeway et al., Antigen Recognition by B-Cell and T-Cell Receptors, *Immunobiology: The Immune System in Health Disease*, Fifth Edition, Part II, Chp. 3, Garland Publishing (2001), 93-122.
Jeong et al., PRY/SPRY/B30.2 Domain of Butyrophilin 1A1 (BTN1A1) Binds to Xanthine Oxidoreductase: Implications for the Function of BTN1A1 in the Mammary Gland and Other Tissues, *J. Biol. Chem.* (2009), 284:22444-22456.
Kao et al., Genetics of Somatic Mammalian Cells, VII. Induction and Isolation of Nutritional Mutants in Chinese Hamster Cells, *PNAS USA* (1968), 60:1275-1281.
Knol et al., Unidirectional Reconstitution into Detergent-Destablilized Liposomes of the Purified Lactose Transport System of *Streptococcus thermophilis*, *J. Biol. Chem.* (1996), 271(26):15358-15366.
Kohler et al., Immunoglobulin Chain Loss in Hybridoma Lines, *Proc. Natl. Acad. Sci. USA* (1980), 77:2197.
Kozbor et al., A Human Hybrid Myeloma for Production of Human Monoclonal Antibodies, *J. Immunol.* (1984), 133:3001-3005.
Kroger et al., Epitope-Mapping of Transglutaminase with Parallel Label-Free Optical Detection, *Biosens. Bioelectron.* (2002), 17(11-12):937-944.
Kurz et al., Psoralen Photo-Crosslinked mRNA-Puromycin Conjugates: A Novel Template for the Rapid and Facile Preparation of mRNA-Protein Fusions, *Nucleic Acids Res.* (2000), 28(18):E83.
Landschultz et al., The Leucine Zipper : A Hypothetical Structure Common to a New Class of DNA Binding Proteins, *Science* (1988), 240:1759-1764.
Lantto et al., A Divalent Antibody Format is Required for Neutralization of Human Cytomegalovirus Via Antigenic Domain 2 on Glycoprotein B, *J. Gen. Virol.* (2002), 83:2001-2005.
Leinonen et al., Epitope Mapping of Antibodies Against Prostate-Specific Antigen with Use of Peptide Libraries, *Clin. Chem.* (2002), 48(12):2208-2216.
Lemaitre et al., Specific Antiviral Activity of a Poly(L-Lysine)-Conjugated Oligodeoxyribonucleotide Sequence Complementary to a Vescular Stomatitis Virus N Protein mRNA Initiation Site, *Proc. Natl. Acad. Sci. USA* (1987), 84(3):648-652.
Lewin et al., Ribozyme Gene Therapy: Applications for Molecular Medicine, *Trends Mol. Med.* (2001),7(5):221-228.
Li et al., $\alpha_v\beta_3$ Expression on Blood Vessels and Melanoma Cells in Primary Lesions; Differential Association with Tumor Progression and Clinical Prognosis, *Cancer Immunol. Immunother* (2000), 49:243-252.
Liu et al., Optimized Synthesis of RNA-Protein Fusions for In Vitro Protein Selection, *Methods Enzymol.* (2000), 318:268-293.
Lohse et al., In Vitro Protein Display in Drug Discovery, *Curr. Opin. Drug Discov. Devel.* (2001), 4(2):198-204.
Lu et al., Expression of Thioredoxin Random Peptide Libraries on the *Escherichia coli* Cell Surface as Functional Fusions to Flagellin: A System Designed for Exploring Protein-Protein Interactions, *Biotechnology* (NY) (1995), 13(4):366-373.

(56) References Cited

OTHER PUBLICATIONS

Luzzago et al., Peptide and Protein Display on the Surface of Filamentous Bacteriophage, *Biotechnol. Annu. Rev.* (1995), 1:149-183.
Marcus-Sekura et al., Comparative Inhibition of Chloramphenicol Acetyltranferase Gene Expression by Antisense Aligonucleotide Analogues having Alkyl Phosphotriester, Methylphasphonate and Phosephorothioate Linkages, *Nucleic Acids Res.* (1987), 15(14):5749-5763.
McMahan et al., A Novel IL-1 Receptor, Cloned from B Cells by Mammalian Expression, is Expressed in Many Cell Types, *EMBO J.*, (1991), 10:2821-2832.
Menke et al., Antiviral Ribozymes. New Jobs for Ancient Molecules, *Mol. Biotechnol.* (1997), 8(1):17-33.
Morrison et al., Chimeric Human Antibody Molecules: Mouse Antigen-Binding Domains with Human Constant Region Domains, *Proc. Natl. Acad. Sci. USA* (1984), 81:6851-6855.
Muyldermans et al., Single Domain Camel Antibodies: Current Status, *J. Biotechnol.* (2001), 74:277-302.
Nemoto et al., In Vitro Virus: Bonding of mRNA bearing Puromycin at the 3[prime]-Terminal End to the C-Terminal End of its Encoded Protein on the Ribosome In Vitro, *FEBS Lett.* (1997), 414(2):405-408.
Neuberger et al., A Hapten-Specific Chimaeric IgE Antibody with Human Physiological Effector Function, *Nature* (1985), 314:268-270.
Newton et al., Angiogenin Single-Chain Immunofusions: Influence of Peptide Linkers and Spacers Between Fusion Protein Domains, *Biochemistry* (1996), 35:545-553.
Nielsen et al., Identification of Prokaryotic and Eukaryotic Signal Peptides and Prediction of their Cleavage Sites, *Protein Eng.* (1997), 10(1):1-6.
Norris et al., Design and Testing of Ribozymes for Cancer Gene Therapy, *Adv. Exp. Med. Biol.* (2000), 465:293-301.
Obungu et al., Determination of the Mechanism of Action of Anti-FasL Antibody by Epitope Mapping and Homology Modeling, *Biochemistry* (2009), 48:7251-7260.
O'Connell et al., Phage Versus Phagemid Libraries for Generation of Human Monoclonal Antibodies, *J. Mol. Biol.* (2002), 321(1):49-56.
Okayama et al., High-Efficiency Cloning of Full-Length cDNA, *Mol. Cell. Biol.* (1982), 2:161-170.
Palakodeti et al., The Molecular Basis for Modulation of Human Vγ9Vδ2 T Cell Responses by CD277/Butyrophilin-3 (BTN3A)-Specific Antibodies., *J. Biol. Chem.* (2012) 287:32780-32790.
Parmley et al., Filamentous Fusion Phage Cloning Vectors for the Study of Epitopes and Design of Vaccines, *Adv. Exp. Med. Biol.* (1989), 251:215-218.
Peach et al., Both Extracellular Immunoglobin-Like Domains of CD80 Contain Residues Critical for Binding T Cell Surface Receptors CTLA-4 and CD28, *J. Biol. Chem.* (1995), 270(36):21181-21187.
Pini et al., Phage Display of Antibody Fragments, *Curr. Protein Pept. Sci.* (2000), 1(2):155-169.
Powers et al., Expression of Single-Chain Fv-Fc Fusions in *Pichia pastoris*, *J. Immunol.* (2001), 251:123-135.
Roberts et al., RNA-Peptide Fusions for the In Vitro Selection of Peptides and Proteins, *Proc. Natl. Acad. Sci.* (1997), 94:12297-12302.
Rönnmark et al., Construction and Characterization of Affibody-Fc Chimeras Produced in *Escherichia coli.*, *J. Immunol. Methods* (2002), 261(1-2):199-211.
Saiki et al., Primer-Directed Enzymatic Amplification of DNA with a Thermostable DNA Polymerase, *Science* (1988), 239:487-491.
Santiago et al., Nucleic Acid Based Strategies as Potential Therapeutic Tools: Mechanistic Considerations and Implications to Restenosis, *J. Mol. Med.* (2001), 79(12):695-706.
Sarin et al., Inhibition of Acquired Immunodeficiency Syndrome Virus by Oligodeoxynucleoside Methylposphonates, *Proc. Natl. Acad. Sci. USA* (1988), 85(20):7448-7451.
Schmitz et al., Phage Display : A Molecular Tool for the Generation of Antibodies—A Review, *Placenta*, Supp. A (2000), 21:S106-S112.
Shibui et al., Cloning, Expression Analysis, and Chromosomal Localization of a Novel Butyrophilin-Like Receptor., *J. Hum. Genet.* (1999), 44(4):249-252.
Sioud, Nucleic Acid Enzymes as a Novel Generation of Anti-Gene Agents, *Curr. Mol. Med.* (2001), 1(5):575-588.
Souriau et al., Recombinant Antibodies for Cancer Diagnosis and Therapy, *Expert Opin. Bio. Ther.* (2001), 1(5):845-855.
Swanson et al., Butylrophilin-Like 2 Modulates B7 Costimulation to Induce Foxp3 Expression and Regulatory T Cell Development in Mature T Cells, *J. Immunol.* (2013), 190:2027-2035.
Takeda et al., Construction of Chimaeric Processed Immunoglobulin Genes Containing Mouse Variable and Human Constant Region Sequences, *Nature* (1985), 314:452-454.
Valentonyte et al., Sarcoidosis is Associated with a Truncating Splice Site Mutation in BTNL2, *Nature Genetics* (2005), 37(4):357-364.
Von Heijne, Patterns of Amino Acids Near Signal-Sequence Cleavage Sites, *Eur. J. Biochem.* (1983), 133:17-21.
Von Heijne, Signal Sequences, *J. Mol. Biol.* (1985), 184:99-105.
Whitlow et al., An Improved Linker for Single-Chain Fv with Reduced Aggregation and Enhanced Proteolytic Stability, *Protein Engineering* (1993), 6:989-995.
Williams et al., The Immunoglobulin Superfamily-Domains for Cell Surface Recognition, *Ann. Rev. Immunol.* (1988), 6:381-405.
Yamashiro et al., Stimulation of Human Butyrophilin 3 Molecules Results in Negative Regulation of Cellular Immunity, *J. Leuk. Biol.* (2010), 88(4):757-767.
Yamazaki et al., A Butyrophilin Family Member Critically Inhibits T Cell Activation, *J. Immunol.* (2010), 185(10):5907-5914.
Zhu et al., Identification of Epitopes of Trichosanthin by Phage Peptide Library, *Biochem. Biophys. Res. Commun.* (2001), 282(4):921-927.
Zon, Oligonucleotide Analogues as Potential Chemotherapeutic Agents, *Pharm. Res.* (1988), 5(9):539-549.

\* cited by examiner

SEQUENCE LISTING

```
<160> NUMBER OF SEQ ID NOS: 23

<210> SEQ ID NO 1
<211> LENGTH: 1401
<212> TYPE: DNA
<213> ORGANISM: Homo sapiens
<220> FEATURE:
<221> NAME/KEY: CDS
<222> LOCATION: (1)..(1401)

<400> SEQUENCE: 1 atg gct ttt gtg ctc att ttg gtt ctc agt ttc tac gag ctg gtg tca      48
Met Ala Phe Val Leu Ile Leu Val Leu Ser Phe Tyr Glu Leu Val Ser
1               5                   10                  15 gga cag tgg caa gtc act gga ccg ggc aag ttt gtc cag gcc ttg gtg      96
Gly Gln Trp Gln Val Thr Gly Pro Gly Lys Phe Val Gln Ala Leu Val
                20                  25                  30 ggg gag gac gcc gtg ttc tcc tgc tcc ctc ttt cct gag acc agt gca     144
Gly Glu Asp Ala Val Phe Ser Cys Ser Leu Phe Pro Glu Thr Ser Ala
            35                  40                  45 gag gct atg gaa gtg cgg ttc ttc agg aat cag ttc cat gct gtg gtc     192
Glu Ala Met Glu Val Arg Phe Phe Arg Asn Gln Phe His Ala Val Val
        50                  55                  60 cac ctc tac aga gat ggg gaa gac tgg gaa tct aag cag atg cca cag     240
His Leu Tyr Arg Asp Gly Glu Asp Trp Glu Ser Lys Gln Met Pro Gln
65                  70                  75                  80 tat cga ggg aga act gag ttt gtg aag gac tcc att gca ggg ggg cgt     288
Tyr Arg Gly Arg Thr Glu Phe Val Lys Asp Ser Ile Ala Gly Gly Arg
                85                  90                  95 gtc tct cta agg cta aaa aac atc act ccc tcg gac atc ggc ctg tat     336
Val Ser Leu Arg Leu Lys Asn Ile Thr Pro Ser Asp Ile Gly Leu Tyr
                100                 105                 110 ggg tgc tgg ttc agt tcc cag att tac gat gag gag gcc acc tgg gag     384
Gly Cys Trp Phe Ser Ser Gln Ile Tyr Asp Glu Glu Ala Thr Trp Glu
            115                 120                 125 ctg cgg gtg gca gca ctg ggc tca ctt cct ctc att tcc atc gtg gga     432
Leu Arg Val Ala Ala Leu Gly Ser Leu Pro Leu Ile Ser Ile Val Gly
        130                 135                 140 tat gtt gac gga ggt atc cag tta ctc tgc ctg tcc tca ggc tgg ttc     480
Tyr Val Asp Gly Gly Ile Gln Leu Leu Cys Leu Ser Ser Gly Trp Phe
145                 150                 155                 160
```

-continued

| | | |
|---|---|---|
| ccc cag ccc aca gcc aag tgg aaa ggt cca caa gga cag gat ttg tct<br>Pro Gln Pro Thr Ala Lys Trp Lys Gly Pro Gln Gly Gln Asp Leu Ser<br>               165                      170                   175 | 528 |
| tca gac tcc aga gca aat gca gat ggg tac agc ctg tat gat gtg gag<br>Ser Asp Ser Arg Ala Asn Ala Asp Gly Tyr Ser Leu Tyr Asp Val Glu<br>               180                      185                   190 | 576 |
| atc tcc att ata gtc cag gaa aat gct ggg agc ata ttg tgt tcc atc<br>Ile Ser Ile Ile Val Gln Glu Asn Ala Gly Ser Ile Leu Cys Ser Ile<br>               195                      200                   205 | 624 |
| cac ctt gct gag cag agt cat gag gtg gaa tcc aag gta ttg ata gga<br>His Leu Ala Glu Gln Ser His Glu Val Glu Ser Lys Val Leu Ile Gly<br>     210                      215                      220 | 672 |
| gag acg ttt ttc cag ccc tca cct tgg cgc ctg gct tct att tta ctc<br>Glu Thr Phe Phe Gln Pro Ser Pro Trp Arg Leu Ala Ser Ile Leu Leu<br>225                      230                      235                   240 | 720 |
| ggg tta ctc tgt ggt gcc ctg tgt ggt gtt gtc atg ggg atg ata att<br>Gly Leu Leu Cys Gly Ala Leu Cys Gly Val Val Met Gly Met Ile Ile<br>                     245                      250                   255 | 768 |
| gtt ttc ttc aaa tcc aaa ggg aaa atc cag gcg gaa ctg gac tgg aga<br>Val Phe Phe Lys Ser Lys Gly Lys Ile Gln Ala Glu Leu Asp Trp Arg<br>             260                      265                   270 | 816 |
| aga aag cac gga cag gca gaa ttg aga gac gcc cgg aaa cac gca gtg<br>Arg Lys His Gly Gln Ala Glu Leu Arg Asp Ala Arg Lys His Ala Val<br>     275                      280                      285 | 864 |
| gag gtg act ctg gat cca gag acg gct cac ccg aag ctc tgc gtt tct<br>Glu Val Thr Leu Asp Pro Glu Thr Ala His Pro Lys Leu Cys Val Ser<br>         290                      295                   300 | 912 |
| gat ctg aaa act gta acc cat aga aaa gct ccc cag gag gtg cct cac<br>Asp Leu Lys Thr Val Thr His Arg Lys Ala Pro Gln Glu Val Pro His<br>305                      310                      315                   320 | 960 |
| tct gag aag aga ttt aca agg aag agt gtg gtg gct tct cag ggt ttc<br>Ser Glu Lys Arg Phe Thr Arg Lys Ser Val Val Ala Ser Gln Gly Phe<br>             325                      330                   335 | 1008 |
| caa gca ggg aaa cat tac tgg gag gtg gac gtg gga caa aat gta ggg<br>Gln Ala Gly Lys His Tyr Trp Glu Val Asp Val Gly Gln Asn Val Gly<br>     340                      345                      350 | 1056 |
| tgg tat gtg gga gtg tgt cgg gat gac gta gac agg ggg aag aac aat<br>Trp Tyr Val Gly Val Cys Arg Asp Asp Val Asp Arg Gly Lys Asn Asn<br>         355                      360                   365 | 1104 |
| gtg act ttg tct ccc aac aat ggg tat tgg gtc ctc aga ctg aca aca<br>Val Thr Leu Ser Pro Asn Asn Gly Tyr Trp Val Leu Arg Leu Thr Thr<br>             370                      375                   380 | 1152 |
| gaa cat ttg tat ttc aca ttc aat ccc cat ttt atc agc ctc ccc ccc<br>Glu His Leu Tyr Phe Thr Phe Asn Pro His Phe Ile Ser Leu Pro Pro<br>385                      390                      395                   400 | 1200 |
| agc acc cct cct aca cga gta ggg gtc ttc ctg gac tat gag ggt ggg<br>Ser Thr Pro Pro Thr Arg Val Gly Val Phe Leu Asp Tyr Glu Gly Gly<br>                     405                      410                   415 | 1248 |
| acc atc tcc ttc ttc aat aca aat gac cag tcc ctt att tat acc ctg<br>Thr Ile Ser Phe Phe Asn Thr Asn Asp Gln Ser Leu Ile Tyr Thr Leu<br>               420                      425                   430 | 1296 |
| ctg aca tgt cag ttt gaa ggc ttg ttg aga ccc tat atc cag cat gcg<br>Leu Thr Cys Gln Phe Glu Gly Leu Leu Arg Pro Tyr Ile Gln His Ala<br>         435                      440                      445 | 1344 |
| atg tat gac gag gaa aag ggg act ccc ata ttc ata tgt cca gtg tcc<br>Met Tyr Asp Glu Glu Lys Gly Thr Pro Ile Phe Ile Cys Pro Val Ser<br>     450                      455                      460 | 1392 |
| tgg gga tga<br>Trp Gly<br>465 | 1401 |

```
<210> SEQ ID NO 2
<211> LENGTH: 466
<212> TYPE: PRT
<213> ORGANISM: Homo sapiens

<400> SEQUENCE: 2
```

| | | | | | | | | | | | | | | | |
|---|---|---|---|---|---|---|---|---|---|---|---|---|---|---|---|
| Met | Ala | Phe | Val | Leu | Ile | Leu | Val | Leu | Ser | Phe | Tyr | Glu | Leu | Val | Ser |
| 1 | | | | 5 | | | | | 10 | | | | | 15 | |
| Gly | Gln | Trp | Gln | Val | Thr | Gly | Pro | Gly | Lys | Phe | Val | Gln | Ala | Leu | Val |
| | | | 20 | | | | | 25 | | | | | 30 | | |
| Gly | Glu | Asp | Ala | Val | Phe | Ser | Cys | Ser | Leu | Phe | Pro | Glu | Thr | Ser | Ala |
| | | | 35 | | | | | 40 | | | | | 45 | | |
| Glu | Ala | Met | Glu | Val | Arg | Phe | Phe | Arg | Asn | Gln | Phe | His | Ala | Val | Val |
| | | 50 | | | | | 55 | | | | | 60 | | | |
| His | Leu | Tyr | Arg | Asp | Gly | Glu | Asp | Trp | Glu | Ser | Lys | Gln | Met | Pro | Gln |
| 65 | | | | | 70 | | | | | 75 | | | | | 80 |
| Tyr | Arg | Gly | Arg | Thr | Glu | Phe | Val | Lys | Asp | Ser | Ile | Ala | Gly | Gly | Arg |
| | | | | 85 | | | | | 90 | | | | | 95 | |
| Val | Ser | Leu | Arg | Leu | Lys | Asn | Ile | Thr | Pro | Ser | Asp | Ile | Gly | Leu | Tyr |
| | | | 100 | | | | | 105 | | | | | 110 | | |
| Gly | Cys | Trp | Phe | Ser | Ser | Gln | Ile | Tyr | Asp | Glu | Glu | Ala | Thr | Trp | Glu |
| | | | 115 | | | | | 120 | | | | | 125 | | |
| Leu | Arg | Val | Ala | Ala | Leu | Gly | Ser | Leu | Pro | Leu | Ile | Ser | Ile | Val | Gly |
| | | 130 | | | | | 135 | | | | | 140 | | | |
| Tyr | Val | Asp | Gly | Gly | Ile | Gln | Leu | Leu | Cys | Leu | Ser | Ser | Gly | Trp | Phe |
| 145 | | | | | 150 | | | | | 155 | | | | | 160 |
| Pro | Gln | Pro | Thr | Ala | Lys | Trp | Lys | Gly | Pro | Gln | Gly | Gln | Asp | Leu | Ser |
| | | | | 165 | | | | | 170 | | | | | 175 | |
| Ser | Asp | Ser | Arg | Ala | Asn | Ala | Asp | Gly | Tyr | Ser | Leu | Tyr | Asp | Val | Glu |
| | | | 180 | | | | | 185 | | | | | 190 | | |
| Ile | Ser | Ile | Ile | Val | Gln | Glu | Asn | Ala | Gly | Ser | Ile | Leu | Cys | Ser | Ile |
| | | | 195 | | | | | 200 | | | | | 205 | | |
| His | Leu | Ala | Glu | Gln | Ser | His | Glu | Val | Glu | Ser | Lys | Val | Leu | Ile | Gly |
| | | 210 | | | | | 215 | | | | | 220 | | | |
| Glu | Thr | Phe | Phe | Gln | Pro | Ser | Pro | Trp | Arg | Leu | Ala | Ser | Ile | Leu | Leu |
| 225 | | | | | 230 | | | | | 235 | | | | | 240 |
| Gly | Leu | Leu | Cys | Gly | Ala | Leu | Cys | Gly | Val | Val | Met | Gly | Met | Ile | Ile |
| | | | | 245 | | | | | 250 | | | | | 255 | |
| Val | Phe | Phe | Lys | Ser | Lys | Gly | Lys | Ile | Gln | Ala | Glu | Leu | Asp | Trp | Arg |
| | | | 260 | | | | | 265 | | | | | 270 | | |
| Arg | Lys | His | Gly | Gln | Ala | Glu | Leu | Arg | Asp | Ala | Arg | Lys | His | Ala | Val |
| | | | 275 | | | | | 280 | | | | | 285 | | |
| Glu | Val | Thr | Leu | Asp | Pro | Glu | Thr | Ala | His | Pro | Lys | Leu | Cys | Val | Ser |
| | | 290 | | | | | 295 | | | | | 300 | | | |
| Asp | Leu | Lys | Thr | Val | Thr | His | Arg | Lys | Ala | Pro | Gln | Glu | Val | Pro | His |
| 305 | | | | | 310 | | | | | 315 | | | | | 320 |
| Ser | Glu | Lys | Arg | Phe | Thr | Arg | Lys | Ser | Val | Val | Ala | Ser | Gln | Gly | Phe |
| | | | | 325 | | | | | 330 | | | | | 335 | |
| Gln | Ala | Gly | Lys | His | Tyr | Trp | Glu | Val | Asp | Val | Gly | Gln | Asn | Val | Gly |
| | | | 340 | | | | | 345 | | | | | 350 | | |
| Trp | Tyr | Val | Gly | Val | Cys | Arg | Asp | Asp | Val | Asp | Arg | Gly | Lys | Asn | Asn |
| | | | | 355 | | | | | 360 | | | | | 365 | |
| Val | Thr | Leu | Ser | Pro | Asn | Asn | Gly | Tyr | Trp | Val | Leu | Arg | Leu | Thr | Thr |
| | | 370 | | | | | 375 | | | | | 380 | | | |

```
Glu His Leu Tyr Phe Thr Phe Asn Pro His Phe Ile Ser Leu Pro Pro
385                 390                 395                 400

Ser Thr Pro Pro Thr Arg Val Gly Val Phe Leu Asp Tyr Glu Gly Gly
                405                 410                 415

Thr Ile Ser Phe Phe Asn Thr Asn Asp Gln Ser Leu Ile Tyr Thr Leu
                420                 425                 430

Leu Thr Cys Gln Phe Glu Gly Leu Leu Arg Pro Tyr Ile Gln His Ala
            435                 440                 445

Met Tyr Asp Glu Glu Lys Gly Thr Pro Ile Phe Ile Cys Pro Val Ser
    450                 455                 460

Trp Gly
465

<210> SEQ ID NO 3
<211> LENGTH: 20
<212> TYPE: PRT
<213> ORGANISM: Homo sapiens

<400> SEQUENCE: 3

Met Glu Thr Asp Thr Leu Leu Leu Trp Val Leu Leu Leu Trp Val Pro
1               5                   10                  15

Gly Ser Thr Gly
            20

<210> SEQ ID NO 4
<211> LENGTH: 26
<212> TYPE: PRT
<213> ORGANISM: Homo sapiens

<400> SEQUENCE: 4

Met Ala Thr Gly Ser Arg Thr Ser Leu Leu Leu Ala Phe Gly Leu Leu
1               5                   10                  15

Cys Leu Pro Trp Leu Gln Glu Gly Ser Ala
            20                  25

<210> SEQ ID NO 5
<211> LENGTH: 1437
<212> TYPE: DNA
<213> ORGANISM: Artificial Sequence
<220> FEATURE:
<223> OTHER INFORMATION: Fusion Protein
<220> FEATURE:
<221> NAME/KEY: CDS
<222> LOCATION: (1)..(1437)

<400> SEQUENCE: 5 atg gct ttt gtg ctc att ttg gtt ctc agt ttc tac gag ctg gtg tca      48
Met Ala Phe Val Leu Ile Leu Val Leu Ser Phe Tyr Glu Leu Val Ser
1               5                   10                  15 gga cag tgg caa gtc act gga ccg ggc aag ttt gtc cag gcc ttg gtg      96
Gly Gln Trp Gln Val Thr Gly Pro Gly Lys Phe Val Gln Ala Leu Val
            20                  25                  30 ggg gag gac gcc gtg ttc tcc tgc tcc ctc ttt cct gag acc agt gca     144
Gly Glu Asp Ala Val Phe Ser Cys Ser Leu Phe Pro Glu Thr Ser Ala
        35                  40                  45 gag gct atg gaa gtg cgg ttc ttc agg aat cag ttc cat gct gtg gtc     192
Glu Ala Met Glu Val Arg Phe Phe Arg Asn Gln Phe His Ala Val Val
    50                  55                  60 cac ctc tac aga gat ggg gaa gac tgg gaa tct aag cag atg cca cag     240
His Leu Tyr Arg Asp Gly Glu Asp Trp Glu Ser Lys Gln Met Pro Gln
65                  70                  75                  80
```

| | | |
|---|---|---|
| tat cga ggg aga act gag ttt gtg aag gac tcc att gca ggg ggg cgt<br>Tyr Arg Gly Arg Thr Glu Phe Val Lys Asp Ser Ile Ala Gly Gly Arg<br>                 85                 90                 95 | | 288 |
| gtc tct cta agg cta aaa aac atc act ccc tcg gac atc ggc ctg tat<br>Val Ser Leu Arg Leu Lys Asn Ile Thr Pro Ser Asp Ile Gly Leu Tyr<br>100                      105                    110 | | 336 |
| ggg tgc tgg ttc agt tcc cag att tac gat gag gag gcc acc tgg gag<br>Gly Cys Trp Phe Ser Ser Gln Ile Tyr Asp Glu Glu Ala Thr Trp Glu<br>         115                   120                 125 | | 384 |
| ctg cgg gtg gca gca ctg ggc tca ctt cct ctc att tcc atc gtg gga<br>Leu Arg Val Ala Ala Leu Gly Ser Leu Pro Leu Ile Ser Ile Val Gly<br>130                      135                    140 | | 432 |
| tat gtt gac gga ggt atc cag tta ctc tgc ctg tcc tca ggc tgg ttc<br>Tyr Val Asp Gly Gly Ile Gln Leu Leu Cys Leu Ser Ser Gly Trp Phe<br>145                      150                    155                    160 | | 480 |
| ccc cag ccc aca gcc aag tgg aaa ggt cca caa gga cag gat ttg tct<br>Pro Gln Pro Thr Ala Lys Trp Lys Gly Pro Gln Gly Gln Asp Leu Ser<br>                   165                    170                    175 | | 528 |
| tca gac tcc aga gca aat gca gat ggg tac agc ctg tat gat gtg gag<br>Ser Asp Ser Arg Ala Asn Ala Asp Gly Tyr Ser Leu Tyr Asp Val Glu<br>                  180                    185                    190 | | 576 |
| atc tcc att ata gtc cag gaa aat gct ggg agc ata ttg tgt tcc atc<br>Ile Ser Ile Ile Val Gln Glu Asn Ala Gly Ser Ile Leu Cys Ser Ile<br>             195                    200                    205 | | 624 |
| cac ctt gct gag cag agt cat gag gtg gaa tcc aag gta ttg ata gga<br>His Leu Ala Glu Gln Ser His Glu Val Glu Ser Lys Val Leu Ile Gly<br>210                      215                    220 | | 672 |
| gag acg ttt ttc cag ccc tca cct tgg cgc ctg gct gga ggt gga ggc<br>Glu Thr Phe Phe Gln Pro Ser Pro Trp Arg Leu Ala Gly Gly Gly Gly<br>225                      230                    235                    240 | | 720 |
| tcc gga ggt gga ggt tcc ggt gga ggt gga tcc gac aaa act cac aca<br>Ser Gly Gly Gly Gly Ser Gly Gly Gly Gly Ser Asp Lys Thr His Thr<br>                     245                    250                    255 | | 768 |
| tgt cca ccg tgc cca gca cct gaa ctc ctg ggg gga ccg tca gtt ttc<br>Cys Pro Pro Cys Pro Ala Pro Glu Leu Leu Gly Gly Pro Ser Val Phe<br>                  260                    265                    270 | | 816 |
| ctc ttc ccc cca aaa ccc aag gac acc ctc atg atc tcc cgg acc cct<br>Leu Phe Pro Pro Lys Pro Lys Asp Thr Leu Met Ile Ser Arg Thr Pro<br>         275                   280                    285 | | 864 |
| gag gtc aca tgc gtg gtg gtg gac gtg agc cac gaa gac cct gag gtc<br>Glu Val Thr Cys Val Val Val Asp Val Ser His Glu Asp Pro Glu Val<br>290                      295                    300 | | 912 |
| aag ttc aac tgg tac gtg gac ggc gtg gag gtg cat aat gcc aag aca<br>Lys Phe Asn Trp Tyr Val Asp Gly Val Glu Val His Asn Ala Lys Thr<br>305                      310                    315                    320 | | 960 |
| aag ccg cgg gag gag cag tac aac agc acg tac cgt gtg gtc agc gtc<br>Lys Pro Arg Glu Glu Gln Tyr Asn Ser Thr Tyr Arg Val Val Ser Val<br>                     325                    330                    335 | | 1008 |
| ctc acc gtc ctg cac cag gac tgg ctg aat ggc aag gag tac aag tgc<br>Leu Thr Val Leu His Gln Asp Trp Leu Asn Gly Lys Glu Tyr Lys Cys<br>                  340                    345                    350 | | 1056 |
| aag gtc tcc aac aaa gcc ctc cca gcc ccc atc gag aaa acc atc tcc<br>Lys Val Ser Asn Lys Ala Leu Pro Ala Pro Ile Glu Lys Thr Ile Ser<br>             355                    360                    365 | | 1104 |
| aaa gcc aaa ggg cag ccc cga gaa cca cag gtg tac acc ctg ccc cca<br>Lys Ala Lys Gly Gln Pro Arg Glu Pro Gln Val Tyr Thr Leu Pro Pro<br>370                      375                    380 | | 1152 |
| tcc cgg gat gag ctg acc aag aac cag gtc agc ctg acc tgc ctg gtc<br>Ser Arg Asp Glu Leu Thr Lys Asn Gln Val Ser Leu Thr Cys Leu Val<br>385                      390                    395                    400 | | 1200 |

```
aaa ggc ttc tat ccc agc gac atc gcc gtg gag tgg gag agc aat ggg    1248
Lys Gly Phe Tyr Pro Ser Asp Ile Ala Val Glu Trp Glu Ser Asn Gly
            405                 410                 415 cag ccg gag aac aac tac aag acc acg cct ccc gtg ctg gac tcc gac    1296
Gln Pro Glu Asn Asn Tyr Lys Thr Thr Pro Pro Val Leu Asp Ser Asp
        420                 425                 430 ggc tcc ttc ttc ctc tac agc aag ctc acc gtg gac aag agc agg tgg    1344
Gly Ser Phe Phe Leu Tyr Ser Lys Leu Thr Val Asp Lys Ser Arg Trp
        435                 440                 445 cag cag ggg aac gtc ttc tca tgc tcc gtg atg cat gag gct ctg cac    1392
Gln Gln Gly Asn Val Phe Ser Cys Ser Val Met His Glu Ala Leu His
        450                 455                 460 aac cac tac acg cag aag agc ctc tcc ctg tct ccg ggt aaa tga        1437
Asn His Tyr Thr Gln Lys Ser Leu Ser Leu Ser Pro Gly Lys
465                 470                 475

<210> SEQ ID NO 6
<211> LENGTH: 478
<212> TYPE: PRT
<213> ORGANISM: Artificial Sequence
<220> FEATURE:
<223> OTHER INFORMATION: Synthetic Construct

<400> SEQUENCE: 6

Met Ala Phe Val Leu Ile Leu Val Leu Ser Phe Tyr Glu Leu Val Ser
1               5                   10                  15

Gly Gln Trp Gln Val Thr Gly Pro Gly Lys Phe Val Gln Ala Leu Val
                20                  25                  30

Gly Glu Asp Ala Val Phe Ser Cys Ser Leu Phe Pro Glu Thr Ser Ala
            35                  40                  45

Glu Ala Met Glu Val Arg Phe Phe Arg Asn Gln Phe His Ala Val Val
        50                  55                  60

His Leu Tyr Arg Asp Gly Glu Asp Trp Glu Ser Lys Gln Met Pro Gln
65                  70                  75                  80

Tyr Arg Gly Arg Thr Glu Phe Val Lys Asp Ser Ile Ala Gly Gly Arg
                85                  90                  95

Val Ser Leu Arg Leu Lys Asn Ile Thr Pro Ser Asp Ile Gly Leu Tyr
            100                 105                 110

Gly Cys Trp Phe Ser Ser Gln Ile Tyr Asp Glu Glu Ala Thr Trp Glu
        115                 120                 125

Leu Arg Val Ala Ala Leu Gly Ser Leu Pro Leu Ile Ser Ile Val Gly
    130                 135                 140

Tyr Val Asp Gly Gly Ile Gln Leu Leu Cys Leu Ser Ser Gly Trp Phe
145                 150                 155                 160

Pro Gln Pro Thr Ala Lys Trp Lys Gly Pro Gln Gly Gln Asp Leu Ser
                165                 170                 175

Ser Asp Ser Arg Ala Asn Ala Asp Gly Tyr Ser Leu Tyr Asp Val Glu
            180                 185                 190

Ile Ser Ile Ile Val Gln Glu Asn Ala Gly Ser Ile Leu Cys Ser Ile
        195                 200                 205

His Leu Ala Glu Gln Ser His Glu Val Glu Ser Lys Val Leu Ile Gly
    210                 215                 220

Glu Thr Phe Phe Gln Pro Ser Pro Trp Arg Leu Ala Gly Gly Gly Gly
225                 230                 235                 240

Ser Gly Gly Gly Gly Ser Gly Gly Gly Gly Ser Asp Lys Thr His Thr
                245                 250                 255
```

```
Cys Pro Pro Cys Pro Ala Pro Glu Leu Leu Gly Gly Pro Ser Val Phe
            260                 265                 270

Leu Phe Pro Pro Lys Pro Lys Asp Thr Leu Met Ile Ser Arg Thr Pro
275                 280                 285

Glu Val Thr Cys Val Val Val Asp Val Ser His Glu Asp Pro Glu Val
        290                 295                 300

Lys Phe Asn Trp Tyr Val Asp Gly Val Glu Val His Asn Ala Lys Thr
305                 310                 315                 320

Lys Pro Arg Glu Glu Gln Tyr Asn Ser Thr Tyr Arg Val Val Ser Val
                325                 330                 335

Leu Thr Val Leu His Gln Asp Trp Leu Asn Gly Lys Glu Tyr Lys Cys
            340                 345                 350

Lys Val Ser Asn Lys Ala Leu Pro Ala Pro Ile Glu Lys Thr Ile Ser
355                 360                 365

Lys Ala Lys Gly Gln Pro Arg Glu Pro Gln Val Tyr Thr Leu Pro Pro
        370                 375                 380

Ser Arg Asp Glu Leu Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
            420                 425                 430

Gly Ser Phe Phe Leu Tyr Ser Lys Leu Thr Val Asp Lys Ser Arg Trp
435                 440                 445

Gln Gln Gly Asn Val Phe Ser Cys Ser Val Met His Glu Ala Leu His
        450                 455                 460

Asn His Tyr Thr Gln Lys Ser Leu Ser Leu Ser Pro Gly Lys
465                 470                 475

<210> SEQ ID NO 7
<211> LENGTH: 461
<212> TYPE: PRT
<213> ORGANISM: Artificial Sequence
<220> FEATURE:
<223> OTHER INFORMATION: Fusion Protein

<400> SEQUENCE: 7

Gln Trp Gln Val Thr Gly Pro Gly Lys Phe Val Gln Ala Leu Val Gly
1               5                   10                  15

Glu Asp Ala Val Phe Ser Cys Ser Leu Phe Pro Glu Thr Ser Ala Glu
            20                  25                  30

Ala Met Glu Val Arg Phe Phe Arg Asn Gln Phe His Ala Val Val His
        35                  40                  45

Leu Tyr Arg Asp Gly Glu Asp Trp Glu Ser Lys Gln Met Pro Gln Tyr
    50                  55                  60

Arg Gly Arg Thr Glu Phe Val Lys Asp Ser Ile Ala Gly Gly Arg Val
65                  70                  75                  80

Ser Leu Arg Leu Lys Asn Ile Thr Pro Ser Asp Ile Gly Leu Tyr Gly
                85                  90                  95

Cys Trp Phe Ser Ser Gln Ile Tyr Asp Glu Glu Ala Thr Trp Glu Leu
            100                 105                 110

Arg Val Ala Ala Leu Gly Ser Leu Pro Leu Ile Ser Ile Val Gly Tyr
        115                 120                 125

Val Asp Gly Gly Ile Gln Leu Leu Cys Leu Ser Ser Gly Trp Phe Pro
    130                 135                 140
```

-continued

```
Gln Pro Thr Ala Lys Trp Lys Gly Pro Gln Gly Gln Asp Leu Ser Ser
145                 150                 155                 160

Asp Ser Arg Ala Asn Ala Asp Gly Tyr Ser Leu Tyr Asp Val Glu Ile
                165                 170                 175

Ser Ile Ile Val Gln Glu Asn Ala Gly Ser Ile Leu Cys Ser Ile His
            180                 185                 190

Leu Ala Glu Gln Ser His Glu Val Glu Ser Lys Val Leu Ile Gly Glu
        195                 200                 205

Thr Phe Phe Gln Pro Ser Pro Trp Arg Leu Ala Gly Gly Gly Gly Ser
210                 215                 220

Gly Gly Gly Gly Ser Gly Gly Gly Ser Asp Lys Thr His Thr Cys
225                 230                 235                 240

Pro Pro Cys Pro Ala Pro Glu Leu Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Pro Ile Glu Lys Thr Ile Ser Lys
            340                 345                 350

Ala Lys Gly Gln Pro Arg Glu Pro Gln Val Tyr Thr Leu Pro Pro Ser
        355                 360                 365

Arg Asp Glu Leu Thr Lys Asn Gln Val Ser Leu Thr Cys Leu Val Lys
370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
450                 455                 460
```

<210> SEQ ID NO 8
<211> LENGTH: 1299
<212> TYPE: DNA
<213> ORGANISM: Homo sapiens
<220> FEATURE:
<221> NAME/KEY: CDS
<222> LOCATION: (1)..(1299)

<400> SEQUENCE: 8

```
atg gct ttt gtg ctc att ttg gtt ctc agt ttc tac gag ctg gtg tca      48
Met Ala Phe Val Leu Ile Leu Val Leu Ser Phe Tyr Glu Leu Val Ser
1               5                   10                  15 gga cag tgg caa gtc act gga ccg ggc aag ttt gtc cag gcc ttg gtg      96
Gly Gln Trp Gln Val Thr Gly Pro Gly Lys Phe Val Gln Ala Leu Val
                20                  25                  30
```

| | | |
|---|---|---|
| ggg gag gac gcc gtg ttc tcc tgc tcc ctc ttt cct gag acc agt gca<br>Gly Glu Asp Ala Val Phe Ser Cys Ser Leu Phe Pro Glu Thr Ser Ala<br>       35                   40                 45 | | 144 |
| gag gct atg gaa gtg cgg ttc ttc agg aat cag ttc cat gct gtg gtc<br>Glu Ala Met Glu Val Arg Phe Phe Arg Asn Gln Phe His Ala Val Val<br> 50                     55                   60 | | 192 |
| cac ctc tac aga gat ggg gaa gac tgg gaa tct aag cag atg cca cag<br>His Leu Tyr Arg Asp Gly Glu Asp Trp Glu Ser Lys Gln Met Pro Gln<br>65                     70                  75                  80 | | 240 |
| tat cga ggg aga act gag ttt gtg aag gac tcc att gca ggg ggc cgt<br>Tyr Arg Gly Arg Thr Glu Phe Val Lys Asp Ser Ile Ala Gly Gly Arg<br>               85                   90                 95 | | 288 |
| gtc tct cta agg cta aaa aac atc act ccc tcg gac atc ggc ctg tat<br>Val Ser Leu Arg Leu Lys Asn Ile Thr Pro Ser Asp Ile Gly Leu Tyr<br>            100                105               110 | | 336 |
| ggg tgc tgg ttc agt tcc cag att tac gat gag gag gcc acc tgg gag<br>Gly Cys Trp Phe Ser Ser Gln Ile Tyr Asp Glu Glu Ala Thr Trp Glu<br>               115                120               125 | | 384 |
| ctg cgg gtg gca gca ctg ggc tca ctt cct ctc att tcc atc gtg gga<br>Leu Arg Val Ala Ala Leu Gly Ser Leu Pro Leu Ile Ser Ile Val Gly<br>130                    135                140 | | 432 |
| tat gtt gac gga ggt atc cag tta ctc tgc ctg tcc tca ttc cag ccc<br>Tyr Val Asp Gly Gly Ile Gln Leu Leu Cys Leu Ser Ser Phe Gln Pro<br>145                    150               155              160 | | 480 |
| tca cct tgg cgc ctg gct tct att tta ctc ggg tta ctc tgt ggt gcc<br>Ser Pro Trp Arg Leu Ala Ser Ile Leu Leu Gly Leu Leu Cys Gly Ala<br>               165                170               175 | | 528 |
| ctg tgt ggt gtt gtc atg ggg atg ata att gtt ttc ttc aaa tcc aaa<br>Leu Cys Gly Val Val Met Gly Met Ile Ile Val Phe Phe Lys Ser Lys<br>           180                185               190 | | 576 |
| ggg aaa atc cag gcg gaa ctg ggt atg tgt cat gtc ctg agc ctc cca<br>Gly Lys Ile Gln Ala Glu Leu Gly Met Cys His Val Leu Ser Leu Pro<br>               195                200               205 | | 624 |
| cac atg gtt ctc ccg ggt ccc tcc ctg atc cac agt ttg agc ctc tgg<br>His Met Val Leu Pro Gly Pro Ser Leu Ile His Ser Leu Ser Leu Trp<br>           210                215               220 | | 672 |
| acg acc ctg gct gca ggc tgg aca gga agc acc gac tgg aga aga aag<br>Thr Thr Leu Ala Ala Gly Trp Thr Gly Ser Thr Asp Trp Arg Arg Lys<br>225                    230               235              240 | | 720 |
| cac gga cag gca gaa ttg aga gac gcc cgg aaa cac gca gtg gag gtg<br>His Gly Gln Ala Glu Leu Arg Asp Ala Arg Lys His Ala Val Glu Val<br>               245                250               255 | | 768 |
| act ctg gat cca gag acg gct cac ccg aag ctc tgc gtt tct gat ctg<br>Thr Leu Asp Pro Glu Thr Ala His Pro Lys Leu Cys Val Ser Asp Leu<br>           260                265               270 | | 816 |
| aaa act gta acc cat aga aaa gct ccc cag gag gtg cct cac tct gag<br>Lys Thr Val Thr His Arg Lys Ala Pro Gln Glu Val Pro His Ser Glu<br>             275                280               285 | | 864 |
| aag aga ttt aca agg aag agt gtg gct tct cag ggt ttc caa gca<br>Lys Arg Phe Thr Arg Lys Ser Val Val Ala Ser Gln Gly Phe Gln Ala<br>           290                295               300 | | 912 |
| ggg aaa cat tac tgg gag gtg gac gtg gga caa aat gta ggg tgg tat<br>Gly Lys His Tyr Trp Glu Val Asp Val Gly Gln Asn Val Gly Trp Tyr<br>305                    310               315              320 | | 960 |
| gtg gga gtg tgt cgg gat gac gta gac agg ggg aag aac aat gtg act<br>Val Gly Val Cys Arg Asp Asp Val Asp Arg Gly Lys Asn Asn Val Thr<br>               325                330               335 | | 1008 |
| ttg tct ccc aac aat ggg tat tgg gtc ctc aga ctg aca aca gaa cat<br>Leu Ser Pro Asn Asn Gly Tyr Trp Val Leu Arg Leu Thr Thr Glu His<br>           340                345               350 | | 1056 |

-continued

| | | | | | | | | | | | | | | |
|---|---|---|---|---|---|---|---|---|---|---|---|---|---|---|
| ttg | tat | ttc | aca | ttc | aat | ccc | cat | ttt | atc | agc | ctc | ccc | ccc | agc | acc |
| Leu | Tyr | Phe | Thr | Phe | Asn | Pro | His | Phe | Ile | Ser | Leu | Pro | Pro | Ser | Thr |
| | | | 355 | | | | 360 | | | | | 365 | | | |

1104 cct cct aca cga gta ggg gtc ttc ctg gac tat gag ggt ggg acc atc   1152
Pro Pro Thr Arg Val Gly Val Phe Leu Asp Tyr Glu Gly Gly Thr Ile
        370             375                 380 tcc ttc ttc aat aca aat gac cag tcc ctt att tat acc ctg ctg aca   1200
Ser Phe Phe Asn Thr Asn Asp Gln Ser Leu Ile Tyr Thr Leu Leu Thr
385                 390                 395                 400 tgt cag ttt gaa ggc ttg ttg aga ccc tat atc cag cat gcg atg tat   1248
Cys Gln Phe Glu Gly Leu Leu Arg Pro Tyr Ile Gln His Ala Met Tyr
                405                 410                 415 gac gag gaa aag ggg act ccc ata ttc ata tgt cca gtg tcc tgg gga   1296
Asp Glu Glu Lys Gly Thr Pro Ile Phe Ile Cys Pro Val Ser Trp Gly
            420                 425                 430 tga   1299

<210> SEQ ID NO 9
<211> LENGTH: 432
<212> TYPE: PRT
<213> ORGANISM: Homo sapiens

<400> SEQUENCE: 9

Met Ala Phe Val Leu Ile Leu Val Leu Ser Phe Tyr Glu Leu Val Ser
1               5                   10                  15

Gly Gln Trp Gln Val Thr Gly Pro Gly Lys Phe Val Gln Ala Leu Val
            20                  25                  30

Gly Glu Asp Ala Val Phe Ser Cys Ser Leu Phe Pro Glu Thr Ser Ala
        35                  40                  45

Glu Ala Met Glu Val Arg Phe Phe Arg Asn Gln Phe His Ala Val Val
    50                  55                  60

His Leu Tyr Arg Asp Gly Glu Asp Trp Glu Ser Lys Gln Met Pro Gln
65                  70                  75                  80

Tyr Arg Gly Arg Thr Glu Phe Val Lys Asp Ser Ile Ala Gly Gly Arg
                85                  90                  95

Val Ser Leu Arg Leu Lys Asn Ile Thr Pro Ser Asp Ile Gly Leu Tyr
            100                 105                 110

Gly Cys Trp Phe Ser Ser Gln Ile Tyr Asp Glu Glu Ala Thr Trp Glu
        115                 120                 125

Leu Arg Val Ala Ala Leu Gly Ser Leu Pro Leu Ile Ser Ile Val Gly
    130                 135                 140

Tyr Val Asp Gly Gly Ile Gln Leu Leu Cys Leu Ser Ser Phe Gln Pro
145                 150                 155                 160

Ser Pro Trp Arg Leu Ala Ser Ile Leu Leu Gly Leu Leu Cys Gly Ala
                165                 170                 175

Leu Cys Gly Val Val Met Gly Met Ile Ile Val Phe Phe Lys Ser Lys
            180                 185                 190

Gly Lys Ile Gln Ala Glu Leu Gly Met Cys His Val Leu Ser Leu Pro
        195                 200                 205

His Met Val Leu Pro Gly Pro Ser Leu Ile His Ser Leu Ser Leu Trp
    210                 215                 220

Thr Thr Leu Ala Ala Gly Trp Thr Gly Ser Thr Asp Trp Arg Arg Lys
225                 230                 235                 240

His Gly Gln Ala Glu Leu Arg Asp Ala Arg Lys His Ala Val Glu Val
                245                 250                 255

```
Thr Leu Asp Pro Glu Thr Ala His Pro Lys Leu Cys Val Ser Asp Leu
            260                 265                 270
Lys Thr Val Thr His Arg Lys Ala Pro Gln Glu Val Pro His Ser Glu
        275                 280                 285
Lys Arg Phe Thr Arg Lys Ser Val Ala Ser Gln Gly Phe Gln Ala
    290                 295                 300
Gly Lys His Tyr Trp Glu Val Asp Val Gly Gln Asn Val Gly Trp Tyr
305                 310                 315                 320
Val Gly Val Cys Arg Asp Val Asp Arg Gly Lys Asn Asn Val Thr
                325                 330                 335
Leu Ser Pro Asn Asn Gly Tyr Trp Val Leu Arg Leu Thr Thr Glu His
            340                 345                 350
Leu Tyr Phe Thr Phe Asn Pro His Phe Ile Ser Leu Pro Pro Ser Thr
        355                 360                 365
Pro Pro Thr Arg Val Gly Val Phe Leu Asp Tyr Glu Gly Gly Thr Ile
    370                 375                 380
Ser Phe Phe Asn Thr Asn Asp Gln Ser Leu Ile Tyr Thr Leu Thr
385                 390                 395                 400
Cys Gln Phe Glu Gly Leu Leu Arg Pro Tyr Ile Gln His Ala Met Tyr
                405                 410                 415
Asp Glu Glu Lys Gly Thr Pro Ile Phe Ile Cys Pro Val Ser Trp Gly
            420                 425                 430

<210> SEQ ID NO 10
<211> LENGTH: 5
<212> TYPE: PRT
<213> ORGANISM: Artificial sequence
<220> FEATURE:
<223> OTHER INFORMATION: Linker

<400> SEQUENCE: 10

Gly Gly Gly Gly Ser
1               5

<210> SEQ ID NO 11
<211> LENGTH: 6
<212> TYPE: PRT
<213> ORGANISM: Artificial sequence
<220> FEATURE:
<223> OTHER INFORMATION: Linker

<400> SEQUENCE: 11

Gly Gly Gly Gly Ser Asn
1               5

<210> SEQ ID NO 12
<211> LENGTH: 12
<212> TYPE: PRT
<213> ORGANISM: Artificial Sequence
<220> FEATURE:
<223> OTHER INFORMATION: Linker

<400> SEQUENCE: 12

Gly Lys Ser Ser Gly Ser Gly Ser Glu Ser Lys Ser
1               5                   10

<210> SEQ ID NO 13
<211> LENGTH: 14
<212> TYPE: PRT
<213> ORGANISM: Artificial sequence
<220> FEATURE:
<223> OTHER INFORMATION: Linker
```

```
<400> SEQUENCE: 13

Gly Ser Thr Ser Gly Ser Gly Lys Ser Ser Glu Gly Lys Gly
1               5                   10

<210> SEQ ID NO 14
<211> LENGTH: 18
<212> TYPE: PRT
<213> ORGANISM: Artificial sequence
<220> FEATURE:
<223> OTHER INFORMATION: Linker

<400> SEQUENCE: 14

Gly Ser Thr Ser Gly Ser Gly Lys Ser Ser Glu Gly Ser Gly Ser Thr
1               5                   10                  15

Lys Gly

<210> SEQ ID NO 15
<211> LENGTH: 14
<212> TYPE: PRT
<213> ORGANISM: Artificial sequence
<220> FEATURE:
<223> OTHER INFORMATION: Linker

<400> SEQUENCE: 15

Gly Ser Thr Ser Gly Ser Gly Lys Ser Ser Glu Gly Lys Gly
1               5                   10

<210> SEQ ID NO 16
<211> LENGTH: 18
<212> TYPE: PRT
<213> ORGANISM: Artificial sequence
<220> FEATURE:
<223> OTHER INFORMATION: Linker

<400> SEQUENCE: 16

Gly Ser Thr Ser Gly Ser Gly Lys Pro Gly Ser Gly Glu Gly Ser Thr
1               5                   10                  15

Lys Gly

<210> SEQ ID NO 17
<211> LENGTH: 14
<212> TYPE: PRT
<213> ORGANISM: Artificial sequence
<220> FEATURE:
<223> OTHER INFORMATION: Linker

<400> SEQUENCE: 17

Glu Gly Lys Ser Ser Gly Ser Gly Ser Glu Ser Lys Glu Phe
1               5                   10

<210> SEQ ID NO 18
<211> LENGTH: 15
<212> TYPE: PRT
<213> ORGANISM: Artificial sequence
<220> FEATURE:
<223> OTHER INFORMATION: Linker

<400> SEQUENCE: 18

Gly Gly Gly Gly Ser Gly Gly Gly Gly Ser Gly Gly Gly Gly Ser
1               5                   10                  15

<210> SEQ ID NO 19
<211> LENGTH: 500
<212> TYPE: PRT
<213> ORGANISM: Homo sapiens
```

<400> SEQUENCE: 19

```
Met Ala Leu Met Leu Ser Leu Val Leu Ser Leu Leu Lys Leu Gly Ser
1               5                   10                  15

Gly Gln Trp Gln Val Phe Gly Pro Asp Lys Pro Val Gln Ala Leu Val
            20                  25                  30

Gly Glu Asp Ala Ala Phe Ser Cys Phe Leu Ser Pro Lys Thr Asn Ala
        35                  40                  45

Glu Ala Met Glu Val Arg Phe Arg Gly Gln Phe Ser Ser Val Val
    50                  55                  60

His Leu Tyr Arg Asp Gly Lys Asp Gln Pro Phe Met Gln Met Pro Gln
65                  70                  75                  80

Tyr Gln Gly Arg Thr Lys Leu Val Lys Asp Ser Ile Ala Glu Gly Arg
                85                  90                  95

Ile Ser Leu Arg Leu Glu Asn Ile Thr Val Leu Asp Ala Gly Leu Tyr
            100                 105                 110

Gly Cys Arg Ile Ser Ser Gln Ser Tyr Tyr Gln Lys Ala Ile Trp Glu
        115                 120                 125

Leu Gln Val Ser Ala Leu Gly Ser Val Pro Leu Ile Ser Ile Thr Gly
    130                 135                 140

Tyr Val Asp Arg Asp Ile Gln Leu Leu Cys Gln Ser Ser Gly Trp Phe
145                 150                 155                 160

Pro Arg Pro Thr Ala Lys Trp Lys Gly Pro Gln Gly Gln Asp Leu Ser
                165                 170                 175

Thr Asp Ser Arg Thr Asn Arg Asp Met His Gly Leu Phe Asp Val Glu
            180                 185                 190

Ile Ser Leu Thr Val Gln Glu Asn Ala Gly Ser Ile Ser Cys Ser Met
        195                 200                 205

Arg His Ala His Leu Ser Arg Glu Val Glu Ser Arg Val Gln Ile Gly
    210                 215                 220

Asp Thr Phe Phe Glu Pro Ile Ser Trp His Leu Ala Thr Lys Val Leu
225                 230                 235                 240

Gly Ile Leu Cys Cys Gly Leu Phe Phe Gly Ile Val Gly Leu Lys Ile
                245                 250                 255

Phe Phe Ser Lys Phe Gln Trp Lys Ile Gln Ala Glu Leu Asp Trp Arg
            260                 265                 270

Arg Lys His Gly Gln Ala Glu Leu Arg Asp Ala Arg Lys His Ala Val
        275                 280                 285

Glu Val Thr Leu Asp Pro Glu Thr Ala His Pro Lys Leu Cys Val Ser
    290                 295                 300

Asp Leu Lys Thr Val Thr His Arg Lys Ala Pro Gln Glu Val Pro His
305                 310                 315                 320

Ser Glu Lys Arg Phe Thr Arg Lys Ser Val Val Ala Ser Gln Ser Phe
                325                 330                 335

Gln Ala Gly Lys His Tyr Trp Glu Val Asp Gly Gly His Asn Lys Arg
            340                 345                 350

Trp Arg Val Gly Val Cys Arg Asp Asp Val Asp Arg Lys Glu Tyr
        355                 360                 365

Val Thr Leu Ser Pro Asp His Gly Tyr Trp Val Leu Arg Leu Asn Gly
    370                 375                 380

Glu His Leu Tyr Phe Thr Leu Asn Pro Arg Phe Ile Ser Val Phe Pro
385                 390                 395                 400

Arg Thr Pro Pro Thr Lys Ile Gly Val Phe Leu Asp Tyr Glu Cys Gly
                405                 410                 415
```

```
Thr Ile Ser Phe Phe Asn Ile Asn Asp Gln Ser Leu Ile Tyr Thr Leu
            420                 425                 430

Thr Cys Arg Phe Glu Gly Leu Leu Arg Pro Tyr Ile Glu Tyr Pro Ser
            435                 440                 445

Tyr Asn Glu Gln Asn Gly Thr Pro Ile Val Ile Cys Pro Val Thr Gln
            450                 455                 460

Glu Ser Glu Lys Glu Ala Ser Trp Gln Arg Ala Ser Ala Ile Pro Glu
465                 470                 475                 480

Thr Ser Asn Ser Glu Ser Ser Gln Ala Thr Thr Pro Phe Leu Pro
                485                 490                 495

Arg Gly Glu Met
            500

<210> SEQ ID NO 20
<211> LENGTH: 535
<212> TYPE: PRT
<213> ORGANISM: Homo sapiens

<400> SEQUENCE: 20

Met Val Asp Leu Ser Val Ser Pro Asp Ser Leu Lys Pro Val Ser Leu
1               5                   10                  15

Thr Ser Ser Leu Val Phe Leu Met His Leu Leu Leu Gln Pro Gly
            20                  25                  30

Glu Pro Ser Ser Glu Val Lys Val Leu Gly Pro Glu Tyr Pro Ile Leu
            35                  40                  45

Ala Leu Val Gly Glu Glu Val Glu Phe Pro Cys His Leu Trp Pro Gln
50                  55                  60

Leu Asp Ala Gln Gln Met Glu Ile Arg Trp Phe Arg Ser Gln Thr Phe
65                  70                  75                  80

Asn Val Val His Leu Tyr Gln Glu Gln Gln Leu Pro Gly Arg Gln
            85                  90                  95

Met Pro Ala Phe Arg Asn Arg Thr Lys Leu Val Lys Asp Asp Ile Ala
            100                 105                 110

Tyr Gly Ser Val Val Leu Gln Leu His Ser Ile Ile Pro Ser Asp Lys
            115                 120                 125

Gly Thr Tyr Gly Cys Arg Phe His Ser Asp Asn Phe Ser Gly Glu Ala
            130                 135                 140

Leu Trp Glu Leu Glu Val Ala Gly Leu Gly Ser Asp Pro His Leu Ser
145                 150                 155                 160

Leu Glu Gly Phe Lys Glu Gly Gly Ile Gln Leu Arg Leu Arg Ser Ser
            165                 170                 175

Gly Trp Tyr Pro Lys Pro Lys Val Gln Trp Arg Asp His Gln Gly Gln
            180                 185                 190

Cys Leu Pro Pro Glu Phe Glu Ala Ile Val Trp Asp Ala Gln Asp Leu
            195                 200                 205

Phe Ser Leu Glu Thr Ser Val Val Val Arg Ala Gly Ala Leu Ser Asn
            210                 215                 220

Val Ser Val Ser Ile Gln Asn Leu Leu Leu Ser Gln Lys Lys Glu Leu
225                 230                 235                 240

Val Val Gln Ile Ala Asp Val Phe Val Pro Gly Ala Ser Ala Trp Lys
            245                 250                 255

Ser Ala Phe Val Ala Thr Leu Pro Leu Leu Val Leu Ala Ala Leu
            260                 265                 270

Ala Leu Gly Val Leu Arg Lys Gln Arg Arg Ser Arg Glu Lys Leu Arg
            275                 280                 285
```

```
Lys Gln Ala Glu Lys Arg Gln Glu Lys Leu Thr Ala Glu Leu Glu Lys
    290                 295                 300

Leu Gln Thr Glu Leu Asp Trp Arg Arg Ala Glu Gly Gln Ala Glu Trp
305                 310                 315                 320

Arg Ala Ala Gln Lys Tyr Ala Val Asp Val Thr Leu Asp Pro Ala Ser
                325                 330                 335

Ala His Pro Ser Leu Glu Val Ser Glu Asp Gly Lys Ser Val Ser Ser
                340                 345                 350

Arg Gly Ala Pro Pro Gly Pro Ala Pro Gly His Pro Gln Arg Phe Ser
                355                 360                 365

Glu Gln Thr Cys Ala Leu Ser Leu Glu Arg Phe Ser Ala Gly Arg His
                370                 375                 380

Tyr Trp Glu Val His Val Gly Arg Arg Ser Arg Trp Phe Leu Gly Ala
385                 390                 395                 400

Cys Leu Ala Ala Val Pro Arg Ala Gly Pro Ala Arg Leu Ser Pro Ala
                405                 410                 415

Ala Gly Tyr Trp Val Leu Gly Leu Trp Asn Gly Cys Glu Tyr Phe Val
                420                 425                 430

Leu Ala Pro His Arg Val Ala Leu Thr Leu Arg Val Pro Pro Arg Arg
                435                 440                 445

Leu Gly Val Phe Leu Asp Tyr Glu Ala Gly Glu Leu Ser Phe Phe Asn
                450                 455                 460

Val Ser Asp Gly Ser His Ile Phe Thr Phe His Asp Thr Phe Ser Gly
465                 470                 475                 480

Ala Leu Cys Ala Tyr Phe Arg Pro Arg Ala His Asp Gly Gly Glu His
                485                 490                 495

Pro Asp Pro Leu Thr Ile Cys Pro Leu Pro Val Arg Gly Thr Gly Val
                500                 505                 510

Pro Glu Glu Asn Asp Ser Asp Thr Trp Leu Gln Pro Tyr Glu Pro Ala
                515                 520                 525

Asp Pro Ala Leu Asp Trp Trp
                530                 535

<210> SEQ ID NO 21
<211> LENGTH: 475
<212> TYPE: PRT
<213> ORGANISM: Homo sapiens

<400> SEQUENCE: 21

Met Glu Met Ala Ser Ser Ala Gly Ser Trp Leu Ser Gly Cys Leu Ile
1               5                   10                  15

Pro Leu Val Phe Leu Arg Leu Ser Val His Val Ser Gly His Ala Gly
                20                  25                  30

Asp Ala Gly Lys Phe His Val Ala Leu Leu Gly Gly Thr Ala Glu Leu
                35                  40                  45

Leu Cys Pro Leu Ser Leu Trp Pro Gly Thr Val Pro Lys Glu Val Arg
            50                  55                  60

Trp Leu Arg Ser Pro Phe Pro Gln Arg Ser Gln Ala Val His Ile Phe
65              70                  75                  80

Arg Asp Gly Lys Asp Gln Asp Glu Asp Leu Met Pro Glu Tyr Lys Gly
                85                  90                  95

Arg Thr Val Leu Val Arg Asp Ala Gln Glu Gly Ser Val Thr Leu Gln
                100                 105                 110

Ile Leu Asp Val Arg Leu Glu Asp Gln Gly Ser Tyr Arg Cys Leu Ile
                115                 120                 125
```

Gln Val Gly Asn Leu Ser Lys Glu Asp Thr Val Ile Leu Gln Val Ala
130                 135                 140

Ala Pro Ser Val Gly Ser Leu Ser Pro Ser Ala Val Ala Leu Ala Val
145                 150                 155                 160

Ile Leu Pro Val Leu Val Leu Ile Met Val Cys Leu Cys Leu Ile
            165                 170                 175

Trp Lys Gln Arg Arg Ala Lys Glu Lys Leu Leu Tyr Glu His Val Thr
            180                 185                 190

Glu Val Asp Asn Leu Leu Ser Asp His Ala Lys Glu Lys Gly Lys Leu
            195                 200                 205

His Lys Ala Val Lys Lys Leu Arg Ser Glu Leu Lys Leu Lys Arg Ala
210                 215                 220

Ala Ala Asn Ser Gly Trp Arg Arg Ala Arg Leu His Phe Val Ala Val
225                 230                 235                 240

Thr Leu Asp Pro Asp Thr Ala His Pro Lys Leu Ile Leu Ser Glu Asp
            245                 250                 255

Gln Arg Cys Val Arg Leu Gly Asp Arg Arg Gln Pro Val Pro Asp Asn
            260                 265                 270

Pro Gln Arg Phe Asp Phe Val Val Ser Ile Leu Gly Ser Glu Tyr Phe
            275                 280                 285

Thr Thr Gly Cys His Tyr Trp Glu Val Tyr Val Gly Asp Lys Thr Lys
290                 295                 300

Trp Ile Leu Gly Val Cys Ser Glu Ser Val Ser Arg Lys Gly Lys Val
305                 310                 315                 320

Thr Ala Ser Pro Ala Asn Gly His Trp Leu Leu Arg Gln Ser Arg Gly
            325                 330                 335

Asn Glu Tyr Glu Ala Leu Thr Ser Pro Gln Thr Ser Phe Arg Leu Lys
            340                 345                 350

Glu Pro Pro Arg Cys Val Gly Ile Phe Leu Asp Tyr Glu Ala Gly Val
            355                 360                 365

Ile Ser Phe Tyr Asn Val Thr Asn Lys Ser His Ile Phe Thr Phe Thr
370                 375                 380

His Asn Phe Ser Gly Pro Leu Arg Pro Phe Phe Glu Pro Cys Leu His
385                 390                 395                 400

Asp Gly Gly Lys Asn Thr Ala Pro Leu Val Ile Cys Ser Glu Leu His
            405                 410                 415

Lys Ser Glu Glu Ser Ile Val Pro Arg Pro Glu Gly Lys Gly His Ala
            420                 425                 430

Asn Gly Asp Val Ser Leu Lys Val Asn Ser Ser Leu Leu Pro Pro Lys
            435                 440                 445

Ala Pro Glu Leu Lys Asp Ile Ile Leu Ser Leu Pro Pro Asp Leu Gly
450                 455                 460

Pro Ala Leu Gln Glu Leu Lys Ala Pro Ser Phe
465                 470                 475

<210> SEQ ID NO 22
<211> LENGTH: 252
<212> TYPE: PRT
<213> ORGANISM: Homo sapiens

<400> SEQUENCE: 22

Met Ala Ser Leu Ser Arg Pro Ser Leu Pro Ser Cys Leu Cys Ser Phe
1               5                   10                  15

Leu Leu Leu Leu Leu Leu Gln Val Ser Ser Ser Tyr Ala Gly Gln Phe
            20                  25                  30

```
Arg Val Ile Gly Pro Arg His Pro Ile Arg Ala Leu Val Gly Asp Glu
             35                  40                  45

Val Glu Leu Pro Cys Arg Ile Ser Pro Gly Lys Asn Ala Thr Gly Met
 50                  55                  60

Glu Val Gly Trp Tyr Arg Pro Pro Phe Ser Arg Val Val His Leu Tyr
 65                  70                  75                  80

Arg Asn Gly Lys Asp Gln Asp Gly Asp Gln Ala Pro Glu Tyr Arg Gly
                 85                  90                  95

Arg Thr Glu Leu Leu Lys Asp Ala Ile Gly Glu Gly Lys Val Thr Leu
            100                 105                 110

Arg Ile Arg Asn Val Arg Phe Ser Asp Glu Gly Gly Phe Thr Cys Phe
            115                 120                 125

Phe Arg Asp His Ser Tyr Gln Glu Glu Ala Ala Met Glu Leu Lys Val
130                 135                 140

Glu Asp Pro Phe Tyr Trp Val Ser Pro Gly Val Leu Val Leu Leu Ala
145                 150                 155                 160

Val Leu Pro Val Leu Leu Gln Ile Thr Val Gly Leu Val Phe Leu
            165                 170                 175

Cys Leu Gln Tyr Arg Leu Arg Gly Lys Leu Arg Ala Glu Ile Glu Asn
            180                 185                 190

Leu His Arg Thr Phe Asp Pro His Phe Leu Arg Val Pro Cys Trp Lys
            195                 200                 205

Ile Thr Leu Phe Val Ile Val Pro Val Leu Gly Pro Leu Val Ala Leu
            210                 215                 220

Ile Ile Cys Tyr Asn Trp Leu His Arg Arg Leu Ala Gly Gln Phe Leu
225                 230                 235                 240

Glu Glu Leu Leu Phe His Leu Glu Ala Leu Ser Gly
            245                 250

<210> SEQ ID NO 23
<211> LENGTH: 282
<212> TYPE: PRT
<213> ORGANISM: Homo sapiens

<400> SEQUENCE: 23

Tyr Ala Glu Ala Thr Leu Val Val Arg Asn Ala Ser Ala Glu Ser Val
 1               5                  10                  15

Ser Cys Leu Val His Asn Pro Val Leu Thr Glu Glu Lys Gly Ser Val
             20                  25                  30

Ile Ser Leu Pro Glu Lys Leu Gln Thr Glu Leu Ala Ser Leu Lys Val
             35                  40                  45

Asn Gly Pro Ser Gln Pro Ile Leu Val Arg Val Gly Glu Asp Ile Gln
 50                  55                  60

Leu Thr Cys Tyr Leu Ser Pro Lys Ala Asn Ala Gln Ser Met Glu Val
 65                  70                  75                  80

Arg Trp Asp Arg Ser His Arg Tyr Pro Ala Val His Val Tyr Met Asp
                 85                  90                  95

Gly Asp His Val Ala Gly Glu Gln Met Ala Glu Tyr Arg Gly Arg Thr
            100                 105                 110

Val Leu Val Ser Asp Ala Ile Asp Glu Gly Arg Leu Thr Leu Gln Ile
            115                 120                 125

Leu Ser Ala Arg Pro Ser Asp Asp Gly Gln Tyr Arg Cys Leu Phe Glu
130                 135                 140

Lys Asp Asp Val Tyr Gln Glu Ala Ser Leu Asp Leu Lys Val Val Gly
145                 150                 155                 160
```

```
Leu Gly Ser Ser Pro Leu Ile Thr Val Glu Gly Gln Glu Asp Gly Glu
                165                 170                 175

Met Gln Pro Met Cys Ser Ser Asp Gly Trp Phe Pro Gln Pro His Val
            180                 185                 190

Pro Trp Arg Asp Met Glu Gly Lys Thr Ile Pro Ser Ser Ser Gln Ala
        195                 200                 205

Leu Thr Gln Gly Ser His Gly Leu Phe His Val Gln Thr Leu Leu Arg
    210                 215                 220

Val Thr Asn Ile Ser Ala Val Asp Val Thr Cys Ser Ile Ser Ile Pro
225                 230                 235                 240

Phe Leu Gly Glu Glu Lys Ile Ala Thr Phe Ser Leu Ser Glu Ser Arg
            245                 250                 255

Met Thr Phe Leu Trp Lys Thr Leu Leu Val Trp Gly Leu Leu Leu Ala
            260                 265                 270

Val Ala Val Gly Leu Pro Arg Lys Arg Ser
            275                 280
```

BTNL3 PROTEINS, NUCLEIC ACIDS AND ANTIBODIES AND USES THEREOF

CROSS-REFERENCE TO RELATED APPLICATIONS

This application is a divisional of pending U.S. application Ser. No. 14/407,904, filed on Dec. 12, 2014; which is a 371 of International Patent Application No. PCT/US13/51097, filed Jul. 18, 2013; which claims the benefit of U.S. Provisional Application No. 61/673,639 filed Jul. 19, 2012, which is incorporated by reference herein.

FIELD

This invention relates to a butyrophilin-like protein and fragments, variants, and derivatives thereof, nucleic acids encoding such proteins, antibodies that bind to these proteins, and agonists and antagonists of these proteins. Pharmaceutical compositions containing such molecules and uses for such molecules or compositions containing them are also contemplated.

BACKGROUND

Modulation of an immune or inflammatory response may be valuable in various therapeutic settings. Downmodulation of an immune or inflammatory response may be desirable in treatments for various kinds of autoimmune or inflammatory diseases. Enhancement of any immune response may be valuable to, for example, amplify a response to a particular antigen, such as an antigen contained in a vaccine and/or an antigen preferentially expressed on a cancer cell, a cell mediating a fibrotic disease, or a pathogen. Thus, molecules capable of modulating an immune or inflammatory response are potentially of therapeutic value in a variety of pathological settings. The present invention provides therapeutic agents to diagnose and treat diseases characterized by inappropriate, inadequate, and/or abnormal inflammation and/or immune responses. Some of these agents can stimulate an immune response. Others can inhibit inflammation and/or immune responses.

SUMMARY

The invention provides BTNL3 proteins and variants thereof, nucleic acids encoding them, and antibodies that bind to them. More specifically, the BTNL3 proteins described herein are multimeric proteins and or fusion proteins that can be isolated and/or soluble proteins. BNTL3 proteins can be attached to a surface and/or expressed on the surface of a cell. Also provided are uses for BTNL3 proteins and for antagonists and agonists of BTNL3, including anti-BTNL3 antibodies.

In one embodiment, the invention encompasses an isolated multimeric BTNL3 protein, optionally a soluble protein, or a BTNL3 protein attached to a surface such as a microbead or expressed on a cell surface comprising (a) a polypeptide having an amino acid sequence at least 90%, 95%, 96%, 97%, 98%, 99%, or 100% identical to amino acids 18-236 of SEQ ID NO:2 or to amino acids 18-166 of SEQ ID NO:9 and (b) a second polypeptide having an amino acid sequence at least 90%, 95%, 96%, 97%, 98%, 99%, or 100% identical to amino acids 18-236 of SEQ ID NO:2 or to amino acids 18-166 of SEQ ID NO:9, wherein the alignment window of the amino acid sequences of the polypeptides of (a) and (b) with amino acids 18-236 of SEQ ID NO:2 or with amino acids 18-166 of SEQ ID NO:9 is at least 50, 60, 70, 80, or 100 amino acids long, wherein the BTNL3 protein is at least a dimer, a trimer, or a tetramer, wherein the BTNL3 protein has been produced by a non-human host cell, and wherein the multimeric BTNL3 protein can inhibit the proliferation of a T cell stimulated by an immobilized anti-CD3 antibody. In a slightly different embodiment, the invention provides isolated multimeric BTNL3 protein, optionally a soluble protein, comprising (a) a polypeptide having an amino acid sequence at least 90% identical to amino acids 18-236 of SEQ ID NO:2 or to amino acids 18-166 of SEQ ID NO:9, and (b) a second polypeptide having an amino acid sequence at least 90% identical to amino acids 18-236 of SEQ ID NO:2 or to amino acids 18-166 of SEQ ID NO:9, wherein the alignment window of the amino acid sequences of the polypeptides of (a) and (b) with amino acids 18-236 of SEQ ID NO:2 or with amino acids 18-166 of SEQ ID NO:9 is at least 50, 60, 70, 80, or 100 amino acids long, wherein the BTNL3 protein has a molecular weight that is at least about two, three, or four times as large as that of a monomeric polypeptide of (a) and/or at least about five, six, seven, eight, nine, ten, eleven, twelve, thirteen, fourteen, fifteen, or sixteen times as large as that of a monomeric polypeptide of (a), wherein the BTNL3 protein has been produced by a non-human host cell, and wherein the multimeric BTNL3 protein can inhibit the proliferation of a T cell stimulated by an immobilized anti-CD3 antibody. Alternatively or in addition in either of these embodiments, the polypeptides of (a) and (b) can comprise a sequence having not more than 20, 15, 12, 10, 8, or 5 insertions, deletions, or substitutions of a single amino acid relative to amino acids 18-236 of SEQ ID NO:2 or amino acids 18-166 of SEQ ID NO:9. In some embodiments the multimeric BTNL3 protein can be no more than three, four, five, six, seven, eight, nine, ten, eleven, twelve, thirteen, fourteen, fifteen, or sixteen times as large as that of a monomeric polypeptide of (a). The multimeric BTNL3 protein in either of these embodiments can also be at least a dimer, a trimer, a tetramer, a pentamer, a hexamer, a heptamer, an octomer, a nonamer, a decamer, and/or a higher order multimer, which also means that the multimeric BTNL3 protein can be a dimer, a trimer, tetramer, a pentamer, a hexamer, a heptamer, an octomer, a nonamer, a decamer, and/or a higher order multimer. In some embodiments, the multimeric BTNL3 protein can be no more than a trimer, a tetramer, a pentamer, a hexamer, a heptamer, an octomer, a nonamer, or a decamer. The multimeric BTNL3 protein can comprise the amino acid sequence from amino acid 18, 19, 20, 21, 22, or 23 to 234, 235, 236, 237, or 238 of SEQ ID NO:2 or the amino acid sequence from amino acid 18, 19, 20, 21, 22, or 23 to 164, 165, 166, 167, or 168 of SEQ ID NO:9. In some embodiments, the amino acid sequences of the polypeptides of (a) and (b) do not comprise amino acids 237 to 259 of SEQ ID NO:2 or amino acids 167 to 189 of SEQ ID NO:9, and in some embodiments these amino acid sequences may comprise an additional amino acid sequence, which is, for example, an amino acid sequence of an Fc polypeptide. Such Fc polypeptides can comprise (i) the amino acid sequence of a native human Fc region or (ii) an amino acid sequence that is substantially similar to that of the native human Fc region having not more than 15, not more than 10, or not more than 5 insertions, deletions, or substitutions of a single amino acid relative to the amino acid sequence of a native human Fc region. The native human Fc may be of the IgG, including IgG1, IgG2, IgG3, or IgG4, IgA, IgD, IgM, or IgE isotype. The multimeric BTNL3 protein can be a homodimer, homotrimer, homotetramer, a homopentamer, a homohexamer, a homoheptamer, a homooctamer, a homononamer, a homodecamer, a higher order homomultimer, a heteromultimer, or a mixture of species. The multimeric BTNL3 protein can have a molecular weight that is: approximately 4 times as large as the molecular weight of the polypeptide of (a) or (b); approximately the sum of two times the molecular weight of the polypeptide of (a) plus two times the molecular weight of the polypeptide of (b); approximately the sum of three times the molecular weight of the polypeptide of (a) plus the molecular weight of the polypeptide of (b); or approximately the sum of the molecular weight of the polypeptide of (a) plus three times the molecular weight of the polypeptide of (b). Nucleic acids encoding such multimeric BTNL3 proteins are also provided, as well as vectors comprising these nucleic acids and host cells containing the vectors and/or the nucleic acids.

In another embodiment, the invention provides a BTNL3 fusion protein comprising (a) a first polypeptide comprising an amino acid sequence at least 90%, 95%, 96%, 97%, 98%, 99%, or 100% identical to amino acids 18-236 of SEQ ID NO:2 or to amino acids 18-166 of SEQ ID NO:9, wherein the alignment window of the amino acid sequence of the BTNL3 fusion protein with amino acids 18-236 is SEQ ID NO:2 or with amino acids 18 to 166 of SEQ ID NO:9 is at least 80 amino acids long, and (b) a second polypeptide that has a different amino acid sequence from that of the first polypeptide and does not comprise a fragment of the sequence from amino acid 237 to 466 of SEQ ID NO:2 that is at least 20 amino acids long, wherein the BTNL3 fusion protein can inhibit the proliferation of a T cell stimulated by an immobilized anti-CD3 antibody. The fusion protein can be an isolated and/or a soluble protein. The second polypeptide can be an Fc polypeptide, wherein the Fc polypeptide has an amino acid sequence that is identical or substantially similar to an amino acid sequence of a native human Fc region and contains not more than 5, 10, 15, or 20 insertions, deletions, or substitutions of a single amino acid relative to the native human Fc region. The native human Fc region can be of the IgG, including IgG1, IgG2, IgG3, or IgG4, IgA, IgD, IgE, or IgM isotype. The BTNL3 fusion protein can comprise amino acids 18-236 of SEQ ID NO:2 or amino acids 18-166 of SEQ ID NO:9. The BTNL3 fusion protein can comprise an amino acid sequence that is substantially similar to SEQ ID NO:7, wherein the amino acid sequence comprises not more than 5, 10, 15, or 20 insertions, deletions, or substitutions of a single amino acid relative to SEQ ID NO:7, and/or the BTNL3 fusion protein can comprise SEQ ID NO:7. The BTNL3 fusion protein can be at least a dimer, a trimer, a tetramer, a pentamer, a hexamer, a heptamer, an octamer, a nonamer, or a decamer. In some embodiments the BTNL3 fusion protein can be not more than a dimer, a trimer, a tetramer, a pentamer, a hexamer, a heptamer, an octamer, a nonamer, or a decamer. The BTNL3 fusion protein can comprise a linker. In some embodiments the BTNL3 fusion protein does not comprise a linker. Such a BTNL3 fusion protein can be a multimer, wherein the multimer can have a molecular weight at least about four, five, six, seven, eight, nine, ten, eleven, twelve, thirteen, fourteen, fifteen, or sixteen times as large as that of the monomeric BTNL3 fusion protein. In another aspect, some such multimers can have a molecular weight that is no more than about four, five, six, seven, eight, nine, ten, eleven, twelve, thirteen, fourteen, fifteen, or sixteen times as large as that of the monomeric BTNL3 fusion protein. Nucleic acids encoding such BTNL3 fusion proteins are also provided, as well as vectors comprising these nucleic acids and host cells containing the vectors and/or the nucleic acids.

In another embodiment, the invention provides a BTNL3 protein, optionally a soluble protein, or a BTNL3 protein attached to a surface such as a microbead or expressed on a cell surface, comprising the amino acid sequence of a fragment of SEQ ID NO:2 extending from about position 25-131 of SEQ ID NO:2, 6, or 9, or a variant thereof comprising no more than 5 or 10 insertions, deletions, or substitutions of a single amino acid relative to amino acids 25-131 of SEQ ID NO:2, 6, or 9, wherein the BTNL3 protein does not also comprise the amino acid sequence of a fragment of SEQ ID NO:2 extending from about position 132 to 236 of SEQ ID NO:2 or a variant thereof comprising no more than 20, 15, 10, 10, or 5 insertions, deletions, or substitutions of a single amino acid relative to amino acids 132 to 236 of SEQ ID NO:2, and wherein the BTNL3 protein can inhibit the proliferation of a T cell stimulated by an immobilized anti-CD3 antibody. The BTNL3 protein can be made in a non-human or mammalian host cell. The BTNL3 protein or a BTNL3 protein attached to a surface such as a microbead or expressed on a cell surface may comprise no more than 5 insertions, deletions or substitutions of a single amino acid relative to amino acids 25 to 131 of SEQ ID NO:2, 6, or 9. Or, in another aspect, the amino acid sequence of the soluble BTNL3 protein can be at least 90%, 95%, 96%, 97%, 98%, 99%, or 100% identical to amino acids 25 to 131 of SEQ ID NO:2. The soluble BTNL3 protein or a BTNL3 protein attached to a surface such as a microbead or expressed on a cell surface can be at least a dimer, a trimer, a tetramer, a pentamer, a hexamer, a heptamer, an octamer, a nonamer, or a decamer. Such a BTNL3 protein or a BTNL3 protein attached to a surface such as a microbead or expressed on a cell surface can also be a dimer, a trimer, a tetramer, a pentamer, a hexamer, a heptamer, an octamer, a nonamer, a decamer, a higher order multimer, or a mixture of these species. In another aspect, the soluble BTNL3 protein or a BTNL3 protein attached to a surface such as a microbead or expressed on a cell surface may be no more than a trimer, a tetramer, a pentamer, a hexamer, a heptamer, an octamer, a nonamer, or a decamer. Such a soluble BTNL3 protein or a BTNL3 protein attached to a surface such as a microbead or expressed on a cell surface can be a multimer, wherein the multimer has a molecular weight at least about two, three, four, five, six, seven, eight, nine, ten, eleven, twelve, thirteen, fourteen, fifteen, or sixteen times as large as that of the monomeric soluble BTNL3 protein. In another aspect, such a soluble BTNL3 protein or a BTNL3 protein attached to a surface such as a microbead or expressed on a cell surface can be a multimer that has a molecular weight that is no more than about three, four, five, six, seven, eight, nine, ten, eleven, twelve, thirteen, fourteen, fifteen, or sixteen times as large as that of the monomeric soluble BTNL3 protein. Such a soluble BTNL3 protein or a BTNL3 protein attached to a surface such as a microbead or expressed on a cell surface can further comprise another polypeptide, such as, for example, an Fc fragment of an antibody and/or a linker. Nucleic acids encoding such soluble BTNL3 proteins are also provided, as well as vectors comprising these nucleic acids and host cells containing the vectors and/or the nucleic acids.

Alternatively, a BTNL3 protein, optionally a soluble protein, or a BTNL3 protein attached to a surface such as a microbead or expressed on a cell surface, can comprise the amino acid sequence of a fragment of SEQ ID NO:2 or 6 extending from about position 132 to 236 of SEQ ID NO:2 or 6, or a variant thereof, comprising no more than 20, 15, 10, or 5 insertions, deletions, or substitutions of a single amino acid relative to amino acids 132 to 236 of SEQ ID NO:2 or 6, wherein the BTNL3 protein does not also comprise the amino acid sequence of a fragment of SEQ ID NO:2 extending from position 25 to 131 of SEQ ID NO:2 or 6 or a variant thereof comprising no more than 10 insertions, deletions, or substitutions of a single amino acid relative to amino acids 25 to 131 of SEQ ID NO:2 or 6, and wherein the BTNL3 protein can inhibit the proliferation of a T cell stimulated by an immobilized anti-CD3 antibody. The BTNL3 protein can be made in a non-human or mammalian host cell. Such a soluble BTNL3 protein or such a BTNL3 protein attached to a surface such as a microbead or expressed on a cell surface can be at least a dimer, a trimer, a tetramer, a pentamer, a hexamer, a heptamer, an octamer, a nonamer, a decamer, or a higher order multimer. In another aspect, the soluble BTNL3 protein or the BTNL3 protein attached to a surface such as a microbead or expressed on a cell surface may be no more than dimer, a trimer, a tetramer, a pentamer, a hexamer, a heptamer, an octamer, a nonamer, a decamer. Such a BTNL3 protein or such a BTNL3 protein attached to a surface such as a microbead or expressed on a cell surface can further comprise another polypeptide, such as, for example, an Fc fragment of an antibody and/or a linker. Such a soluble BTNL3 or such a BTNL3 protein attached to a surface such as a microbead or expressed on a cell surface protein can be a multimer, wherein the multimer has a molecular weight at least about two, three, four, five, six, seven, eight, nine, ten, eleven, twelve, thirteen, fourteen, fifteen, or sixteen times as large as that of the monomeric soluble BTNL3 protein. In addition, the soluble BTNL3 protein or the BTNL3 protein attached to a surface such as a microbead or expressed on a cell surface can be a multimer, wherein the multimer has a molecular weight no more than about two, three, four, five, six, seven, eight, nine, ten, eleven, twelve, thirteen, fourteen, fifteen, or sixteen times as large as that of the monomeric soluble BTNL3 protein. Nucleic acids encoding such BTNL3 fusion proteins are also provided, as well as vectors comprising these nucleic acids and host cells containing the vectors and/or the nucleic acids.

In a further embodiment, there is provided a BTNL3 fusion protein encoded by a DNA, wherein the DNA comprises the following: (a) a DNA, which encodes a polypeptide, wherein the DNA (i) consists of the nucleotide sequence from nucleotide 52, 55, 58, or 61 to 696, 699, 702, 705, or 708 of SEQ ID NO:1 or nucleotide 52, 55, 58, or 61 to 486, 489, 492, 495, or 498 of SEQ ID NO:8; or (ii) hybridizes under stringent conditions to the DNA of (i); and (b) another DNA that does not hybridize to a polynucleotide consisting of the sequence of SEQ ID NO:1 or SEQ ID NO:8 and encodes a another polypeptide in frame with the polypeptide encoded by the polynucleotide of (a); wherein the fusion protein can inhibit the proliferation of a T cell stimulated by an immobilized anti-CD3 antibody. The BTNL3 fusion protein can comprise a linker sequence and can be an isolated and/or soluble protein. Such a BTNL3 fusion protein can be a multimer, wherein the multimer has a molecular weight at least about two, three, four, five, six, seven, eight, nine, ten, eleven, twelve, thirteen, fourteen, fifteen, or sixteen times as large as that of the monomeric BTNL3 fusion protein. In a further aspect, such a BTNL3 fusion protein can be a multimer, wherein the multimer has a molecular weight of no more than about two, three, four, five, six, seven, eight, nine, ten, eleven, twelve, thirteen, fourteen, fifteen, or sixteen times as large as that of the monomeric BTNL3 fusion protein. Nucleic acids encoding such BTNL3 fusion proteins are also provided, as well as vectors comprising these nucleic acids and host cells containing the vectors and/or the nucleic acids.

Any of the BTNL3 proteins discussed above or below can be isolated and/or soluble and can comprise multimers or aggregated species, which comprise multiple molecules of a BTNL3 protein. The molecular weight of the monomeric BTNL3 protein species contained in the multimer or aggregate can be measured by gel electrophoresis under reducing conditions or by size exclusion chromatography (SEC) done under reducing conditions. The molecular weight of the multimeric or aggregated species can be measured by gel electrophoresis and/or SEC done under non-reducing conditions. In some embodiments the multimer or aggregate has a molecular weight that is at least about 2, 3, 4, 5, 6, 7, 8, 9, 10, 11, 12, 13, 14, 15, or 16 times that of the monomeric species. In some embodiments the multimer or aggregate has a molecular weight that is no more than about 2, 3, 4, 5, 6, 7, 8, 9, 10, 11, 12, 13, 14, 15, or 16 times that of the monomeric species. The monomeric BTNL3 protein of such a multimer or aggregate comprises (a) a polypeptide containing the amino acid sequence from amino acid from amino acid 18, 19, 20, 21, 22, or 23 to 234, 235, 236, 237, or 238 of SEQ ID NO:2 or from amino acid 18, 19, 20, 21, 22, or 23 to 164, 165, 166, 167, or 168 of SEQ ID NO:9; (b) a polypeptide having an amino acid sequence at least 90%, 95%, 97% or 99% identical to amino acids 18-236 of SEQ ID NO:2 or 18-166 of SEQ ID NO:9, wherein the alignment window of the amino acid sequence of the polypeptide of (b) with amino acids 18-236 of SEQ ID NO:2 or 18-166 of SEQ ID NO:9 is at least 50, 60, 70, 80, 90, or 100 amino acids long; or (c) a polypeptide having a sequence like that of amino acids 18-236 of SEQ ID NO:2 or 18-166 of SEQ ID NO:9 except that it can contain no more than 20, 15, 10, or 5 insertions, deletions, or substitutions of a single amino acid relative to amino acids 18-236 of SEQ ID NO:2 or 18-166 of SEQ ID NO:9.

In another aspect, described herein is an isolated variant BTNL3 protein comprising a polypeptide comprising an amino acid sequence at least 90% or 95% identical to amino acids 18-236 of SEQ ID NO:2 or to amino acids 18-166 of SEQ ID NO:9, wherein the alignment window of the amino acid sequence with amino acids 18-236 of SEQ ID NO:2 or amino acids 18-166 of SEQ ID NO:9 is at least 80 amino acids long, wherein the protein does not comprise the amino acid sequence of amino acids 18-236 of SEQ ID NO:2 or amino acids 18-166 of SEQ ID NO:9, and wherein the protein can antagonize the inhibition by a BTNL3 protein comprising the amino acid sequence of SEQ IN NO:7 of proliferation of a T cell stimulated by an immobilized anti-CD3 antibody.

Also described herein is an isolated DNA encoding any of the BTNL3 proteins described herein, including the multimeric, fusion, and variant BTNL3 proteins, wherein the DNA does not include exon sequences.

In another aspect, there is provided a DNA encoding a fusion protein comprising a BTNL3 protein and another polypeptide, wherein the DNA comprises: (a) a DNA (i) that consists of the DNA sequence from nucleotide 52, 55, 58, or 61 to 696, 699, 702, 705, or 708 of SEQ ID NO:1 or nucleotide or 52, 55, 58, or 61 to 486, 489, 492, 495, or 498 of SEQ ID NO:8; or (ii) that hybridizes under stringent conditions to the DNA of (i); and (b) another DNA that does not hybridize to a DNA consisting of the sequence of SEQ ID NO:1 or SEQ ID NO:8 and encodes a another polypeptide in frame with the polypeptide encoded by the DNA of (a); wherein the fusion protein can inhibit the proliferation of a T cell stimulated by an immobilized anti-CD3 antibody. Vectors containing these DNAs and host cells containing the vectors and/or the DNAs are also contemplated.

The invention provides a method of making any of the BTNL3 proteins discussed above, including the multimeric BTNL3 protein, the BTNL3 fusion proteins, and the soluble or variant BTNL3 protein or the BTNL3 protein attached to a surface such as a microbead or expressed on a cell surface, comprising culturing a host cell containing nucleic acids encoding the BTNL3 protein in a medium under conditions suitable for expression of the DNA and recovering the expressed BTNL3 protein from the cell mass or the culture medium. The DNAs can be introduced into the host cell.

In still another aspect, a method of treating a patient having an autoimmune or inflammatory disease is provided, which comprises administering to the patient a therapeutically effective dose of any one of the following: (1) any BTNL3 protein comprising the amino acid sequence of amino acids 18-236 of SEQ ID NO:2 or amino acids 18-166 of SEQ ID NO:9, (2) a variant thereof which comprises an amino acid sequence at least 90%, 95%, 96%, 97%, 98%, 99%, or 100% identical to amino acids 18-236 of SEQ ID NO:2 or amino acids 18-166 of SEQ ID NO:9, or which comprises an amino acid sequence that has no more than 5, 10, 15, or 20 insertions, deletions, or substitutions of a single amino acid relative to the sequence of amino acids 18-236 of SEQ ID NO:2 or amino acids 18-166 of SEQ ID NO:9, wherein the BTNL3 variant protein can inhibit the proliferation of a T cell stimulated by an immobilized anti-CD3 antibody; or (3) a BTNL3 agonist such as an agonistic anti-BTNL3 antibody or an anti-idiotypic antibody to an anti-BTNL3 antibody. Alternatively, such a treatment could be performed ex vivo. As a further alternative, the BTNL3 protein or agonist could be attached to a small particle for in vivo or ex vivo administration such as administration on a nanoparticle. This method would include the use of any of the multimeric BTNL3 proteins, the BTNL3 fusion proteins, or the BTNL3 proteins discussed above and below for practicing the method with the exception of those BTNL3 variant proteins that can antagonize the inhibition of T cell proliferation by a BTNL3 protein comprising the amino acid sequence of SEQ ID NO:7. The autoimmune or inflammatory disease can be arthritis including rheumatoid arthritis, juvenile idiopathic arthritis, and psoriatic arthritis, Addison's disease, asthma, poly glandular endocrinopathy syndromes, systemic lupus erythematosus, chronic active hepatitis, thyroiditis, lymphocytic adenohypophysitis, premature ovarian failure, idiopathic phyoparathyroidism, pernicious anemia, glomerulonephritis, autoimmune neutropenia, Goodpasture's syndrome, myasthenia gravis, scleroderma, primary Sjogren's syndrome, polymyositis, autoimmune hemolytic anemia, an inflammatory bowel disease, such as Crohn's disease or ulcerative colitis, psoriasis, dermatitis, sarcoidosis, multiple sclerosis, chronic obstructive pulmonary disease, asthma, type 1 and type 2 diabetes, transplantation-related conditions such as graft rejection or graft versus host disease, gout and related inflammatory crystal deposition diseases, or a fibrotic disease, such as atherosclerosis, chronic obstructive pulmonary disease (COPD), cirrhosis, scleroderma, kidney transplant fibrosis, kidney allograft nephropathy, pulmonary fibrosis, including idiopathic pulmonary fibrosis, autoimmune thrombocytopenic purpura, pemphigus vulgaris, acute rheumatic fever, mixed essential cryoglobulinemia, and warm autoimmune hemolytic anemia, among many others.

In a further aspect, a method for inhibiting T cell proliferation is provided, which comprises adding to the T cell (1) any BTNL3 protein comprising the amino acid sequence from amino acid 18, 19, 20, 21, 22, or 23 to 234, 235, 236, 237, or 238 of SEQ ID NO:2 or from amino acid 18, 19, 20, 21, 22, or 23 to 164, 165, 166, 167, or 168 of SEQ ID NO:9 or (2) a variant thereof which comprises an amino acid sequence at least 90%, 95%, 96%, 97%, 98%, 99%, or 100% identical to amino acids 18-236 of SEQ ID NO:2 or 18-166 of SEQ ID NO:9 or which comprises an amino acid sequence that has no more than 5, 10, 15, or 20 insertions, deletions, or substitutions of a single amino acid relative to the sequence of amino acids 18-236 of SEQ ID NO:2 or amino acids 18-166 of SEQ ID NO:9, wherein the BTNL3 protein can inhibit the proliferation of T cells stimulated by an immobilized anti-CD3 antibody. This method encompasses the use of soluble multimeric BTNL3 protein, the BTNL3 fusion proteins, or the soluble BTNL3 protein discussed above and below to inhibit T cell proliferation. This inhibition of T cell proliferation can occur in vitro, ex vivo, or in vivo.

In another aspect, a method for expanding regulatory T ("T reg") cells is provided, which comprises adding to a T cell (1) a BTNL3 protein comprising the amino acid sequence from amino acid 18, 19, 20, 21, 22, or 23 to 234, 235, 236, 237, or 238 of SEQ ID NO:2 or from amino acid 18, 19, 20, 21, 22, or 23 to 164, 165, 166, 167, or 168 of SEQ ID NO:9 or (2) a variant thereof which comprises an amino acid sequence at least 90%, 95%, 96%, 97%, 98%, 99%, or 100% identical to amino acids 18-236 of SEQ ID NO:2 or 18-166 of SEQ ID NO:9 or which comprises an amino acid sequence that has no more than 5, 10, 15, or 20 insertions, deletions, or substitutions of a single amino acid relative to the sequence of amino acids 18-236 of SEQ ID NO:2 or amino acids 18-166 of SEQ ID NO:9, wherein the BTNL3 protein or the variant BTNL3 protein can inhibit the proliferation of T cells stimulated by an immobilized anti-CD3 antibody. This method encompasses the use of a BTNL3 protein attached to a surface such as a plate or a bead or expressed on a cell surface, a soluble BTNL3 protein, which can be multimeric, or a BTNL3 fusion protein or soluble BTNL3 protein discussed above and below to expand T reg cells. This expansion of T reg cells can occur in vitro, ex vivo, or in vivo. The method comprises contacting a population of T cells with an effective amount of a BTNL3 protein, fusion protein, or agonist as described herein. "Expansion" of T reg cells means that the ratio of T reg cells (CD3$^+$FOXP3$^+$) to T cells as a whole (CD3$^+$FOXP3$^-$) becomes greater. This ratio can be determined by FACS analysis using antibodies to detect cell proteins, a method well known in the art. See, e.g., Swanson et al. (2013), J. Immunol. 190: 2027-2035, the relevant portions of which are incorporated herein by reference.

Another embodiment includes a method for treating a patient having an autoimmune or inflammatory disease comprising administering to the patient a therapeutically effective dose of an anti-BTNL3 antibody, wherein the anti-BTNL3 antibody agonizes the inhibition of proliferation of T cells by a native BTNL3 protein, wherein the anti-BTNL3 antibody binds to a protein consisting of the amino acid sequence of amino acids 18-236 of SEQ ID NO:2.

Another embodiment includes a method for treating a patient having an autoimmune or inflammatory disease comprising administering to the patient a therapeutically effective dose of an anti-BTNL3 antibody, wherein the anti-BTNL3 antibody can bind to a protein consisting of the amino acid sequence of amino acids 18 to 236 of SEQ ID NO:2. In some embodiments, the anti-BTNL3 antibody can bind to a cell surface BTNL3 protein and induce an intracellular signaling cascade via the B30.2 domain of BTNL3, for example, in neutrophils expressing BTNL3. Such intracellular signaling can inhibit proliferation of the cells expressing BTNL3 or, in some cases, cause cell death. The autoimmune or inflammatory diseases include, for example, those that are characterized by excess neutrophil activity such as congestive obstructive pulmonary disease (COPD), asthma, inflammatory bowel disease, including ulcerative colitis and Crohn's disease, and gout and related inflammatory crystal deposition diseases.

A further method includes a treatment for a cancer patient comprising administering to the patient a therapeutically effective amount of an antibody that binds to a BTNL3 protein consisting of amino acids 18 to 236 of SEQ ID NO:2 or to a BTNL3 protein at least 90% or 95% identical to amino acids 18 to 236 of SEQ ID NO:2. In some embodiments, such an anti-BNTL3 antibody can bind to a human BTNL3 protein as described herein with an equilibrium dissociation constant ($K_D$) of no more than $10^{-8}$, $10^{-9}$, 10', or $10^{-11}$ M. In some embodiments, such an anti-BTNL3 antibody can bind to a BTNL3 protein comprising an amino acid sequence at least 90%, 95%, 97%, 98%, or 100% identical to SEQ ID NO:2 and/or SEQ ID NO:9, wherein the alignment window with SEQ ID NO:2 and/or 9 is at least 50, 60, 70, 80, or 100 amino acids long and, optionally, wherein the BTNL3 protein can inhibit the proliferation of a T cell stimulated by an immobilized anti-CD3 antibody. In some embodiments, an anti-BTNL3 antibody can bind to a protein comprising a fragment of the amino acid sequence of SEQ ID NO:2 and/or 9.This antibody can be an antagonistic anti-BTNL3 antibody that antagonizes the suppression of T cell proliferation by BTNL3. Alternatively, the antibody may bind to BTNL3 expressed on a cancer cell, thereby signaling the cancer cell so as to inhibit its proliferation or, in some cases cause cell death. The cancer can be, for example, acute or chronic leukemias, lymphoma, non-Hodgkin's lymphoma, Hodgkin's disease, lymphocytic leukemias, lymphocytic or cutaneous lymphomas, carcinomas, adenocarcinomas, sarcomas, thymomas, neoplasms of the mediastinum, breast cancer, prostate cancer, cancers of the head and neck, lung cancer, non-small cell lung cancer, small cell lung cancer, various kinds of skin cancer, cancer of the bladder, malignant gliomas, cancer of the esophagus, cancer of the stomach, cancer of the pancreas, hepatobiliary neoplasms, cancer of the small intestine, colon, or rectum, cancer of the kidney or ureter, testicular cancer, cancer of the urethra or penis, gynecologic tumors, ovarian cancer, sarcomas of the bone, cancers of the endocrine system, cutaneous melanoma, intraocular melanoma, neoplasms of the central nervous system, and plasma cell neoplasms. In some embodiments, the antibody can be an agonistic antibody that binds to BTNL3 expressed on the cancer cells, causing intracellular signaling via the B30.2 domain.

Further provided is a method of treating a cancer patient comprising administering to the patient a therapeutically effective amount of a variant BTNL3 protein comprising a polypeptide comprising an amino acid sequence at least 90% or 95% identical to amino acids 18-236 of SEQ ID NO:2 or amino acids 18-166 of SEQ ID NO:9, wherein the alignment window of the amino acid sequence with amino acids 18-236 of SEQ ID NO:2 or amino acids 18-166 of SEQ ID NO:9 is at least 80 amino acids long, wherein the variant BTNL3 protein does not comprise the amino acid sequence of amino acids 18-236 of SEQ ID NO:2 or amino acids 18-166 of SEQ ID NO:9, and wherein the variant BTNL3 protein can antagonize the inhibition by a BTNL3 protein comprising the amino acid sequence of SEQ IN NO:7 of proliferation of a T cell stimulated by an immobilized anti-CD3 antibody. The cancer can be an adenocarcinoma.

In another aspect, provided herein is a method of treating a patient infected with a pathogen comprising administering to the patient a therapeutically effective amount of an antibody that binds to a BTNL3 protein, the amino acid sequence of which consists of amino acids 18-236 of SEQ ID NO:2 and/or amino acids 18-166 of SEQ ID NO:9, or to a BTNL3 protein, the an amino acid sequence of which consists of a sequence at least 90% or 95% identical to amino acids 18-236 of SEQ ID NO:2 and/or amino acids 18-166 of SEQ ID NO:9, wherein the alignment window of the amino acid sequence with amino acids 18-236 of SEQ ID NO:2 or amino acids 18-166 of SEQ ID NO:9 is at least 80 amino acids long. The antibody can be an antagonistic antibody that can antagonize the inhibition by a BTNL3 protein comprising the amino acid sequence of SEQ IN NO:7 of proliferation of a T cell stimulated by an immobilized anti-CD3 antibody.

In a further aspect, described herein is a method of treating a patient infected with a pathogen comprising administering to the patient a therapeutically effective amount of a variant BTNL3 protein comprising a polypeptide comprising an amino acid sequence at least 90% or 95% identical to amino acids 18-236 of SEQ ID NO:2 or amino acids 18-166 of SEQ ID NO:9, wherein the alignment window of the amino acid sequence with amino acids 18-236 of SEQ ID NO:2 or amino acids 18-166 of SEQ ID NO:9 is at least 80 amino acids long, wherein the variant BTNL3 protein does not comprise the amino acid sequence of amino acids 18-236 of SEQ ID NO:2 or amino acids 18-166 of SEQ ID NO:9, and wherein the variant BTNL3 protein can antagonize the inhibition by a BTNL3 protein comprising the amino acid sequence of SEQ IN NO:7 of proliferation of a T cell stimulated by an immobilized anti-CD3 antibody.

In another aspect, described herein is a method for treating a patient having an autoimmune or inflammatory condition comprising the following steps: (a) removing T cells from the patient; (b) stimulating the T cells with a combination of proteins comprising an anti-CD3 antibody and a BTNL3 protein, wherein the BTNL3 protein comprises (i) the amino acid sequence of amino acids 18-236 of SEQ ID NO:2 or amino acids 18-166 of SEQ ID NO:9, (ii) an amino acid sequence at least 90% or 95% identical to amino acids 18-236 of SEQ ID NO:2 or amino acids 18-166 of SEQ ID NO:9, wherein the alignment window of the amino acid sequence with amino acids 18-236 of SEQ ID NO:2 or amino acids 18-166 of SEQ ID NO:9 is at least 80 amino acids long, or (iii) an amino acid sequence that has no more than 20 insertions, deletions, or substitutions of a single amino acid relative to the sequence of amino acids 18-236 of SEQ ID NO:2 or amino acids 18-166 of SEQ ID NO:9; (c) harvesting the stimulated T cells; and (d) returning the harvested T cells to the patient; wherein the BTNL3 protein can inhibit the proliferation of a T cell stimulated by an immobilized anti-CD3 antibody. The BTNL3 protein can be the BTNL3 protein of (b)(iii), wherein the amino acid sequence has no more than 5 or10 insertions, deletions, or substitutions of a single amino acid relative to the sequence of amino acids 18-236 of SEQ ID NO:2 or amino acids 18-166 of SEQ ID NO:9. The BTNL3 protein can be the BTNL3 protein of (b)(i). The autoimmune or inflammatory condition can be selected from the group consisting of arthritis including rheumatoid arthritis, juvenile idiopathic arthritis, and psoriatic arthritis, Addison's disease, asthma, polyglandular endocrinopathy syndromes, systemic lupus erythematosus, chronic active hepatitis, thyroiditis, lymphocytic adenohypophysitis, premature ovarian failure, idiopathic phyoparathyroidism, pernicious anemia, glomerulonephritis, autoimmune neutropenia, Goodpasture's syndrome, myasthenia gravis, scleroderma, primary Sjogren's syndrome, polymyositis, autoimmune hemolytic anemia, an inflammatory bowel disease, such as Crohn's disease or ulcerative colitis, psoriasis, dermatitis, sarcoidosis, multiple sclerosis, chronic obstructive pulmonary disease, asthma, type 1 and type 2 diabetes, transplantation-related conditions such as graft rejection or graft versus host disease, gout and related inflammatory crystal deposition diseases, or a fibrotic disease, such as atherosclerosis, chronic obstructive pulmonary disease (COPD), cirrhosis, scleroderma, kidney transplant fibrosis, kidney allograft nephropathy, pulmonary fibrosis, including idiopathic pulmonary fibrosis, autoimmune thrombocytopenic purpura, pemphigus vulgaris, acute rheumatic fever, mixed essential cryoglobulinemia, and warm autoimmune hemolytic anemia, among many others.

A method is provided for vaccinating a patient, for example against a cancer or a pathogen, which comprises administering to the patient an antigen and (a) an antagonistic antibody that binds to (i) a BTNL3 protein, the amino acid sequence of which consists of amino acids 18-236 of SEQ ID NO:2 or amino acids 18-166 of SEQ ID NO:9, or (ii) a BTNL3 protein, the amino acid sequence of which consists of a sequence at least 90% or 95% identical to amino acids 18-236 of SEQ ID NO:2 or amino acids 18-166 of SEQ ID NO:9, wherein the alignment window of the amino acid sequence with amino acids 18-236 of SEQ ID NO:2 or amino acids 18-166 of SEQ ID NO:9 is at least 80 amino acids long; or (b) a variant BTNL3 protein comprising a polypeptide comprising an amino acid sequence at least 90% or 95% identical to amino acids 18-236 of SEQ ID NO:2 or amino acids 18-166 of SEQ ID NO:9, wherein the alignment window of the amino acid sequence with amino acids 18-236 of SEQ ID NO:2 or amino acids 18-166 of SEQ ID NO:9 is at least 80 amino acids long, wherein the variant BTNL3 protein does not comprise the amino acid sequence of amino acids 18-236 of SEQ ID NO:2 or amino acids 18-166 of SEQ ID NO:9, and wherein the variant BTNL3 protein can antagonize the inhibition by a BTNL3 protein comprising the amino acid sequence of SEQ IN NO:7 of proliferation of a T cell stimulated by an immobilized anti-CD3 antibody. The antigen can be a cancer antigen or an antigen that can elicit an immune response against the pathogen. The antagonistic antibody can antagonize the inhibition by a BTNL3 protein comprising the amino acid sequence of SEQ IN NO:7 of proliferation of a T cell stimulated by an immobilized anti-CD3 antibody. In such methods the antagonistic anti-BNTL3 antibody or the variant BTNL3 protein can be administered before, concurrently with, or after the antigen. Contemplated here are vaccines comprising an antagonistic anti-BTNL3 antibody or a variant BTNL3 protein and an antigen.

BRIEF DESCRIPTION OF THE SEQUENCE LISTING

Figure 1:
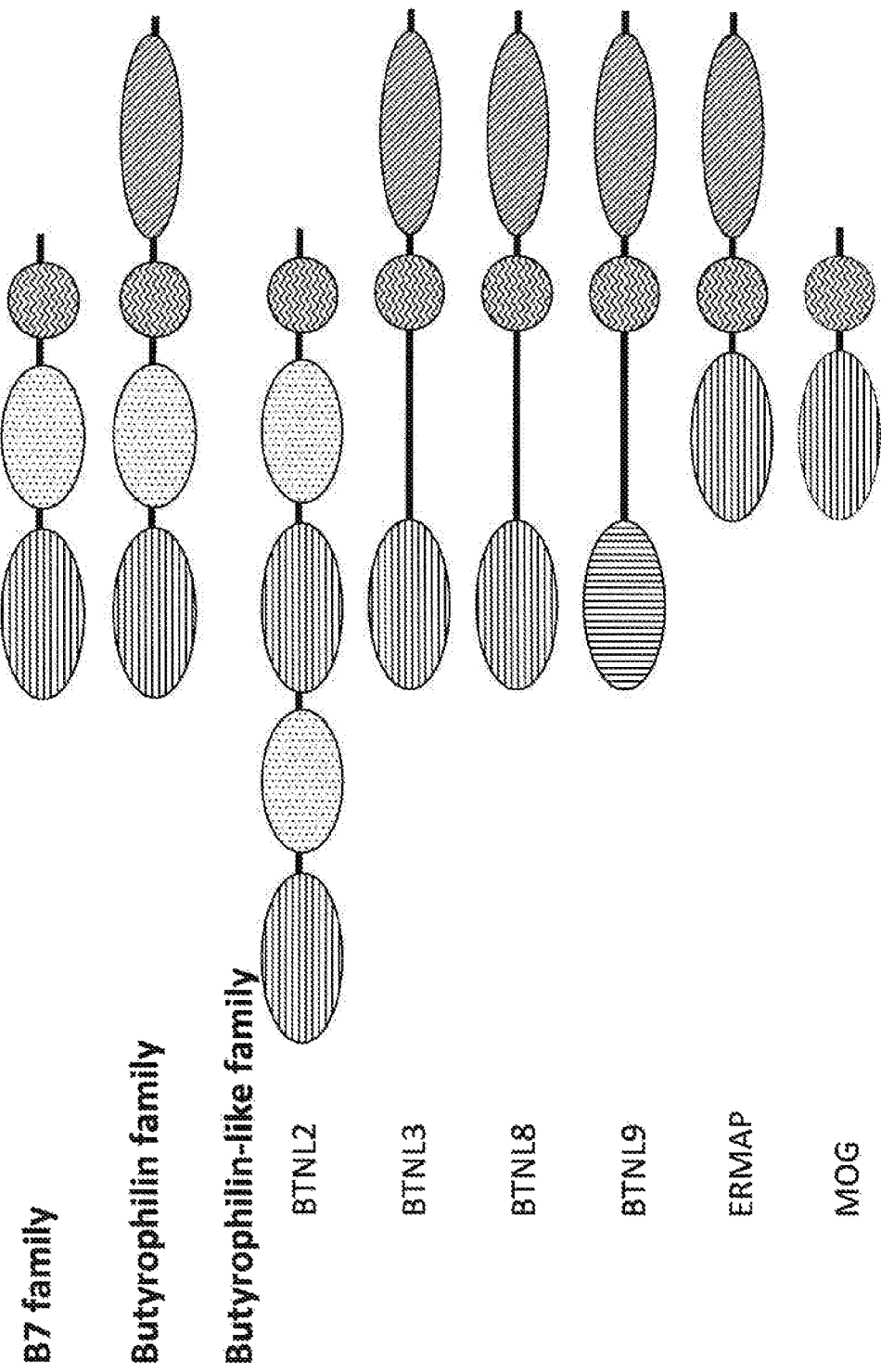
FIG. 1: The domain structures of the human proteins that are part of the butyrophilin-like (BTNL) protein family (BTNL2, BTNL3, BTNL8, BTNL9, ERMAP, and MOG), as well as the general structures of the related butyrophilin and B7 families, are diagrammed Each oval or circle represents a protein domain. The domains are indicated as follows: ▤, immunoglobulin variable region-like (IgV-like) domain; ▦, immunoglobulin constant region-like (IgC-like) domain; ▨, transmembrane domain; and ▩, B30.2 domain. Regions not identified with a particular domain structure are indicated by a horizontal line.

SEQ ID NO:1: Nucleotide sequence encoding human BTNL3 coding region.
SEQ ID NO:2: Amino acid sequence of human BTNL3.
SEQ ID NO:3: Amino acid sequence of an IgK signal sequence.
SEQ ID NO:4: Amino acid sequence of a signal sequence for human growth hormone.
SED ID NO:5: Full length nucleotide sequence encoding human BTNL3.Fc fusion protein.
SEQ ID NO:6: Full length amino acid sequence of human BTNL3 fusion protein.
SEQ ID NO:7: Amino acid sequence of mature BTNL3.Fc (without signal sequence).
SEQ ID NO:8: Nucleotide sequence encoding a splice variant of BTNL3.
SEQ ID NO:9: Amino acid sequence encoded by SEQ ID NO:8.
SEQ ID NO:10: Peptide linker.
SEQ ID NO:11: Peptide linker.
SEQ ID NO:12: Peptide linker.
SEQ ID NO:13: Peptide linker.
SEQ ID NO:14: Peptide linker.
SEQ ID NO:15: Peptide linker.
SEQ ID NO:16: Peptide linker.
SEQ ID NO:17: Peptide linker.
SEQ ID NO:18: Peptide linker.

DETAILED DESCRIPTION

The invention provides uses for BTNL3 proteins or antagonists or agonists of a BTNL3 protein, such as anti-BTNL3 antibodies and/or variant forms of a BTNL3 protein. The invention provides BTNL3 proteins, including multimers, fusion proteins, and variants thereof, and uses for such proteins, as well as nucleic acids encoding all of the above. BTNL3 proteins can alter T cell function by attenuating T cell activation, proliferation, and cytokine production. Such effects can lead to effective treatments of T cell-mediated autoimmune or inflammatory diseases such as inflammatory bowel diseases and fibrotic disorders, among a number of others. Antagonists of BTNL3 can function to prevent or antagonize BTNL3 from inhibition of T cell activation, proliferation, and cytokine secretion, thus, leading to an overall increase in T cell activation. Such effects can be useful for treating diseases such as cancer or for enhancing the efficacy of a vaccine. Further, agonists of BTNL3 may be able to alter immune cell function, for example, by clustering the BTNL3 protein without blocking its function. Such agonists may mediate intracellular signaling into cells expressing BTNL3 via the B30.2 domain that may modulate the activity of such cells by, for example, increasing or decreasing proliferation and/or cytokine secretion. Since BTNL3 is expressed on neutrophils and some kinds of cancer cells, such intracellular signaling may modulate the course of diseases mediated by such cells.

Definitions

The biological activity of a BTNL3 antagonist that can "antagonize the inhibition by a BTNL3 protein comprising the amino acid sequence of SEQ ID NO:7 of proliferation of a T cell stimulated by an immobilized anti-CD3 antibody" can be determined by doing a T cell proliferation assay as described in Example 4 and adding the antagonist to some of the samples in a controlled fashion so as to determine whether the antagonist affects the activity of a BTNL3 protein comprising the amino acid sequence of SEQ ID NO:7. By a similar test, the activity of an agonistic antibody that increases the inhibition of T cell proliferation by T cells can be assayed.

An "antibody," as meant herein, comprises a heavy chain variable region of an immunoglobulin and/or a light chain variable region of an immunoglobulin. An antibody may be a full length, tetrameric antibody comprising a light chain variable region ($V_L$), a light chain constant region ($C_L$), a heavy chain variable region ($V_H$), a first heavy chain constant region ($C_H1$), a hinge region, a second heavy chain constant region ($C_H2$), and a third heavy chain constant region ($C_H3$), such as an IgG, IgA, IgD, IgM, or IgE antibody. Alternatively, an antibody can be a fragment such as a Fab fragment or, optionally, a recombinant fragment, such as an scFv fragment. Single domain antibodies comprising a single variable region, either a $V_H$ or $V_L$ region, are also antibodies as meant herein. Single domain antibodies are described in US Patent Appln. Publication US 2006/0062784, the portions of which describe single domain antibodies are hereby incorporated by reference. Further, various forms of monovalent (including single chain antibodies such as scFvs, Fabs, scFv-Fcs, domain antibodies, and various formats described, for example, in International Application WO 2009/089004 and U.S. Pat. No. 5,837,821, the descriptive portions of which are incorporated herein by reference) and multivalent molecules (such as F(ab)2's and those described, for example, in International Application WO 2009/089004 and U.S. Pat. No. 5,837,821, the descriptive portions of which are incorporated herein by reference) are encompassed within the meaning of "antibody."

It is said in multiple places herein that a multimeric species of a protein has a molecular weight "at least about" two, three, four, five, six, seven, eight, nine, ten, eleven, twelve, thirteen, fourteen, fifteen, or sixteen times that of a monomeric species of the protein. While the meaning of this is plain, this phrase is specifically meant to include species that are about four, five, six, etc. times larger than a monomer and not only combinations of such species with larger species or only larger species. Similarly, it is said in multiple places that a multimer is "at least" a dimer, a trimer, a tetramer, etc. This phrase is specifically meant to include species that are dimers, trimers, tetramers, etc. and not only the combination of the stated species with larger species or only larger species. Further, it is said in multiple places herein that a multimeric species has a molecular weight that is "no more than" two, three, four, five, six, seven, eight, nine, ten, eleven, twelve, thirteen, fourteen, fifteen, or sixteen times that of a monomeric species of the protein. While the meaning of this is plain, this phrase is specifically meant to include species that are about four, five, six, etc. times larger than a monomer and not only combinations of such species with smaller species or only smaller species. Similarly, it is said in multiple places that a multimer is "no more than" a dimer, a trimer, a tetramer, etc. This phrase is specifically meant to include species that are dimers, trimers, tetramers, etc. and not only the combination of the stated species with smaller species or only smaller species.

"BTNL3 proteins," as meant herein, includes full length human, BTNL3 proteins and fragments and/or variants thereof, which includes proteins encoded by naturally-occurring allelic variants of the BTNL3 gene, as well as recombinantly-produced BTNL3 proteins, that is, proteins produced in host cells such as non-human or mammalian host cells, which may contain some sequence changes relative to naturally-occurring BTNL3 proteins. Proteins comprising soluble fragments of a full length human BTNL3 protein that include most or the entire extracellular region and do not include the transmembrane region are specifically contemplated. Such proteins can be attached to a surface such as a bead or a microtiter plate.

A patient is receiving "concurrent" treatment with two or more molecules, which may be, for example, therapeutics or components of a vaccine, when the patient receives the two or more molecules during the same general timeframe, optionally at the very same time. For example, if a patient were dosed with one molecule daily on an ongoing basis and were also dosed with another molecule once a month on an ongoing basis, the patient would be receiving these two molecules concurrently. Similarly, a patient dosed with two different molecules, each administered every two weeks, but not on the same day, would be receiving concurrent treatment with the two molecules. Further, a patient receiving one molecule on an ongoing basis once per week and another molecule once per day for only three days would be receiving concurrent treatment for a short period of time with these two molecule.

A "scFv" is a single chain antibody comprising a heavy chain variable region ($V_H$) and a light chain variable region ($V_L$) and not comprising a constant region of an antibody. In some embodiments scFv's can also comprise a linker of variable length between the heavy and light chain variable regions. Although an scFv can be fused to other amino acid sequences, the portion of a protein referred to as an scFv preferably does not comprise any substantial amount of amino acid sequence other than a $V_H$ region, a $V_L$ region, and, optionally, a linker joining these sequences.

An "Fc polypeptide," as meant herein, is a fragment of an antibody heavy chain comprising a $C_H2$ and a $C_H3$ domain and all or part of a hinge region or a variant of such a fragment. An Fc polypeptide does not comprise a $C_H1$ domain or a $V_H$ domain. See e.g. Kuby, Immunology, Second Edition, p. 110-11, W. H. Freeman and Co., New York (1994). An Fc polypeptide can be of the IgA, IgD, IgE, IgG, or IgA isotype, including IgG1, IgG2, IgG3, IgG4 or other subtypes. An Fc polypeptide can be multimeric, in some cases dimeric. Such multimeric Fc polypeptides are referred to herein as "Fc regions." Some Fc polypeptides, for example an IgM or IgA Fc polypeptides, can form higher order multimers. A single polypeptide chain within a multimeric Fc region is referred to as an "Fc polypeptide." Variants of Fc polypeptides, as meant herein, may comprise from 1 to 30 (including specifically, no more than 1, 2, 3, 4, 5, 6, 7, 8, 9, 10, etc.) insertions, deletions, or substitutions of a single amino acid relative to a naturally-occurring Fc polypeptide. A naturally occurring or "native" Fc polypeptide has a sequence that occurs in nature in a living organism, for example, a human or a mouse Fc polypeptide. Thus, a "native human" Fc polypeptide has an amino acid sequence that is found in a naturally occurring human Fc polypeptide. Guidance as to where variations can tolerated without affecting function can be found in the art. For example, alterations of amino acid residues identified in U.S. Pat. No. 5,807,706 and International Application WO 2009/089004, the relevant portions of which are incorporated herein by reference, may be used to encourage heterodimer formation as compared to homodimer formation. Similarly, alterations to the Fc polypeptide that do not prevent binding of the neonatal Fc receptor, FcRn, are encompassed within the alterations that can occur in Fc variants as meant herein. Binding of an Fc polypeptide to FcRn can be ascertained at about pH 6 using a Biacore instrument, such as a Biacore 3000. Human FcRn can be coupled to a CM5 chip using standard chemistry. The Fc-containing protein can be part of the mobile phase, and the response can be measured in resonance units. Alterations of Fc polypeptides are described in, for example, International Patent Application Publication WO 97/34631, the relevant portions of which are incorporated herein by reference. Alternatively, comparisons of, for example, IgG sequences within and between species can locate highly conserved amino acids, which would suggest to one of skill in the art that alteration of those amino acids may affect structure and/or function. Numerous alignments of sequences of hinge, $C_H2$ and $C_H3$ regions (which together form the Fc region) are available in, for example, Kabat et al., Sequences of Immunological Interest, National Institutes of Health, Publication No. 91-3242, 1991, the relevant portions of which are incorporated herein by reference. On the other hand, amino acids which vary among various IgGs are sites at which variation is likely to be tolerated without effect on function. Similarly, Fc variants that have other desired properties, such as increased or decreased effector functions, including antibody dependent cellular cytotoxicity and/or Clq binding, which leads to complement fixation, are encompassed within what is meant by Fc variants.

The term "full length antibody" refers to a molecule similar in structure to most naturally-occurring antibodies, for example, an IgG antibody, that is, containing two entire heavy chains and two entire light chains See e.g. Kabat et al., supra or Kuby, Immunology, Second Edition, p. 109-32, W. H. Freeman and Co., New York (1994) for discussion of the structure of naturally-occurring antibodies. The portions of these references describing the structure of full length antibodies are incorporated herein by reference. Also included among "full length antibodies" are antibodies similar in structure to the naturally-occurring dromedary antibodies that contain only two complete heavy chains (often with an unusually long CDR3 region) and no light chains. Muldermans et al. (2001), J. Biotechnol. 74:277-302; Desmyter et al. (2001), J. Biol. Chem. 276:26285-26290. The portions of these references describing the structure of these dromedary antibodies are incorporated herein by reference.

A "multimeric" protein, such as a multimeric BTNL3 protein, is a protein comprising more than one polypeptide chain. The term "multimer" encompasses terms such as "dimer," "trimer," or "tetramer," which specify how many polypeptide chains the multimer contains. A "homomultimer" consists of two or more copies of the same polypeptide chain and does not contain any different polypeptide chains. Similarly, a "homodimer" consists of two copies of the same polypeptide chain, a "homotrimer" consists of three copies of the same polypeptide chain, etc. A "heteromultimer" contains at least two different polypeptide chains. If the heteromultimer has three or more polypeptide chains, some of them can be identical to each other as long as at least one is different from the others. When a protein is said to be "at least a trimer," it is meant that it is a trimer or a higher order multimer. Similar meanings would be ascribed to "at least a tetramer," "at least a pentamer," etc. Similarly, a multimeric protein that is "no more than" a trimer is a trimer or a dimer.

A "Fab fragment" is an antibody fragment comprising a light chain comprising a $V_L$ and $C_L$ region and a portion of a heavy chain comprising a $V_H$ and a $C_H1$ region. A Fab fragment does not comprise a $C_H2$ or $C_H3$ region. See e.g., Kuby, Immunology, Second Edition, pp. 110-11 W. H. Freeman and Co., New York (1994) for a discussion of what Fab fragments are. Different kinds of Fab fragments may contain either no hinge region, a portion of a hinge region, or an entire hinge region.

An "scFv-Fc," as used herein, is a recombinant protein that is a fusion of an scFv with an Fc polypeptide. See Li et al. (2000), Cancer Immunol. Immunother. 49:243-252; Powers et al. (2001), J. Immunol. Methods 251:123-135; Gilliland et al. (1996), Tissue Antigens 47:1-20. An scFv-Fc can be dimeric.

As meant herein, "non-reducing conditions" are conditions under which disulfide bridges within a protein will not be reduced such that the bridges will be destroyed.

A "recombinant" protein or antibody is one resulting from the process of genetic engineering. The term "genetic engineering" refers to a recombinant DNA or RNA method used to create a cell that expresses a gene at elevated levels or at lowered levels, or expresses a mutant form of the gene. In other words, the cell has been transfected, transformed or transduced with a recombinant polynucleotide molecule, and thereby altered so as to cause the cell to alter expression of a desired polypeptide.

Soluble secreted proteins and proteins expressed on the cell surface often comprise an N-terminal "signal sequence," which is a hydrophobic sequence that mediates insertion of the protein through the membrane bounding the endoplasmic reticulum (ER) in a eukaryotic cell. Type I transmembrane proteins also comprise signal sequences. "Signal sequences," as meant herein are amino-terminal hydrophobic sequences which are usually enzymatically removed following the insertion of part or all of the protein through the ER membrane into the lumen of the ER. Thus, it is known in the art that a signal sequence can be present as part of a precursor form of a secreted or transmembrane protein, but will generally be absent from the mature form of the protein. When a protein is said to comprise a signal sequence, it is to be understood that, although a precursor form of the protein does contain the signal sequence, a mature form of the protein will likely not contain the signal sequence. Signal sequences contain a residue adjacent to and immediately upstream from the cleavage site (position −1) and another residue at position −3, which are important for this enzymatic cleavage. Nielsen et al. (1997), Protein Eng. 10(1):1-6; von Heijne (1983), Eur. J. Biochem. 133:17-21; von Heijne (1985), J. Mol. Biol. 184:99-105, the portions of which describe signal sequences and how to identify them are incorporated herein by reference. Signal sequences can be identified as described by Nielsen et al. (supra). Examples of signal peptides or sequences that are functional in mammalian host cells include the following: the signal sequence for interleukin-7 (IL-7) described in U.S. Pat. No. 4,965, 195; the signal sequence for interleukin-2 receptor described in Cosman et al. ((1984), Nature 312:768); the interleukin-4 receptor signal peptide described in EP Patent 0 367 566; the type I interleukin-1 receptor signal sequence described in U.S. Pat. No. 4,968,607; the type II interleukin-1 receptor signal peptide described in EP Patent 0 460 846; the signal sequence of human IgK (which is METDTLLLWVLLL-WVPGSTG; SEQ ID NO:3); and the signal sequence of human growth hormone (MATGSRTSLL-LAFGLLCLPWLQEGSA; SEQ ID NO:4). The relevant portions of these references are incorporated herein by reference. Many other signal sequences are known in the art.

An "immunoglobulin-like" (Ig-like) domain, as meant herein, is distinguished mainly by its tertiary structure. See e.g. Bork et al. (1994), J. Mol. Biol. 242: 309-20; Hunkapiller and Hood (1989), Adv. Immunol. 44: 1-63; Williams and Barclay (1988), Ann. Rev. Immunol. 6: 381-405. However, variable and constant immunoglobulin-like domains do contain a handful of highly conserved amino acids that occur at conserved positions within their primary amino acid sequence. See e.g. Kabat et al. (1991), Sequences of Proteins of Immunological Interest, U.S. Dept. of Health and Human Services, Public Health Service, National Institutes of Health, NIH Publication No. 91-3242. Such conserved amino acids in variable regions and in $C_H1$ and $C_H2$ constant regions are discussed in detail in, e.g., Harpaz and Chothia (1994), J. Mol. Biol. 238: 528-39 and Williams and Barclay (1988), Ann. Rev. Immunol. 6: 381-405. The portions of these references that discuss such conserved residues are incorporated herein by reference. The presence of such highly conserved amino acids or conservative variants thereof occurring in the proper spacing can indicate the presence of an IgC-like or IgV-like domain.

The percent identity of two amino acid or two nucleic acid sequences can be determined by comparing sequence information using the computer program GAP, i.e., Genetics Computer Group (GCG; Madison, Wis.) Wisconsin package version 10.0 program, GAP (Devereux et al. (1984), Nucleic Acids Res. 12: 387-95). The preferred default parameters for the GAP program includes: (1) The GCG implementation of a unary comparison matrix (containing a value of 1 for identities and 0 for non-identities) for nucleotides, and the weighted amino acid comparison matrix of Gribskov and Burgess, ((1986) Nucleic Acids Res. 14: 6745) as described in Atlas of Polypeptide Sequence and Structure, Schwartz and Dayhoff, eds., National Biomedical Research Foundation, pp. 353-358 (1979) or other comparable comparison matrices; (2) a penalty of 8 for each gap and an additional penalty of 2 for each symbol in each gap for amino acid sequences, or a penalty of 50 for each gap and an additional penalty of 3 for each symbol in each gap for nucleotide sequences; (3) no penalty for end gaps; and (4) no maximum penalty for long gaps.

In connection with comparisons to determine sequence identity of polynucleotides or polypeptides, what is meant by an "alignment window" is the portion of the polynucleotide or polypeptide that is matched, partially or wholly, with another polynucleotide or polypeptide by the computer program GAP (Devereux et al. (1984), Nucleic Acids Res. 12: 387-95) using the parameters stated herein. For example, when a polypeptide of 20 amino acids is aligned with a considerably longer protein and the first 10 amino acids match the longer protein exactly while the last 10 amino acids do not match the longer protein at all, the alignment window is 10 amino acids. If, on the other hand, the first and last amino acids of the 20 amino acid polypeptide match the longer protein, and eight other matches are scattered between, the alignment window is 20 amino acids long. However, long stretches in either aligned strand without identical or conservatively substituted amino acids or identical nucleotides of at least, for example, 25 amino acids or 75 nucleotides constitute an endpoint of an alignment window, as meant herein. Alignment windows for a comparison of sequences can be at least about 25, 50, 60, 75, 80, 90, 100, 150, 200, 225, 300, 400, 450, 500, or 600 amino acids or nucleotides in length.

Two polypeptide or nucleotide sequences are considered "substantially similar" when they are at least 90% identical as determined using the GAP program as described above and have similar biological activity. In the case of a BTNL3 protein or variant thereof as described herein, the biological activity to be tested in determining whether two sequences are substantially similar can be the ability to inhibit the proliferation of T cells activated by an immobilized anti-CD3 antibody or to antagonize such inhibition for certain antagonistic BTNL3 variant proteins.

The BTNL Family

BTNL3 has been placed within the butyrophilin-like (BTNL) family of proteins based on its domain structure. See, e.g., Arnett et al. (2008), Current Immunology Reviews 4: 43-52 and Arnett et al. (2009), Cytokine 46: 370-75. The human proteins in the BTNL family include BTNL2, BTNL3, BTNL8, BTNL9, ERMAP, and MOG, and the domain structures of these proteins are shown diagrammatically in FIG. 1. As is apparent from FIG. 1, BTNL2 is the only member of the family having four immunoglobulin-like (Ig-like) domains in its extracellular region (two IgV-like and two IgC-like domains). MOG and ERMAP each have only one Ig-like domain. BTNL3, BTNL8, and BTNL9 also have one extracellular domain that is clearly an IgV-like or Ig-like domain and another domain with many characteristics similar to an Ig-like domain, although these domains are not actually classified as Ig-like. All BTNL family members have a transmembrane domain. BTNL2 and MOG have short intracellular regions, whereas BTNL3, BTNL8, BTNL9, and ERMAP have longer intracellular regions containing a B30.2 domain. The function of the intracellular B30.2 is unknown, although mutations in B30.2 domains of some proteins have been associated with certain diseases. See Henry et al. (1998), Mol. Biol. Evol. 15: 1696-1705, the relevant disclosure of which is incorporated herein by reference. In addition, binding partners for some B30.2 domains have been identified, specifically, a xanthine oxidoreductase (XOR) that binds to the BTN1A1 B30.2 domain. See, e.g., Jeong et al. (2009), J. Biol. Chem. 284: 22444-22456. As hypothesized by Jeong et al., the interaction of XOR and BTN1A1 may play a role in the innate immune system by generating reactive oxygen and nitrogen species with antibacterial properties following engagement of BTN1A1 with receptors or bacterial surfaces. Id., at page 11. Reactive oxygen and nitrogen species may also act on downstream targets and regulate gene expression. Id. In addition, the B30.2 domain of BTN3A1 has been hypothesized to play a role in gamma delta T cell activation through its effects on the tertiary structure of the extracellular domains of BTN3A1. Palakodeti et al. (2012), J. Biol. Chem. 287: 32780-32790. In addition, an agonistic anti-BTN3 antibody decreased proliferation and cytokine production by lymphocytes expressing BNT3, effects that were correlated with phosphorylation of BTN3A. These results suggested that the observed effects on the lymphocytes were due to intracellular signaling, which might involve the B30.2 domain. Yamashiro et al. (2010), J. Leuk. Biol. 88: 757-767.

The degree of sequence identity shared by human BTNL3 with the other human members of the BTNL family is shown in below.

TABLE 1

Percent identity between human members of BTNL family of proteins

| | BTNL2 | BTNL8 | BTNL9 | ERMAP | MOG |
|---|---|---|---|---|---|
| BTNL3 | 35% | 74% | 43% | 41% | 32% |

As shown in FIG. 1, BTNL3, BTNL8, and BTNL9 have similar domain structures. The amino acid sequence of BTNL3 is much more similar to that of BTNL8 than to those of other BTNL proteins.

Beyond levels of sequence identity, certain sites within the BTNL protein family are highly conserved as shown in Table 2 below, which is an alignment of all six human BTNL-like proteins. Beneath the alignment is a consensus sequence (labeled "ALL"). If the consensus amino acid(s) occurs in all proteins in which the amino acid sequence spans the portion of the alignment in which the amino acid occurs, it is shown in bold. If it occurs in all but one of the proteins in which the sequence spans that portion of the alignment, it appears in regular font. If a site has in all cases one of two or more amino acids, each of which are conservative variations of the other, these amino acids are listed below that position in bold font. If a site has in all but one sequence spanning that portion of the alignment one of two or more amino acids, each of which are conservative variations of the other, these amino acids are listed below that position in regular font. The numbering above the alignments in Table 2 is the numbering of SEQ ID NO:2, which is the full length amino acid sequence of human BTNL3, including the signal sequence, which ends at position 17 of SEQ ID NO:2.

TABLE 2

Alignment and consensus sequence of BTNL proteins

```
                                                                         21
BTNL3   ~~~~~~~~~~ ~~~~~~~~~~ ~~~~~~~~~M AFVLILVLSF YELVSGQWQV
BTNL8   ~~~~~~~~~~ ~~~~~~~~~~ ~~~~~~~~~M ALMLSLVLSL LKLGSGQWQV
BTNL9   ~~~~~~~~~~ MVDLSVSPDS LKPVSLTSSL VFLMHLLLLQ PGEPSSEVKV
ERMAP   ~~~~~~~~~~ ~~~~MEMASS AGSWLSGCLI PLVFLRLSVH VSGHAGD...
MOG     ~~~~~~~~~~ ~~~~~~MASL SRPSLPSCLC SFLLLLLLQV SSSYAGQFRV
```

TABLE 2-continued

Alignment and consensus sequence of BTNL proteins

```
BTNL2      YAEATLVVRN ASAESVSCLV HNPVLTEEKG SVISLPEKLQ TELAS..LKV
ALL                                         L              S   QV
                                            F              A   K
                                            V                  R 22                                                 68
BTNL3      TGPGKFVQAL VGEDAVFSCS LFPETSAEAM EVRFFRNQF. ...HAVVHLYR
BTNL8      FGPDKPVQAL VGEDAAFSCF LSPKTNAEAM EVRFFRGQF. ...SSVVHLYR
BTNL9      LGPEYPILAL VGEEVEFPCH LWPQLDAQQM EIRWFRSQT. ...FNVVHLYQ
ERMAP      AGKFHV..AL LGGTAELLCP LSLWPGTVPK EVRWLRSPFP QRSQAVHIFR
MOG        IGPRHPIRAL VGDEVELPCR ISPGKNATGM EVGWYRPPF. ...SRVVHLYR
BTNL2      NGPSQPILVR VGEDIQLTCY LSPKANAQSM EVRWDRS... HRYPAVHVYM
ALL        GP    I AL VGEDA F C  L P    A M EVRW R        VVHLYR
              V  V    L DEV L    I      T   I F           AI IFQ
                      I           I         T                 V 69                                                118
BTNL3      DGEDWESKQM PQYRGRTEFV KDSIAGGRVS LRLKNITPSD IGLYGCWFSS
BTNL8      DGKDQPFMQM PQYQGRTKLV KDSIAEGRIS LRLENITVLD AGLYGCRISS
BTNL9      EQQELPGRQM PAFRNRTKLV KDDIAYGSVV LQLHSIIPSD KGTYGCRFHS
ERMAP      DGKDQDEDLM PEYKGRTVLV RDA.QEGSVT LQILDVRLED QGSYRCLIQV
MOG        NGKDQDGDQA PEYRGRTELL KDAIGEGKVT LRIRNVRFSD EGGFTCFFRD
BTNL2      DGDHVAGEQM AEYRGRTVLV SDAIDEGRLT LQILSARPSD DGQYRCLFEK
ALL        DG D    QM P YRGRT LV KDSI  G VT LRL  I   D   G Y C F
           E  E       A FK    FL R A    IS  QI  V               F   I
                        Q            L       A 119                                               168
BTNL3      QIYDEEATWE LRVAALGSLP LISIVGYVDG GIQLLCLSSG WFPQPTAKWK
BTNL8      QSYYQKAIWE LQVSALGSVP LISITGYVDR DIQLLCQSSG WFPRPTAKWK
BTNL9      DNFSGEALWE LEVAGLGSDP HLSLEGFKEG GIQLRLRSSG WYPKPKVQWR
ERMAP      GNLSKEDTVI LQVAA....P SV........ .......... GSLSPGV...
MOG        HSYQEEAAME LKVED....P FY........ .......... W.VSPGV...
BTNL2      DDVYQEASLD LKVVGLGSSP LITVEGQEDG EMQPMCSSDG WFPQPHVPWR
ALL                   EA  E L V     P                    W   P A
                         D                                        V 169                                               216
BTNL3      GPQGQDLSSD SRANA.DGYS LYDVEISIIV QENA.GSILC SIHLAEQSHE
BTNL8      GPQGQDLSTD SRTNR.DMHG LFDVEISLTV QENA.GSISC SMRHAHLSRE
BTNL9      DHQGQCLPPE FEAIVWDAQD LFSLETSVVV RAGALSNVSV SIQNLLLSQK
ERMAP      .......... ........VA LAVILPVLVL LIMVCLCLIW KQRRAKEKLL
MOG        .......... ........LV LLAVLPVLLL QITVGLVFLC LQYRLRGKLR
BTNL2      DMEGKTIPSS SQALTQGSHG LFHVQTLLRV TNISAVDVTC SISIPFLGEE
ALL                              LF V   L V     A    I
                                 L L    V L     V    V
                                 Y I    I            L
                                 A                   F 217                                               254
BTNL3      VESKVLIGET FFQ.PSPWR. ...LASILLGL LCGALCGVVM ........GM
BTNL8      VESRVQIGDT FFE.PISWH. ...LATKVLGI LCCGLFFGIV ........GL
BTNL9      KELVVQIADV FVPGASAWKS AFVATLPLLL VLAALALGVL RKQRRSREKL
ERMAP      YEHVTEVDNL L......... .......... .......... SDHAKE....
MOG        AE.IENLHRT F......... .......... .......... DPHFLRVPCW
BTNL2      KIATFSLSES ..RMTFLWKT LLVWGLLLAV AVGLPRKRS~ ~~~~~~~~~~
ALL              E    I
                       V
                       L 255                                               297
BTNL3      IIVFFKSK.. .....GKIQA ELDWRRKHGQ AELRDARKHA VEVTLDPETA
BTNL8      KIFFSKFQ.. .....WKIQA ELDWRRKHGQ AELRDARKHA VEVTLDPETA
BTNL9      RKQAEKRQEK LTAELEKLQT ELDWRRAEGQ AEWRAAQKYA VDVTLDPASA
ERMAP      KGKLHKAVKK LRSELK.... ...LKRAAAN SGWRRARLHL VAVTLDPDTA
MOG        KITLFVIVPV LGPLVALIIC YNWLHRRLAG QFLEELLFHL EALSG~~~~~
BTNL2      ~~~~~~~~~~ ~~~~~~~~~~ ~~~~~~~~~~ ~~~~~~~~~~ ~~~~~~~~~~
ALL        K    F              RR    GQ     R AR HA  V VTLDPETA
           R    L              K     AN     LQ    L     LS  DS
                A              H              F 298                                               344
BTNL3      HPKLCVS.DL KTVTHRKAPQ .EVPHSEKRF TRKSVVAS.Q GFQAGKHYWE
BTNL8      HPKLCVS.DL KTVTHRKAPQ .EVPHSEKRF TRKSVVAS.Q SFQAGKHYWE
BTNL9      HPSLEVSEDG KSVSSRGAPP GPAPGHPQRF SEQTCALSLE RFSAGRHYWE
ERMAP      HPKLILSEDQ RCV.RLGDRR QPVPDNPQRF DFVVSILGSE YFTTGCHYWE
MOG        ~~~~~~~~~~ ~~~~~~~~~~ ~~~~~~~~~~ ~~~~~~~~~~ ~~~~~~~~~~
BTNL2      ~~~~~~~~~~ ~~~~~~~~~~ ~~~~~~~~~~ ~~~~~~~~~~ ~~~~~~~~~~
```

TABLE 2-continued

Alignment and consensus sequence of BTNL proteins

| | | | | | | | | |
|---|---|---|---|---|---|---|---|---|
| ALL | HPKL VS D | KTV HR APQ | VP | KRF | T KS VAS | | F AGKHYWE | |
| | L | S R | R | A | Q | S QT AL | | R |
| | | | | | | I | | |

|       | 345 | | | | 394 |
|-------|-----|-----|-----|-----|-----|
| BTNL3 | VDVGQNVGWY | VGVCRDDVDR | GKNNVTLSPN | NGYWVLRLTT | EHLYFTFNPH |
| BTNL8 | VDGGHNKRWR | VGVCRDDVDR | RKEYVTLSPD | HGYWVLRLNG | EHLYFTLNPR |
| BTNL9 | VHVGRRSRWF | LGACLAAVPR | A.GPARLSPA | AGYWVLGLWN | GCEYFVLAPH |
| ERMAP | VYVGDKTKWI | LGVCSESVSR | .KGKVTASPA | NGHWLLRQSR | GNEYEALTSP |
| MOG   | ~~~~~~~~~~ | ~~~~~~~~~~ | ~~~~~~~~~~ | ~~~~~~~~~~ | ~~~~~~~~~~ |
| BTNL2 | ~~~~~~~~~~ | ~~~~~~~~~~ | ~~~~~~~~~~ | ~~~~~~~~~~ | ~~~~~~~~~~ |
| ALL   | V VGQN RW | VGVC D V R | K VTLSP | NGYWVLRL | H LF L PH |
|       | HR K | L A E | A A | H | N F R |
|       | RK | | | | |

|       | 395 | | | | 444 |
|-------|-----|-----|-----|-----|-----|
| BTNL3 | FISLPPSTPP | TRVGVFLDYE | GGTISFFNTN | DQSLIYTLLT | CQFEGLLRPY |
| BTNL8 | FISVFPRTPP | TKIGVFLDYE | CGTISFFNIN | DQSLIYT.LT | CRFEGLLRPY |
| BTNL9 | RVALTLRVPP | RRLGVFLDYE | AGELSFFNVS | DGSHIFTFHD | .TFSGALCAY |
| ERMAP | QTSFRLKEPP | RCVGIFLDYE | AGVISFYNVT | NKSHIFTF.T | HNFSGPLRPF |
| MOG   | ~~~~~~~~~~ | ~~~~~~~~~~ | ~~~~~~~~~~ | ~~~~~~~~~~ | ~~~~~~~~~~ |
| BTNL2 | ~~~~~~~~~~ | ~~~~~~~~~~ | ~~~~~~~~~~ | ~~~~~~~~~~ | ~~~~~~~~~~ |
| ALL   | SL R PP | RVGVFLDYE | G ISFFN | DQS IYT T | QF G LRPY |
|       | V K | KI I | L Y | K F | N F |
|       | F | L | | | R |

|       | 445 | | 466 | | |
|-------|-----|-----|-----|-----|-----|
| BTNL3 | IQHAMYD.EE | KGTPIFICPV | SWG~~~~~~~ | ~~~~~~~~~~ | ~~~~~~~~~~ |
| BTNL8 | IEYPSYN.EQ | NGTPIVICPV | TQESEKEASW | QRASAIPETS | NSESSSQATT |
| BTNL9 | FRPRAHDGGE | HPDPLTICPL | P......... | VRGTGVPEEN | DSDTWLQPYE |
| ERMAP | FEPCLHDGGK | NTAPLVICSE | LHKSEESIVP | RPEGKGHANG | DVSLKVNSSL |
| MOG   | ~~~~~~~~~~ | ~~~~~~~~~~ | ~~~~~~~~~~ | ~~~~~~~~~~ | ~~~~~~~~~~ |
| BTNL2 | ~~~~~~~~~~ | ~~~~~~~~~~ | ~~~~~~~~~~ | ~~~~~~~~~~ | ~~~~~~~~~~ |
| ALL   | I M D | K PIFICPV | E | R SAIPE | DSES QAT |
|       | F A | N LV L | | TGV | DT NPS |
|       | L | H | | G | |

|       | | | | |
|-------|-----|-----|-----|-----|
| BTNL3 | ~~~~~~~~~~ | ~~~~~~~~~~ | ~~~~~~~~~~ | ~ |
| BTNL8 | PFLPRGEM~~ | ~~~~~~~~~~ | ~~~~~~~~~~ | ~ |
| BTNL9 | PADPALDWW~ | ~~~~~~~~~~ | ~~~~~~~~~~ | ~ |
| ERMAP | LPPKAPELKD | IILSLPPDLG | PALQELKAPS | F |
| MOG   | ~~~~~~~~~~ | ~~~~~~~~~~ | ~~~~~~~~~~ | ~ |
| BTNL2 | ~~~~~~~~~~ | ~~~~~~~~~~ | ~~~~~~~~~~ | ~ |
| ALL   | PF PA EM | | | |
|       | A DL | | | |

One of skill in the art will appreciate that the consensus sequence among these proteins reflects features that may be important for the structures or functions of these proteins. Given their varying expression patterns, it is likely that these proteins do not have identical functions, and thus, it is unlikely that all amino acids important for the function of each protein would be conserved within the family. However, many of the conserved amino acids may be important to maintain the proper structure, which is, of course, necessary for function. At many sites one of two or more amino acids that are conservative variations of each other occurs in all or most members of the BTNL family. One of skill in the art would understand that such conservative variations in BTNL3 would likely not adversely affect function. For example, at position 36 of SEQ ID NO:2 (which has the same numbering as the alignment of Table 2 above), various members of the BTNL family have one of three different hydrophobic amino acids, alanine (BTNL3, BTNL8, and ERMAP), isoleucine (BTNL2), or valine (BTNL3 and MOG). One of skill in the art would understand that a change from valine to alanine or isoleucine at this position of the BTNL3 amino acid sequence would be unlikely to affect function. Similar considerations would apply at all of the sites where conservative variations occur within the family. Thus, a BTNL3 protein, as meant herein, includes proteins comprising SEQ ID NO:2, or a fragment thereof, wherein the sequence may be altered by conservative variation at a site where conservative variation occurs among members of the BTNL family and wherein the protein can inhibit the proliferation of T cells as measured by the method described in the examples below. Such sites include, for example, positions 3, 16, 20, 28, 30, 32, 34, 35, 36, 38, 42, 48, 53, 55, 63, 64, 66, 67, 68, 69, 72, 79, 81, 82, 87, 88, 89, 91, 97, 98, 100, 101, 104, 112, 116, 128, 165, 189, 191, 195, 197, 201, 204, 223, 255, 258, 272, 276, 277, 283, 284, 287, 290, 291, 303, 308, 311, 316, 318, 323, 326, 328, 329, 331, 332, 340, 349, 350, 352, 355, 357, 360, 369, 371, 375, 386, 391, 394, 398, 401, 406, 407, 409, 418, 421, 426, 430, 436, and 444 of SEQ ID NO:2. Further, variations may also be tolerated at other sites within BTNL3 without effect on function. For example conservative substitutions at non-conserved positions would be unlikely to affect function.

Thus, a BTNL3 protein, as meant herein, includes proteins that (1) have naturally-occurring polymorphisms or recombinantly-introduced amino acid changes, (2) are at least 90%, 95%, 96%, 97%, 98% or 99% identical to SEQ ID NO:2 and/or to amino acids 18-236 of SEQ ID NO:2 and/or to amino acids 18-166 of SEQ ID NO:9, and (3) retain the ability to attenuate T cell proliferation as measured by the methods described herein or act as an inhibitor of native BTNL3. Some such polymorphisms may enhance the ability of a BTNL3 protein to inhibit T cell proliferation and/or may make a BTNL3 protein easier to produce in a commercial production process. Other such polymorphisms may produce an inhibitor of native BTNL3. These polymorphisms can occur at sites within BTNL3 that are not conserved such as, for example, position 22, 25, 26, 27, 29, 37, 39, 41 43, 45, 46, 47, and any other site shown to be nonconserved in Table 2.

The expression patterns and biological functions of the BTNL proteins have been explored to some extent in some cases, but not in others. ERMAP is expressed on the surface of red blood cells and has not been assigned a specific biological function. MOG is a component of the myelin sheath. Neither ERMAP nor MOG is thought to play a role in the immune system, although antibodies to MOG are often detected in patients with multiple sclerosis. BTN1 is homologous to MOG, and BTN1 is found in cow's milk. It has been hypothesized that human consumption of cow's milk may lead to the development of antibodies to BTN1 that cross-react with human MOG, thus leading to autoimmune diseases such as multiple sclerosis. See Guggenmos et al. (2004), J. Immunol. 172: 61-68. BTNL2 has been shown to inhibit T cell proliferation and cytokine secretion, but not B cell proliferation. Thus, BTNL2 is thought to act as a negative co-regulator of T-cell mediated events. See, e.g., U.S. Pat. No. 7,244,822, the relevant portions of which are incorporated herein by reference. A polymorphism in BTNL2 has been clearly linked to sarcoidosis, suggesting that BTNL2 may play a role in either initiating or mediating or contributing or responding to this disease. Valentonyte et al. (2005), Nature Genetics 37(4): 357-64. More tentative associations have been drawn between various BTNL2 polymorphisms and ulcerative colitis, rheumatoid arthritis, spontaneous inclusion body myositis, systemic lupus erythematosus, type I diabetes, tuberculoid leprosy, and antigen-specific IgE responsiveness. Arnett et al. (2009), Cytokine 46: 370-75.

Levels of RNAs encoding the various BTNL proteins in various cell types and tissues have been reported. BTNL3 is expressed in ileum, small intestine, colon, liver, lung, bone marrow, and spleen. Arnett et al. (2009), Cytokine 46: 370-375. Among various cell types associated with immune function that have been tested for BTNL3 expression, BTNL3 RNA is expressed predominantly in neutrophils. Arnett et al. (2009), Cytokine 46: 370-75. The expression of BTNL3 RNA in cells involved in immune function suggests that BTNL3 may play a role in immune function, either by driving the inflammatory response or in dampening the response following a flare.

BTNL3 Protein

The instant invention encompasses secreted, soluble versions of BTNL3, which can, optionally, be immobilized by attachment to a surface such as a nanoparticle, a bead, or a microtiter plate, as well as versions comprising a transmembrane domain that can be expressed on a cell surface. Such BTNL3 proteins can inhibit the proliferation of a T cell stimulated by an immobilized anti-CD3 antibody. Some variant BTNL3 proteins also have this activity, although variants that antagonize this inhibition are also contemplated. Such proteins can be isolated, that is, be part of a purified protein preparation in which the BTNL3 protein constitutes at least 80% or at least 90% of the protein present in the preparation. The invention further includes BTNL3 proteins encoded by the BTNL3 nucleic acids described below. A BTNL3 protein, as meant herein, encompasses a protein comprising the amino acid sequence of SEQ ID NO:2, 6, 7, or 9, as well as fragments, derivatives, and variants thereof, including fusion proteins and multimers, as discussed above and below. The amino acid sequences of SEQ ID NO:2, 6, and 9 include a signal sequence starting at position 1 and ending at a position from about position 15 to about position 20, optionally at position 17. Thus, the amino acid sequence of the mature BTNL3 begins at a position from about 16 to about position 21 of SEQ ID NO:2, 6, or 9. Optionally, the mature amino acid sequence of BTNL3 begins at position 18 of SEQ ID NO:2, 6, or 9.

The signal sequence of BTNL3 is followed by an Ig-like domain extending from about position 25 to about position 131 of SEQ ID NO:2, 6, or 9. The following region, from about position 132 to about position 236 of SEQ ID NO:2 or 6, aligns with IgC-like domains in BTNL2, but lacks some of the characteristic sequence features commonly found in a IgC1-like domain. See, e.g., Williams and Barclay (1988), Ann. Rev. Immunol. 6: 381-405; Peach et al. (1995), J. Biol. Chem. 270(36): 21181-21187. This domain is substantially shortened in the amino acid sequence of SEQ ID NO:9, which is the amino acid sequence encoded by a splice variant of BTNL3. The transmembrane domain of BTNL3 begins at about position 237 of SEQ ID NO:2 or about position 167 or SEQ ID NO: 9 and ends at about position 259 of SEQ ID NO:2 or about position 189 of SEQ ID NO:9. The intracellular portion of BTNL3 begins at about position 260 and ends at position 466 of SEQ ID NO:2 or begins at about position 190 and ends at position 432 of SEQ ID NO:9. The intracellular region contains a B30.2 domain extending from about position 288 to about position 445 of SEQ ID NO:2 or about position 254 to position 411 of SEQ ID NO:9. A B30.2 domain is a globular domain of approximately 170 amino acids. Henry et al. (supra) discuss B30.2 domains in some detail and provide an alignment of a number of B30.2 domains and a consensus sequence derived from the alignment. The portions of Henry et al. (1998), Mol. Biol. Evol. 15(12): 1696-1705 that show (by sequence comparison) and explain what a B30.2 domain are incorporated herein by reference. B30.2 domains are also found in BTNL9, BTNL8, and ERMAP, all of which are members of the butyrophilin-like family of proteins, as discussed herein. The alignment of BTNL proteins in Table 2 above from about position 288-445 exhibits a high degree of homology, certainly higher than is observed between the more disparate collections of proteins containing B30.2 domains aligned by Henry et al. supra.

Similarly, the protein having the amino acid sequence of SEQ ID NO:9 includes a signal sequence starting at position 1 and ending at a position from about position 15 to about position 20, optionally at position 17. Thus, the amino acid sequence of the mature protein begins at a position from about 16 to about position 21 of SEQ ID NO:2. Optionally, the mature amino acid sequence begins at position 18 of SEQ ID NO:9. This is followed by an IgV-like domain extending from about 25 to 131 of SEQ ID NO:9. The majority of the following domain present in SEQ ID NO:2 is missing is SEQ ID NO:9. The transmembrane domain begins at about position 167 of SEQ ID NO:9 and extends to about position 189 of SEQ ID NO:9. Beginning at about 10 amino acids beyond the transmembrane domain, SEQ ID NO:9 includes a stretch of 36 amino acids not found in SEQ ID NO:2. The B30.2 domain begins at about position 254 of SEQ ID NO:9 and ends at about position 411 of SEQ ID NO:9.

BTNL3 proteins, as meant herein, include hetero- and homo-multimers comprising at least two BTNL3 proteins. In some embodiments, biologically active multimers can be homomultimers. The size of such homomultimers can be determined by polyacrylamide gel electrophoresis under non-reducing conditions or by size exclusion chromatography. The size of the monomeric BTNL3 protein contained in such multimers can be determined by polyacrylamide gel electrophoresis of the multimer under reducing conditions. Such conditions would be expected to break disulfide bridges and interfere with non-covalent interactions such as hydrogen bonds or charge interactions. Thus, multimers held together by disulfide bonds or non-covalent interactions would be expected to be reduced to monomers under reducing conditions. In some embodiments, the size of the biologically active BTNL3 homomultimer can be at least about two, three, four, five, six, seven, eight, nine, ten, eleven, twelve, thirteen, fourteen, fifteen or sixteen times the size of the monomeric BTNL3 protein. In some embodiments, the size of such a homomultimer can be no more than about two, three, four, five, six, seven, eight, nine, ten, eleven, twelve, thirteen, fourteen, fifteen or sixteen times the size of the monomeric BTNL3 protein.

BTNL3 proteins, as meant herein, also include proteins encoded by splice variants of the full length BTNL3 mRNA. The cDNA coding sequence for BTNL3 extends from position 1-1401 of SEQ ID NO:1, the last three nucleotides being a stop codon. The coding sequence starts within the first exon. The most common splice variant contains eight exons: exon 1, encoding amino acids 1-16 of SEQ ID NO:2; exon 2, encoding amino acids 17-132 of SEQ ID NO:2; exon 3, encoding amino acids 133-224 of SEQ ID NO:2; exon 4, encoding amino acids 225-262 of SEQ ID NO:2; exon 5, encoding amino acids 263-269 of SEQ ID NO:2; exon 6, encoding amino acids 270-278 of SEQ ID NO:2; exon 7, encoding amino acids 279-287 of SEQ ID NO:2; and exon 8, encoding amino acids 288-466. However, alternative splicing can generate different messages including different exons. One of these was cloned by Shibui and coworkers. Shibui et al. (1999), J. Hum. Genet. 44: 249-252. The amino acid sequence reported in Shibui et al. from clone ColF4100 is incorporated by reference herein. The cDNA sequence encoding this amino acid sequence from GenBank Accession no. AB020625 is also incorporated herein by reference. The protein encoded by this splice variant lacks a portion of SEQ ID NO:2 encoded by the third and fourth exons. Hence, the encoded protein is missing the majority of the second Ig-like domain of mature BTNL3 protein. Compare SEQ ID NO:2 to SEQ ID NO:9. Moreover, the intracellular region of SEQ ID NO:9 includes sequences not found in SEQ ID NO:2 (residues 200-235 of SEQ ID NO:9). Both the insertion and deletion of extra amino acids in this splice variant are a result from the use of non-canonical splice sites. SEQ ID NO:9, like SEQ ID NO:2, contains a signal sequence ending at a residue from 16 to 21 of SEQ ID NO:9, optionally at residue 17.

Other splice variants might be formed. For example, a splice variant missing either of exons 2 or 3, that is one of exons encoding either of the two extracellular domains, is contemplated. Similarly, splice variants missing any of exons 5, 6, 7, or 8 are contemplated. BTNL3 proteins, as meant herein, can be encoded by splice variants that are missing various exons. Splice variants can, in addition, use cryptic splice sites.

In some embodiments, a BTNL3 protein can be a soluble fragment of the full length transmembrane protein comprising SEQ ID NO:2 or SEQ ID NO:9, or a variant thereof. In some embodiments, a BTNL3 protein comprises a fragment of BTNL3 comprising the immunoglobulin-like domain extending from residue 12, 13, 14, 15, 16, 17, 18, 19, 20, 21, 22, 23, 24, 25, 26, 27, 28, 29, or 30 of SEQ ID NO:2 or SEQ ID NO:9 to residue 120, 121, 122, 123, 124, 125, 126, 127, 128, 129, 130, 131, 132, 133, 134, 135, 136, 137, 138, 139, or 140 of SEQ ID NO:2 or SEQ ID NO:9. Such embodiments may or may not include all of the following domain extending from residue 121, 122, 123, 124, 125, 126, 127, 128, 129, 130, 131, 132, 133, 134, 135, 136, 137, 138, 139, or 140 of SEQ ID NO:2 to residue 230, 231, 232, 233, 234, 235, 236, 237, or 238 of SEQ ID NO:2. For example, SEQ ID NO:9 lacks the amino acids present at positions 158 to 227 of SEQ ID NO:2. Variants lacking other portions of this domain are also contemplated. In further embodiments, a BTNL3 protein can comprise a fragment extending from residue 121, 122, 123, 124, 125, 126, 127, 128, 129, 130, 131, 132, 133, 134, 135, 136, 137, 138, 139, or 140 of SEQ ID NO:2 to residue 220, 221, 222, 223, 234, 235, 236, 237, 238, 239, 230, 231, 232, 233, 234, 235, 236, 237, or 238 of SEQ ID NO:2. Such embodiments may or may not include the preceding domain extending from residue extending from residue 12, 13, 14, 15, 16, 17, 18, 19, 20, 21, 22, 23, 24, 25, 26, 27, 28, 29, or 30 of SEQ ID NO:2 to residue 120, 121, 122, 123, 124, 125, 126, 127, 128, 129, 130, 131, 132, 133, 134, 135, 136, 137, 138, 139, or 140 of SEQ ID NO:2. A BTNL3 protein can comprise a fragment which includes most or all of the extracellular region of BTNL3. Such a protein can comprise an amino acid sequence extending from residue 12, 13, 14, 15, 16, 17, 18, 19, 20, 21, 22, 23, 24, 25, 26, 27, 28, 29, or 30 of SEQ ID NO:2 to residue 220, 221, 222, 223, 234, 235, 236, 237, 238, 239, 230, 231, 232, 233, 234, 235, 236, 237, or 238 of SEQ ID NO:2, optionally from about residue 18 to about residue 236 of SEQ ID NO:2. Alternatively, a soluble BTNL3 protein can comprise a fragment that includes most or all of the extracellular region extending from residue 12, 13, 14, 15, 16, 17, 18, 19, 20, 21, 22, 23, 24, 25, 26, 27, 28, 29, or 30 of SEQ ID NO:9 to residue 155, 156, 157, 158, 159, 160, 161, 162, 163, 164, 165, 166, 167, 168, 169, 170 of SEQ ID NO:9. All of these fragments can contain variations relative to SEQ ID NO:2 or SEQ ID NO:9 and can contain a defined number of substitutions, insertions, or deletions of a single amino acid relative to SEQ ID NO:2 or SEQ ID NO:9 as discussed below. These embodiments can inhibit the proliferation of T cells stimulated by an immobilized anti-CD3 antibody. Some BTNL3 protein variants that do not comprise the amino acid sequence of amino acids 18-236 of SEQ ID NO:2 or amino acids 18-166 of SEQ ID NO:9 may antagonize the inhibition of the proliferation of T cells stimulated by an immobilized anti-CD3 antibody.

The invention encompasses epitopes of BTNL3 proteins that are useful for generating antibodies, which are referred to herein as immunogenic fragments Immunogenic fragments are preferably at least 10 amino acids long and can comprise contiguous amino acids from SEQ ID NO:2 or SEQ ID NO:9. Such epitopes can span regions of a BTNL3 protein encoded by a splice junction, which may have the advantage of specific binding to proteins encoded by specific splice variants. In some embodiments the epitope is located within the extracellular region of BTNL3, which extends from about amino acid position 18 to about position 236 of SEQ ID NO:2 or about residue 18 to about residue 166 of SEQ ID NO:9. An epitope can be partially or completely within the first immunoglobulin variable region-like domain, which extends from about amino acid position 25 to position 131 of SEQ ID NO:2 or SEQ ID NO:9. Alternatively, an epitope can be partially or completely within the following domain, which extends from about amino acid position 132 to 236 of SEQ ID NO:2. In SEQ ID NO:9, this domain, which is substantially shortened, extends from about position 132 to 166 of SEQ ID NO:9. This shortened domain can also contain part or all of an epitope to which an antibody binds.

A BTNL3 protein, as meant herein, may contain one or more insertions, deletions, or substitutions of a single amino acid relative to SEQ ID NO:2 or SEQ ID NO:9 or to one of the fragments or portions of SEQ ID NO:2 or SEQ ID NO:9 discussed above. In some embodiments, a BTNL3 protein contains not more than 20, 19, 18, 17, 16, 15, 14, 13, 12, 11, 10, 9, 8, 7, 6, 5, 4, 3, 2, or 1 substitutions, insertions, or deletions of a single amino acid relative to SEQ ID NO:2 or SEQ ID NO:9 or relative to one of the fragments of SEQ ID NO:2 or SEQ ID NO:9 discussed above. Such BTNL3 protein variants within the scope of the invention can retain the ability to attenuate T cell proliferation or can act as an inhibitor or antagonist of this attenuation of T cell proliferation by unaltered BTNL3 protein as assayed by the methods described herein.

In some embodiments the substitutions can be conservative amino acid substitutions. Examples of conservative amino acid substitutions, unlikely to affect biological activity, include the following: alanine for serine, valine for isoleucine, aspartate for glutamate, threonine for serine, alanine for glycine, alanine for threonine, serine for asparagine, alanine for valine, serine for glycine, tyrosine for phenylalanine, alanine for proline, lysine for arginine, aspartate for asparagine, leucine for isoleucine, leucine for valine, alanine for glutamate, aspartate for glycine, and these changes in the reverse. See e.g. Neurath et al., The Proteins, Academic Press, New York (1979), the relevant portions of which are incorporated herein by reference. Further, an exchange of one amino acid within a group for another amino acid within the same group is a conservative substitution, where the groups are the following: (1) alanine, valine, leucine, isoleucine, methionine, norleucine, and phenylalanine; (2) histidine, arginine, lysine, glutamine, and asparagine; (3) aspartate and glutamate; (4) serine, threonine, alanine, tyrosine, phenylalanine, tryptophan, and cysteine; and (5) glycine, proline, and alanine. As discussed above, sites at which conservative substitutions exist within BTNL family members are aligned (as in Table 2) are sites where conservative substitutions are particularly unlikely to affect function. Similarly, highly conserved residues, for example residues 2, 40, 57, and 65, among many others, of SEQ ID N0:2, are likely to be less tolerant of substitution.

A BTNL3 protein or variant thereof can be at least 85%, 90%, 95%, 96%, 97%, 98%, or 99% identical to SEQ ID N0:2 or SEQ ID N0:9, wherein the alignment window is at least 50, 60, 75, 80, 90, or 100 amino acids long, and wherein the BTNL3 protein can inhibit the proliferation of T cells activated with an immobilized anti-CD3 antibody. As discussed above, sequence mismatches with other human BTNL family members can guide one of skill in the art as to where modifications in the sequence of SEQ ID N0:2 or SEQ ID N0:9 can be made without affecting function. In some embodiments, the insertions, deletions, or substitutions can occur at, or adjacent to, residues that are not conserved among human BTNL family members. See Table 2. In some embodiments, these alterations occur at (in the case of deletions or substitutions) or adjacent to (in the case of insertions) one or more of the following non-conserved residues of SEQ ID N0:2: 22, 25-27, 29, 37. 39. 41, 43, 45-47, 49, 50, 56, 58-62, 71, 73-76, 80, 86, 93, 94, 96, 102, 103, 105-107, 109, 111, 113, 115, 117-123, 126, 127, 130, 132-137, 139-158, 160-162, 164, 166-187, 190, 192-194, 196, 198-200, 202-203, 205-217, 219-222, and/or 224-236. Alterations at the analogous sites in SEQ ID N0:9, where such analogous sites exist, are also contemplated. Alternatively, a BTNL3 protein can contain not more than 1, 2, 3, 4, 5, 6, 8, 10, 15, 20, 25, or 30 amino acid substitutions, deletions, or insertions relative to SEQ ID N0:2 or SEQ ID N0:9. The proteins described above are BTNL3 proteins or variants thereof as meant herein as long as they can inhibit the proliferation of T cells activated by an immobilized anti-CD3 antibody or antagonize such inhibition by a BTNL3 protein comprising the amino acid sequence of SEQ ID NO:7.

BTNL3 proteins may be glycosylated to varying degrees or not glycosylated. As an illustration, a BTNL3 protein may comprise one or more N- or O-linked glycosylation sites in addition to those already found in a protein comprising SEQ ID NO:2 or SEQ ID NO:9. SEQ ID NO:2 contains two potential N-linked glycosylation sites at positions 103 and 368. SEQ ID NO:9 contains the potential N-linked glycosylation sites at position 103 and 334. The potential N-linked glycosylation site at position 103 of SEQ ID NO:2 or 9 is also present in BTNL8, the BTNL protein most closely related to BTNL3. Thus, this glycosylation site may play a role in BTNL3 function or structure. One of skill in the art would be aware that asparagine residues that are part of the sequence Asn Xxx Ser/Thr (where Xxx is any amino acid except proline) can serve as sites of addition for N-glycans. In addition, there are many serine and threonine residues that may serve as O-linked glycosylation sites. Glycosylation may increase in vivo half life or alter biological activity. Variants of BTNL3 proteins also include proteins comprising one, two, three, four, five, six, seven, eight, nine, or ten more N-and/or O-linked glycosylation sites than are present in SEQ ID NO:2 as long as the resulting protein can inhibit the proliferation of T cells. Variant BTNL3 proteins also include those that have one, two, three, four, or five fewer N- and/or O-linked glycosylation sites than are present in SEQ ID NO:2 as long as they can inhibit the proliferation of T cells activated with an immobilized anti-CD3 antibody or can inhibit the ability of unmutated versions of BTNL3 protein to do so.

BTNL3 proteins, as meant herein, can be fusion proteins comprising at least one BTNL3 polypeptide, which can comprise an amino acid sequence that is a variant and/or a fragment of SEQ ID NO:2 or SEQ ID NO:9 (as explained above), and at least one other moiety. The other moiety can be a polypeptide other than a BTNL3 protein. The other moiety can also be a non-protein moiety such as, for example, a polyethylene glycol (PEG) moiety or a cytotoxic, cytostatic, luminescent, and/or radioactive moiety.

Attachment of PEG has been shown to increase the in vivo half life of at least some proteins. Moreover, cytotoxic, cytostatic, luminescent, and/or radioactive moieties have been fused to antibodies for diagnostic or therapeutic purposes, for example, to locate, to inhibit proliferation of, or to kill cells to which the antibodies can bind. Similarly, BTNL3 proteins fused to such moieties can be used to locate, to inhibit proliferation of, or to kill cells that BTNL3 can bind to, for example, cells involved in immune response. Among such cytotoxic, cytostatic, luminescent, and/or radioactive moieties are, for example, maytansine derivatives (such as DM1), enterotoxins (such as a Staphylococcal enterotoxin), iodine isotopes (such as iodine-125), technetium isotopes (such as Tc-99m), cyanine fluorochromes (such as Cy5.5.18), ribosome-inactivating proteins (such as bouganin, gelonin, or saporin-S6), and calicheamicin, a cytotoxic substance that is part of a product marketed under the trademark MYLOTARG™ (Wyeth-Ayerst).

A variety of polypeptides other than BTNL3 can be fused to a BTNL3 polypeptide for a variety of purposes such as, for example, to increase in vivo half life of the protein, to facilitate identification, isolation and/or purification of the protein, to increase the activity of the protein, and to promote oligomerization of the protein.

Many polypeptides can facilitate identification and/or purification of a recombinant fusion protein of which they are a part. Examples include polyarginine, polyhistidine, or HAT™ (Clontech), which is a naturally-occurring sequence of non-adjacent histidine residues that possess a high affinity for immobilized metal ions. BTNL3 proteins comprising these polypeptides can be purified by, for example, affinity chromatography using immobilized nickel or TALON™ resin (Clontech), which comprises immobilized cobalt ions. See e.g. Knol et al. (1996), J. Biol. Chem. 27(26): 15358-15366. Polypeptides comprising polyarginine allow effective purification by ion exchange chromatography. Other useful polypeptides include, for example, the antigenic identification peptides described in U.S. Pat. No. 5,011,912 and in Hopp et al. (1988), Bio/Technology 6:1204. One such peptide is the FLAG® peptide, which is highly antigenic and provides an epitope reversibly bound by a specific monoclonal antibody, enabling rapid assay and facile purification of expressed recombinant fusion protein. A murine hybridoma designated 4E11 produces a monoclonal antibody that binds the FLAG® peptide in the presence of certain divalent metal cations, as described in U.S. Pat. No. 5,011,912. The 4E11 hybridoma cell line has been deposited with the American Type Culture Collection under Accession No. HB 9259. Monoclonal antibodies that bind the FLAG® peptide can be used as affinity reagents to recover a polypeptide purification reagent that comprises the FLAG® peptide. Other suitable protein tags and affinity reagents are: 1) those described in GST-BindTm system (Novagen), which utilizes the affinity of glutathione-S-transferase fusion proteins for immobilized glutathione; 2) those described in the T7-TAG® affinity purification kit (Novagen), which utilizes the affinity of the amino terminal 11 amino acids of the T7 gene 10 protein for a monoclonal antibody; or 3) those described in the STREP-T AG® system (Novagen), which utilizes the affinity of an engineered form of streptavidin for a protein tag. Some of the above-mentioned protein tags, as well as others, are described in Sassenfeld (1990), TIBTEC$_H$ 8: 88-93, Brewer et al., in *Purification and Analysis of Recombinant Proteins*, pp. 239-266, Seetharam and Sharma (eds.), Marcel Dekker, Inc. (1991), and Brewer and Sassenfeld, in *Protein Purification Applications*, pp. 91-111, Harris and Angal (eds.), Press, Inc., Oxford England (1990). The portions of these references that describe protein tags are incorporated herein by reference. Further, fusions of two or more of the tags described above, such as, for example, a fusion of a FLAG tag and a polyhistidine tag, can be fused to a BTNL3 protein of the invention.

Recombinant fusion proteins comprising polypeptides other than BTNL3 may have other kinds of unique advantages, such as, for example, a propensity to form dimers, trimers, or higher order multimers, an increased in vivo half-life, and/or an increased biological activity. A "higher order multimer" when used in conjunction with, for example, "dimer," means a multimer containing more than two polypeptide chains. When used in a phrase like "a trimer or a higher order multimer," the higher order multimer contains more than three polypeptide chains. Thus, a higher order multimer is one that has more polypeptide chains than the multimer it is compared to. Techniques for preparing fusion proteins are known, and are described, for example, in International Application WO 99/31241 and in Cosman et al. ((2001). Immunity 14: 123-133).

As an illustration, a polypeptide that comprises an Fc region of an antibody, optionally an IgG antibody, or a substantially similar protein, can be fused to a BTNL3 polypeptide or fragment thereof. An Fc region of an antibody is a polypeptide comprising the most or all of hinge plus the $C_H2$, and the $C_H3$ domains from an antibody or immunoglobulin domains substantially similar to these. For discussion, see Hasemann and Capra, Immunoglobulins: Structure and Function, in William E Paul, ed., Fundamental Immunology, Second Edition, 212-213 (1989). The Fc fragment can be a human IgG Fc, such as an IgG1, IgG2, IgG3, or IgG4 Fc. An Fc fragment can be a native human or animal Fc fragment. Truncated forms of Fc regions, that is, forms missing some portion of the hinge, $C_H2$, and/or $C_H3$ domains, that promote dimerization can also be used. Other portions of antibodies and other immunoglobulin isotypes can be used. Recombinant fusion proteins comprising Fc regions of antibodies are likely to form dimers or higher order multimers. Fusion proteins comprising various portions of antibody-derived proteins have been described by Ashkenazi et al. ((1991) Proc. Natl. Acad. Sci. USA 88:10535-39), Byrn et al. ((1990), Nature 344: 677-70), Hollenbaugh and Aruffo (in Current Protocols in Immunology, Suppl. 4, pp. 10.19.1-10.19.11 (1992)), Baum et al. ((1994), EMBO J. 13: 3992-4001) and in U.S. Pat. No. 5,457,035 and International Application WO 93/10151, the relevant portions of which are incorporated herein by reference. In some embodiments, an altered Fc region can have the advantage of having a lower affinity for Fc receptors compared to a wild type Fc region. This can be an advantage because it may lessen the lysis of cells to which such recombinant fusion proteins bind by immune effector cells. Such alterations to the Fc region are described in U.S. Pat. No. 5,457,035 and International Patent Application WO 93/10151, the relevant portions of which are incorporated herein by reference. Example 2 below describes the production of a fusion protein containing the extracellular region of human BTNL3 and the Fc region of a human IgG1 antibody.

Alternatively, a BTNL3 fusion protein can comprise all or part of a BTNL3 polypeptide as described herein plus a non-Fc polypeptide that has the effect of increasing the half life of the fusion protein such as, for example, a serum albumin protein, optionally a human protein, or a fragment thereof, or a protein that binds to serum albumin or a fragment thereof. In some embodiments this additional polypeptide could be all or part of a fibronectin protein, which is, optionally a human protein.

A recombinant fusion protein comprising a BTNL3 protein can comprise a polypeptide comprising a leucine zipper. Among known leucine zipper sequences are sequences that promote dimerization and sequences that promote trimerization. See e.g. Landschulz et al. (1988), Science 240: 1759-64, the relevant portions of which is incorporated herein by reference. Leucine zippers comprise a repetitive heptad repeat, often with four or five leucine residues interspersed with other amino acids. Use and preparation of leucine zippers are well known in the art. A BTNL3 fusion protein can comprise one or more peptide linkers. Generally, a peptide linker is a stretch of amino acids that serves to link plural polypeptides to form multimers and provides the flexibility or rigidity required for the desired function of the linked portions of the protein. Typically, a peptide linker is between about 1 and 30 amino acids in length. Examples of peptide linkers include, but are not limited to, --Gly-Gly--, GGGGS (SEQ ID NO:10), (GGGGS)n (SEQ ID NO:11), GKSSGSGSESKS (SEQ ID NO:12), GSTSGSGKSSEGKG (SEQ ID NO:13), GSTSGSGKSSEGSGSTKG (SEQ ID NO:14), GSTSGSGKSSEGKG (SEQ ID NO:15), GST-SGSGKPGSGEGSTKG (SEQ ID NO:16), EGKSSGSGS-ESKEF (SEQ ID NO:17) and GGGGSGGGGSGGGGS (SEQ ID NO:18). Linking moieties are described, for example, in Huston, J. S., et al., Proc. Natl. Acad. Sci. 85: 5879-83 (1988), Whitlow, M., et al., Protein Engineering 6: 989-95 (1993), Newton, D. L., et al., Biochemistry 35: 545-53 (1996), and U.S. Pat. Nos. 4,751,180 and 4,935,233. The relevant portions of these references, that is, the portions describing linkers, are incorporated herein by reference.

Alternatively, described herein are BTNL3 variant proteins that can antagonize the inhibition by a BTNL3 protein comprising the amino acid sequence of SEQ ID NO:7 of proliferation of a T cell stimulated by an immobilized anti-CD3 antibody. Such BTNL3 variants can comprise an amino acid sequence at least about 90%, 95%, or 98% identical to amino acids 18-236 of SEQ ID NO:2 or 18-166 of SEQ ID NO:9 and/or can comprise an amino acid sequence containing not more than 20, 15, 10, 8 or 5 insertions, deletions, or substitutions of a single amino acid relative to amino acids 18-236 of SEQ ID NO:2 or amino acids 18-166 of SEQ ID NO:9. Such variants do not contain an amino acid sequence identical to amino acids 18-236 of SEQ ID NO:2 or amino acid 18-166 of SEQ ID NO:9.

A recombinant BTNL3 fusion protein can comprise a BTNL3 protein that lacks its normal signal sequence and has, instead, a different signal sequence replacing it. The choice of a signal sequence depends on the type of host cells in which the recombinant protein is to be produced, and a different signal sequence can replace the native signal sequence. Examples of signal sequences that are functional in mammalian host cells include the following: the signal sequence for interleukin-7 (IL-7) described in U.S. Pat. No. 4,965,195; the signal sequence of human IgK (which is METDTLLLWVLLLWVPGSTG; SEQ ID NO:3); the signal sequence for human growth hormone (that is, MATGSRTSLLLAFGLLCLPWLQEGSA; SEQ ID NO:4); the signal sequence for interleukin-2 receptor described in Cosman et al. ((1984), Nature 312: 768); the interleukin-4 receptor signal peptide described in EP Patent 0 367 566; the type I interleukin-1 receptor signal peptide described in U.S. Pat. No. 4,968,607; and the type II interleukin-1 receptor signal peptide described in EP Patent 0 460 846. The portions of these references describing these signal sequences are incorporated herein by reference.

BTNL3 Nucleic Acids

The invention encompasses isolated nucleic acids, including, for example, DNAs and RNAs that encode the BTNL3 proteins described herein, which include proteins comprising the amino acid sequence of SEQ ID NO:2 or SEQ ID NO:9 and fragments and/or variants thereof. Such nucleic acids include DNAs that do not include exon sequences. These nucleic acids are useful for, inter alia, producing recombinant proteins and detecting the presence of BTNL3 nucleic acids in tissue samples, e.g., for diagnostic uses. Such nucleic acids can be genomic DNA or cDNA. As is known in the art, a cDNA sequence does not include exon sequence that can be present in genomic DNA. The nucleic acids can comprise an uninterrupted open reading frame encoding a BTNL3 protein. Nucleic acid molecules of the invention include DNA and RNA in both single-stranded and double-stranded form, as well as the corresponding complementary sequences. An "isolated nucleic acid" is a nucleic acid that has been separated from adjacent genetic sequences present in the genome of the organism from which the nucleic acid was isolated, in the case of nucleic acids isolated from naturally-occurring sources. In the case of nucleic acids synthesized chemically, such as oligonucleotides, or enzymatically from a template, such as polymerase chain reaction (PCR) products or cDNAs, it is understood that the nucleic acids resulting from such processes are isolated nucleic acids. An isolated nucleic acid molecule refers to a nucleic acid molecule in the form of a separate fragment or as a component of a larger nucleic acid construct such as a vector.

Further, the invention encompasses fragments of a nucleic acid encoding a BTNL3 protein that can serve (1) as probes for detecting BTNL3 nucleic acids by a number of methods well known in the art, e.g., Southern and northern blotting, dot blotting, colony hybridizations, hybridization to an array, etc., (2) as polymerase chain reaction (PCR) primers to amplify BTNL3 nucleic acids, or (3) as a means to regulate expression of BTNL3 nucleic acids, e.g., through inhibition of expression with antisense nucleic acids (including peptide nucleic acids), ribozymes, triple helix-forming molecules, or interfering RNAs. DNAs that encode any of these RNAs are also BTNL3 nucleic acids as meant herein. PCR primers can comprise, in addition to BTNL3 nucleic acid sequences, other sequences such as restriction enzyme cleavage sites that facilitate the use of the amplified nucleic acid. PCR is described, for example, in the following references: Saiki et al. (1988), Science 239: 487-91; PCR Technology, Erlich, ed., Stockton Press, (1989). As explained below, PCR can be useful to detect over- or under-expression of BTNL3 mRNAs, and PCR primers can be taken from various parts of the BNTL3 gene and can also be selected to distinguish between different splice variants. Antisense RNAs (and DNAs encoding them), DNAs, or synthetic nucleotides and their use to regulate expression are well known in the art and are described in, e.g. Izant and Weintraub (1984), Cell 36(4): 1007-15; Izant and Weintraub (1985), Science 229(4711): 345-52; Harel-Bellan et al. (1988), J. Exp. Med. 168(6): 2309-18; Sarin et al. (1988), Proc. Natl. Acad. Sci. USA 85(20): 7448-51; Zon (1988), Pharm. Res. 5(9): 539-49; Harel-Bellan et al. (1988), J. Immunol. 140(7): 2431-35; Marcus-Sekura et al. (1987), Nucleic Acids Res. 15(14): 5749-63; Gambari (2001), Curr. Pharm. Des. 7(17): 1839-62; and Lemaitre et al. (1987), Proc. Natl. Acad. Sci. USA 84(3): 648-52. The portions of these references describing techniques of modulating gene expression using nucleic acids are incorporated by reference herein. Similarly, interfering RNAs (and DNAs encoding them) and their use to inhibit expression of selected genes are well known in the art and described in, e.g., Fjose et al. (2001), Biotechnol. Ann. Rev. 7: 31-57; Bosher and Labouesse (2000), Nature Cell Biol. 2: E31-E36. The relevant portions of these references are incorporated herein by reference. Further, ribozymes or DNAzymes can be targeted to cleave specific RNAs and thus used to inhibit gene expression as described in, e.g., Lewin and Hauswirth (2001), Trends Mol. Med. 7(5): 221-28; Menke and Hobom (1997), Mol. Biotechnol. 8(1): 17-33; Norris et al. (2000), Adv. Exp. Med. Biol. 465: 293-301; Sioud (2001), Curr. Mol. Med. 1(5): 575-88; and Santiago and Khachigian (2001), J. Mol. Med. 79(12): 695-706. The portions of these references describing these methods of modulating gene expression are incorporated by reference herein. Such nucleic acids that can regulate BTNL3 expression can find use in in vivo or in vitro studies of BTNL3 function or as therapeutics, optionally, as gene therapy agents.

The present invention also includes nucleic acids, for example, DNAs, comprising the sequence of SEQ ID NO:1 or SEQ ID NO:8 or a fragment thereof or nucleic acids that hybridize under moderately stringent conditions, and optionally highly stringent conditions, to nucleic acids comprising the nucleotide sequence of SEQ ID NO:1 or SEQ ID NO:8, which are BTNL3 cDNAs, wherein the nucleic acid encodes a protein that can inhibit the proliferation of T cells activated with an immobilized anti-CD3 antibody. Hybridization techniques are well known in the art and are described by Sambrook, J., E. F. Fritsch, and T. Maniatis (*Molecular Cloning: A Laboratory Manual*, Cold Spring Harbor Laboratory Press, Cold Spring Harbor, N.Y., chapters 9 and 11, (1989)) and *Current Protocols in Molecular Biology* (F. M. Ausubel et al., eds., John Wiley & Sons, Inc., sections 2.10 and 6.3-6.4 (1995)), the relevant portions of which are incorporated by reference herein. Generally, moderately stringent conditions for filter hybridizations include hybridization in about 50% formamide, 6×SSC at a temperature from about 42° C. to 55° C. and washing at about 60° C. in 0.5×SSC, 0.1% SDS. Generally, highly stringent conditions are defined as hybridization conditions as above, but with washing at approximately 68° C. in 0.2×SSC, 0.1% SDS. SSPE (1×SSPE is 0.15 M NaCl, 10 mM $NaH_2PO_4$, and 1.26 mM EDTA, pH 7.4) can be substituted for SSC (1×SSC is 0.15 M NaCl and 15 mM sodium citrate) in the hybridization and wash buffers; washes, optionally at least two washes, are performed for 15 minutes after hybridization is complete.

It should be understood that the wash temperature and wash salt concentration can be adjusted as necessary to achieve a desired degree of stringency by applying the basic principles that govern hybridization reactions and duplex stability, as known to those skilled in the art and described further below (see e.g., Sambrook et al., supra). When nucleic acids of known sequence are hybridized, the hybrid length can be determined by aligning the sequences of the nucleic acids (for example, using GAP) and identifying the region or regions of optimal sequence complementarity. Somewhat different conditions than those described above can apply for hybrids of relatively short lengths. The hybridization temperature for hybrids anticipated to be less than 50 base pairs in length should be 5 to 10° C. less than the melting temperature (Tm) of the hybrid, where Tm is determined according to the following equations. For hybrids less than 18 base pairs in length, Tm (degrees C.)=2(# of A+T bases)+4(# of G+C bases). For hybrids above 18 base pairs in length, Tm (degrees C.)=81.5+16.6 ($\log_{10}$ [$Na^+$])+0.41(% G +C)−(600/N), where N is the number of bases in the hybrid, and [$Na^+$] is the concentration of sodium ions in the hybridization buffer. Each such hybridizing nucleic acid can have a length that is at least 15 nucleotides, or at least 18 nucleotides, or at least 20 nucleotides, or at least 25 nucleotides, or at least 30 nucleotides, or at least 40 nucleotides, or at least 50 nucleotides, or at least 100 nucleotides. Sambrook et al., supra.

BTNL3 nucleic acids, such as cDNAs, include nucleic acids comprising the following polynucleotides: (1) all or a fragment of SEQ ID NO:1 or SEQ ID NO:8, wherein the fragment encodes a BTNL3 protein that can inhibit proliferation of T cells; (2) a polynucleotide including nucleotide sequences at least 80%, 85%, 90%, 95%, 97%, 98%, 99%, 99.5%, or 99.7% identical to SEQ ID NO:1 or SEQ ID NO:8, wherein the alignment window is at least 100, 125, 150, 175, 200, 225, 250, 300, 400, 500, 600, 800, 1000. or 1200 nucleotides long and wherein the sequence encodes a BTNL3 protein that can inhibit the proliferation of T cells activated with an immobilized anti-CD3 antibody or can antagonize such inhibition; (3) fragments of SEQ ID NO:1 or SEQ ID NO:8 or substantially similar sequences that are useful for detecting or amplifying nucleic acids encoding the BTNL3 proteins of the invention or for regulating the expression of BTNL3 mRNAs and/or proteins; (4) a polynucleotide that comprises not more than 1, 2, 3, 4, 6, 8, 10, 15, 20, 25, or 30 alteration(s) of a single nucleotide relative to SEQ ID NO:1 or SEQ ID NO:8, wherein an alteration can be an insertion, deletion or substitution of a single nucleotide, and wherein the polynucleotide encodes a BTNL3 protein can inhibit the proliferation of T cells activated with an immobilized anti-CD3 antibody or can serve as an antagonist of such inhibition; and (5) a polynucleotide that encodes a BTNL3 protein as described herein, which includes fragments, derivatives and variants of a human BTNL3 protein.

Methods of Making BTNL3 Proteins and Anti-BTNL3 Antibodies

BTNL3 proteins, including multimeric BTNL3 proteins or variant BTNL3 proteins, or anti-BTNL3 antibodies (or anti-idiotypic antibodies) can be made as follows. A nucleic acid, for example a DNA, that encodes a BTNL3 protein or an anti-BTNL3 antibody, as described herein, can be introduced into a vector, which can be introduced into a host cell, for example a non-human host cell, which can be a mammalian cell. Vectors and host cells comprising nucleic acids, such as DNAs, encoding a BTNL3 protein or an anti-BTNL3 antibody are encompassed by the invention. The host cell containing the nucleic acids encoding a BTNL3 protein or an anti-BTNL3 antibody can be cultured under conditions such that the BTNL3 protein or the anti-BTNL3 antibody can be expressed. The expressed BTNL3 protein or anti-BTNL3 antibody can then be obtained from the medium in which the cells are cultured or from the cells and purified by any of the many appropriate means known in the art. In addition, genetic engineering methods for the production of BTNL3 proteins include the expression of the polynucleotide molecules in cell free expression systems, in cellular hosts, in tissues, and in animal models, according to known methods.

The vector can include a selectable marker and an origin of replication, for propagation in a host. The vector can further include suitable transcriptional or translational regulatory sequences, such as those derived from mammalian, microbial, viral, or insect genes, operably linked to the nucleic acid encoding the BTNL3 protein or the anti-BTNL3 antibody. Examples of such regulatory sequences include transcriptional promoters, operators, or enhancers, mRNA ribosomal binding sites, and appropriate sequences that control transcription and translation. Nucleotide sequences are operably linked when the regulatory sequence functionally relates to the DNA encoding the target protein. Thus, a promoter nucleotide sequence is operably linked to a nucleic sequence if the promoter nucleotide sequence directs the transcription of the anti-BTNL3 antibody-encoding or BTNL3 protein-encoding sequence. If the BTNL3 protein is a fusion protein, a nucleic acid sequence encoding a portion of the fusion protein, for example, a signal sequence, can be part of a vector, and a nucleic acid encoding an anti-BTNL3 antibody or a BTNL3 protein can be inserted into the vector such that a protein comprising the added signal sequence plus the anti-BTNL3 antibody or BTNL3 protein is encoded by the vector.

Suitable host cells for expression of BTNL3 proteins or anti-BTNL3 antibodies include human and non-human cells including prokaryotic cells such as bacteria, yeast cells, plant cells, insect cells, and higher eukaryotic cells, including mammalian cells. The regulatory sequences in the vector will be chosen such that they are operable in the host cell. Suitable prokaryotic host cells include bacteria of the genera *Escherichia, Bacillus*, and *Salmonella*, as well as members of the genera *Pseudomonas, Streptomyces*, and *Staphylococcus*. For expression in prokaryotic cells, for example, in *E. coli*, the polynucleotide molecule encoding a BTNL3 protein or anti-BTNL3 antibody preferably includes an N-terminal methionine residue to facilitate expression of the recombinant polypeptide. The N-terminal methionine may optionally be cleaved from the expressed polypeptide. Suitable yeast host cells include cells from genera including *Saccharomyces, Pichia*, and *Kluveromyces*, including species such as *S. cerevisiae* and *P. pastoris*. A suitable system for expression in an insect host cell is described, for example, in the review by Luckow and Summers ((1988), BioTechnology 6: 47), the relevant portions of which are incorporated herein by reference. Suitable mammalian host cells include the COS-7 line of monkey kidney cells (Gluzman et al. (1981), Cell 23: 175-182), baby hamster kidney (BHK) cells, Chinese hamster ovary (CHO) cells (Puck et al. (1958), PNAS USA 60: 1275-1281), CV-1 (Fischer et al. (1970), Int. J. Cancer 5: 21-27), 293 cells from human kidney (American Type Culture Collection (ATCC®) catalog no. CRL-10852™), and human cervical carcinoma cells (HELA) (ATCC® CCL 2). The relevant portions of the references referred to in this paragraph are incorporated herein by reference.

Expression vectors for use in cellular hosts generally comprise one or more phenotypic selectable marker genes. Such genes encode, for example, a protein that confers antibiotic resistance or that supplies an auxotrophic requirement. A wide variety of such vectors are readily available from commercial sources. Examples include pGEM® vectors (Promega), pSPORT™ vectors, and pPROEX™ vectors (InVitrogen, Life Technologies, Carlsbad, Calif.), Bluescript vectors (Stratagene), and pQE vectors (Qiagen). Yeast vectors will often contain an origin of replication sequence from a 2 µyeast plasmid, an autonomously replicating sequence (ARS), a promoter region, sequences for polyadenylation, sequences for transcription termination, and a selectable marker gene. Vectors replicable in both yeast and *E. coli* (termed shuttle vectors) may also be used. In addition to the above-mentioned features of yeast vectors, a shuttle vector will also include sequences for replication and selection in *E. coli*. Direct secretion of the target polypeptides expressed in yeast hosts may be accomplished by the inclusion of nucleotide sequence encoding the yeast α-factor leader sequence at the 5' end of the BTNL3- or antibody-encoding nucleotide sequence. Brake (1989), Biotechnology 13: 269-280.

Examples of suitable expression vectors for use in mammalian host cells include pcDNA3.1/Hy gro+ (Invitrogen), pDC409 (McMahan et al. (1991), EMBO J. 10: 2821-2832), and pSV$_L$ (Pharmacia Biotech). Expression vectors for use in mammalian host cells can include transcriptional and translational control sequences derived from viral genomes. Commonly used promoter sequences and enhancer sequences that can be used to express BTNL3 RNA include, but are not limited to, those derived from human cytomegalovirus (CMV), Adenovirus 2, Polyoma virus, and Simian virus 40 (SV40). Methods for the construction of mammalian expression vectors are disclosed, for example, in Okayama and Berg ((1982) Mol. Cell. Biol. 2:161-170), Cosman et al. ((1986) Mol. Immunol. 23:935-941), Cosman et al. ((1984) Nature 312: 768-771), EP-A-0367566, and WO 91/18982. The relevant portions of these references are incorporated herein by reference.

Anti-BTNL3 Antibodies

Antibodies that bind specifically to the BTNL3 proteins described herein, anti-idiotypic antibodies that bind to anti-BTNL3 antibodies and uses of these antibodies are described herein. An anti-BTNL3 antibody can bind to a polypeptide, wherein the amino acid sequence of the polypeptide consists of the amino acids 18 to 236 of SEQ ID NO:2 or amino acids 18 to 166 of SEQ ID NO:9. As used herein, specific binding of an epitope on a BTNL3 protein by a first antibody means that the first antibody can be displaced from the BTNL3 protein by another antibody that competes with the first antibody, but not by other anti-BTNL3 antibodies that do not compete with the first antibody for binding. Numerous competitive binding assays are known in the art.

Typically competition of antibodies for binding can be evaluated by a fluorescence activated cell sorting (FACS) assay. The antibody of interest can be biotinylated. The biotinylated antibodies are combined with cells known to express the antigen to which the antibodies bind. If the biotinylated antibodies bind to the cells as expected, a shift in fluorescence intensity should be observed using a secondary consisting of strepavidin conjugated to a fluorochrome. Pre-incubation of the cells with an unlabeled version of the same antibody should completely eliminate the observed shift in fluorescence. Pre-incubation with a different unlabeled antibody may completely or partially eliminate the fluorescence shift or have no effect. In the later case, one would conclude that the unlabeled antibody does not compete with the labeled antibody. In the former case, the antibodies do compete for binding, and, as meant herein, one would conclude that the epitopes are either fully or partially overlapping. Alternatively, the unlabeled antibody may compete by altering the conformation of the epitope bound by the labeled antibody. Among the antibodies contemplated are those that compete, either fully or partially, with any specifically provided anti-BTNL3 antibody.

In some embodiments, an anti-BNTL3 antibody can bind to a human BTNL3 protein with an equilibrium dissociation constant ($K_D$) of no more than $10^{-8}$, $10^{-9}$, $10^{40}$, or $10^{-11}$ M. A $K_D$ is commonly determined by use of a specialized instrument that can detect interactions between proteins in real time using surface plasmon resonance, such as those sold by Biacore Life Sciences, Piscataway, N.J. In some embodiments, an anti-BTNL3 antibody can bind to a BTNL3 protein comprising an amino acid sequence at least 90%, 95%, 97%, 98%, or 100% identical to SEQ ID NO:2 and/or SEQ ID NO:9, wherein the alignment window with SEQ ID NO:2 and/or 9 is at least 50, 60, 70, 80, or 100 amino acids long and, optionally, wherein the BTNL3 protein can inhibit the proliferation of a T cell stimulated by an immobilized anti-CD3 antibody or can antagonize such inhibition by a BTNL3 protein comprising the amino acid sequence of SEQ ID NO:7. In some embodiments, an anti-BTNL3 antibody can bind to a protein comprising a fragment of the amino acid sequence of SEQ ID NO:2 and/or 9.

In addition, the impact of an anti-BTNL3 antibody on activation of anti-CD3-activated T cells in the presence or absence of a BTNL3 protein may provide additional useful information about the functional properties of an antibody. Particularly, antibodies that prevent or inhibit BTNL3 from exerting its usual role of inhibiting the proliferation of anti-CD3-activated T cells are contemplated. Alternatively, antibodies that agonize or enhance the inhibition of proliferation of anti-CD3-activated T cells by BTNL3 are contemplated. Thus, the antibodies can be either antagonists or agonists of BTNL3. Since BTNL3 contains an intracellular B30.2 domain, it may transduce a signal into the cell on which it is expressed when its extracellular domain is engaged by an agonist, such as a naturally occurring ligand or an agonistic antibody. This kind of agonistic antibody can be distinct from antibodies that enhance the inhibition of proliferation of T cells. The invention includes monoclonal antibodies, each of which binds to a particular epitope of BTNL3, and monoclonal antibodies that compete with these for binding. The antibodies can be human, humanized, or chimeric antibodies and can be in various formats.

Epitopes on BTNL3 protein may comprise contiguous amino acids and also may comprise non-contiguous amino acids. Epitopes can be identified by methods known in the art, including the use of protein fragment or peptide libraries, alanine scanning, epitope extraction, epitope excision, or X-ray crystallography. See e.g. Leinonen et al. (2002), Clin. Chem. 48(12): 2208-16; Kroger et al. (2002), Biosens. Bioelectron. 17(11-12): 937-44; Zhu et al. (2001), Biochem. Biophys. Res. Commun. 282(4): 921-27; Obungu et at. (2009), Biochemistry 48: 7251-60. The relevant portions of these references, i.e., the portions describing methods of epitope mapping, are incorporated herein by reference. In addition, especially in view of the fact that BTNL3 includes some domains of well known tertiary structure, such as an IgV-like domain, tertiary structures of BTNL3 generated by analogy to known tertiary structures can be used as an aid to determining epitopes.

Antibodies can be polyclonal or monoclonal antibodies and can be produced by methods well known in the art. See, for example, *Monoclonal Antibodies, Hybridomas: A New Dimension in Biological Analyses*, Kennet et al. (eds.), Plenum Press, New York (1980); and *Antibodies: A Laboratory Manual*, Harlow and Land (eds.), Cold Spring Harbor Laboratory Press, Cold Spring Harbor, N.Y., (1988); Kohler and Milstein (1980) Proc. Natl. Acad. Sci., USA, 77: 2197; Kozbor et al. (1984), J. Immunol. 133: 3001-3005 (describing the human B-cell hybridoma technique); Cole et al., *Monoclonal Antibodies And Cancer Therapy*, Alan R. Liss, Inc., pp. 77-96 (1985)(which describes EBV-hybridoma technique);. Kuby, *Immunology*, Second Edition, p. 162-64, W. H. Freeman and Co., New York (1994); the relevant portions of these references are incorporated herein by reference. Hybridoma cell lines that produce monoclonal antibodies specific for the BTNL3 proteins as described herein are also contemplated herein. Such hybridoma lines can be produced and identified by conventional techniques. The hybridoma producing an anti-BTNL3 antibody can be cultivated in vitro or in vivo. Further, anti-BTNL3 antibodies can be produced in other cultured cells, including, for example, Chinese hamster ovary (CHO), HeLa, VERO, BHK, Cos, MDCK, 293, 3T3, myeloma (e.g. NSO, NSI), or WI38 cells, yeast cells, insect cells, and bacterial cells, including, for example, *Escherichia coli*. Such antibodies can be produced by introducing nucleic acids, such as DNAs, encoding the antibodies plus nucleic acids to enable expression of these nucleic acids into desired host cells. The antibodies can then be produced by culturing the cells into which these nucleic acids have been introduced. Monoclonal antibodies can be of any immunoglobulin class including IgG, IgM, IgE, IgA, IgD and any subclass thereof, such as, for example, IgG1, IgG2, IgG3, or IgG4.

Anti-BTNL3 antibodies can be full-length tetrameric antibodies comprising two heavy chains and two light chains, like those found in most mammalian species. Such a full length antibody can be of the IgA, IgD, IgG, IgM, or IgE isotype. If it is an IgG antibody, it can be an IgG1, IgG2, IgG3, or IgG4 antibody. Alternatively, anti-BTNL3 antibodies can be single chain antibodies comprising a heavy and a light chain variable region and, optionally, also one or more constant region-like domain (U.S. Pat. No. 4,946,778; Bird et al. (1988), Science 242: 423-26; Huston et al. (1988), Proc. Natl. Acad. Sci. USA 85: 5879-83), dimeric or multivalent antibodies (see e.g. Lantto et al. (2002), J. Gen. Virol. 83: 2001-05; Hudson and Souriau (2001), Expert Opin. Biol. Ther. 1(5): 845-55), tetrameric antibodies (see e.g. Janeway et al., Immunobiology: The Immune System in Health and Disease, Fifth Edition, Part II, Ch. 3, Garland Publishing (2001)), chimeric antibodies (Hudson and Souriau, supra; Boulianne et al. (1984), Nature 312:643-46; Morrison et al (1984), Proc. Natl. Acad. Sci. USA 81: 6851-55; Takeda et al. (1985), Nature 314: 452-54; Neuberger et al. (1985), Nature 314: 268-70), fully human antibodies produced in a non-human transgenic mammal (described in e.g., U.S. Pat. No. 6,150,584) or by in vitro selection (US Patent Application 2002/0058033) or humanized antibodies (Morrison et al., supra; Takeda et al., supra; Boulianne et al., supra). Further, antibodies can be "matured" by in vitro selection schemes to yield an antibody with altered properties such as, for example, a higher affinity for the epitope to which it binds. See e.g. Jackson et al. (1995), J. Immunol. 154(7): 3310-19; Pini and Bracci (2000), Curr. Protein Pept. Sci. 1(2): 155-69; Ellmark et al. (2002), Mol. Immunol. 39(5-6): 349; O'Connell et al. (2002), J. Mol. Biol. 321(1): 49-56; Huls et al. (2001), Cancer Immunol. Immunother. 50: 163-71; Hudson and Souriau, supra; Adams and Schier (1999), J. Immunol. Methods 231(1-2): 249-60; Schmitz et al. (2000), Placenta 21 Suppl. A: S106-12. Alternatively, fragments of antibodies such as, for example, Fab fragments, F(ab')z fragments, or single chain Fv fragments (scFv's) that can bind specifically to a BTNL3 protein of the invention are also encompassed by what is meant herein as an anti-BTNL3 antibody. See Kuby, supra, pp. 109-112 and Janeway et al., supra, for discussion of Fab and Fv fragments. The invention also encompasses anti-idiotypic antibodies that bind specifically to antibodies that bind specifically to BTNL3 proteins and that mimic the effects of BTNL3 proteins. Such anti-idiotypic antibodies find the same uses as BTNL3 proteins. Methods for generating anti-idiotypic antibodies are well known in the art. See e.g. Kuby et al., supra, at 371-72. Various kinds of recombinant and non-recombinant bispecific antibodies that can bind specifically to a BTNL3 protein of the invention and another protein are also contemplated. Various kinds of bispecific antibodies and methods for making them are described in e.g. U.S. Pat. Nos. 4,474,893, 6,060,285, and 6,106,833.

The anti-BTNL3 antibodies can be multimeric antibodies, including full-length, tetrameric, bispecific antibodies containing two complete heavy chains and two complete light chains or multimeric monovalent antibodies containing, for example, a heavy chain plus a light chain plus an Fc region. Such multimeric antibodies can contain certain mutations in their Fc region that facilitate the formation of heterodimers.

Such antibodies and mutations are described in International Patent Publication No. International Application WO 2009/089004 and US Application 2007/0105199, the portions of which describe such antibodies and mutations are incorporated by reference herein. The Fc regions in such antibodies can have native human sequences or sequences native to other species. Alternatively or in addition, the Fc regions of such antibodies can contain mutations in their Fc regions that either increase or decrease effector function by increasing or decreasing the affinity of various Fc receptors for the Fc region. Some such Fc alterations are discussed in U.S. Pat. No. 5,457,035 and International Patent Application Publication No. WO 93/10151, the relevant portions of which are incorporated herein by reference.

Anti-BTNL3 antibodies can also be conjugated to moieties can be used to locate, to inhibit proliferation of, or to kill cells that antibody can bind to. Among such cytotoxic, cytostatic, luminescent, and/or radioactive moieties are, for example, maytansine derivatives (such as DM1), enterotoxins (such as a Staphlyococcal enterotoxin), iodine isotopes (such as iodine-125), technetium isotopes (such as Tc-99m), cyanine fluorochromes (such as Cy5.5.18), ribosome-inactivating proteins (such as bouganin, gelonin, or saporin-S6), and calicheamicin, a cytotoxic substance that is part of a product marketed under the trademark MYLOTARG™ (Wyeth-Ayerst).

An antibody may contain only a single heavy or light chain variable region, optionally fused to another portion of an antibody as described in US Patent Application 2004/058820, the portions of which describe these single domain antibodies are incorporated herein by reference.

Some naturally-occurring antibodies, which have been found in camels and llamas, are dimers consisting of two heavy chains and include no light chains. Muldermans et al., 2001, *J. Biotechnol.* 74:277-302; Desmyter et al., 2001, *J. Biol. Chem.* 276:26285-90, the portions of which describe the structures of these antibodies are incorporated herein by reference. Anti-BTNL3 antibodies having this structure are among the anti-BTNL3 antibodies of the invention.

Anti-BTNL3 antibodies can have a variety of activities and uses. Anti-BTNL3 antibodies may be antagonistic antibodies that block or inhibit the biological function of BTNL3, for example by blocking or antagonizing BTNL3-dependent inhibition of T cell proliferation, which can be assayed by the methods described in the Examples herein. The antibodies can also be agonistic antibodies. In some embodiments, agonistic antibodies can bind to the BTNL3 counterstructure and mimic BTNL3 binding to inhibit T cell activation or proliferation. Agonistic antibodies may also be anti-idiotypic antibodies that bind to anti-BTNL3 antibodies and/or also bind to the BTNL3 counterstructure and mimic the activity of BTNL3, that is, they inhibit the proliferation of T cells as described herein. Such agonistic anti-BTNL3 antibodies can be used for the same uses as a BTNL3 protein. Anti-BTNL3 antibodies can be agonistic or antagonistic by, for example, stabilizing or disrupting the BTNL3 protein, possibly in combination with other proteins, on the cell surface. For example, an agonistic antibody may enhance the activity of BTNL3 by stabilizing the transmembrane form of BTNL3, or by stabilizing the interaction of a BTNL3 protein with other BTNL3 proteins or different proteins on the surface of a cell or the clustering of BTNL3 protein on the surface of cells. Further, an antagonistic antibody may inhibit BTNL3 activity by destabilizing the transmembrane form of BTNL3, or by destabilizing interactions among multiple molecules of BTNL3 or interactions of BTNL3 with other proteins, on the cell surface of cells.

Agonistic anti-BNTL3 antibodies can also bind transmembrane forms of BTNL3, causing it to transduce a biological signal into the cell on which it is expressed. Such a signal, may, for example, decrease or increase the immune function of an immune cell, e.g., a neutrophil, expressing BTNL3. In some embodiments, an agonistic anti-BTNL3 antibody may cause a decrease in proliferation or cell death of cells expressing BTNL3, such as cancer cells or neutrophils. An antagonistic anti-BTNL3 antibody can be used to enhance an immune response. Hence, antagonistic anti-BNTL3 antibodies can find use, for example, in the treatment of cancer or in a vaccine, for example in a vaccine to induce a response to a cancer-specific antigen.

Anti-BTNL3 antibodies can be conjugated to a cytotoxic, cytostatic, luminescent, and/or radioactive moiety. Such antibodies can be used to locate, to inhibit proliferation of, or to kill cells that express BTNL3. Since some cancer cells express BTNL3, such antibody conjugates can be used to treat such cancers. Similarly, since neutrophils express BTNL3, such antibody conjugates can be used to treat conditions characterized by excessive numbers of neutrophils or excessive neutrophil activity, for example, asthma, inflammatory bowel disease including Crohn's disease and ulcerative colitis, COPD, and gout and related inflammatory crystal deposition diseases. Among such cytotoxic, cytostatic, luminescent, and/or radioactive moieties are, for example, maytansine derivatives (such as DM1), enterotoxins (such as a Staphylococcal enterotoxin), iodine isotopes (such as iodine-125), technetium isotopes (such as Tc-99m), cyanine fluorochromes (such as Cy5.5.18), ribosome-inactivating proteins (such as bouganin, gelonin, or saporin-S6), and calicheamicin, a cytotoxic substance that is part of a product marketed under the trademark MYLOTARG™ (Wyeth-Ayerst).

The antibodies of the invention can also be used in assays to detect the presence of the BTNL3 proteins of the invention, either in vitro or in vivo. The antibodies also can be employed in purifying BTNL3 proteins of the invention by immunoaffinity chromatography.

Agonists and Antagonists of BTNL3 Polypeptides

In addition to antagonistic or agonistic antibodies, other antibody-related molecules that can bind specifically BTNL3 proteins, such as affibodies (Ronnmark et al. (2002), J. Immunol. Methods 261(1-2): 199-211, the portion of which describes affibodies is incorporated by reference herein) and the biologically active peptides described in International Application WO 00/24782 (the portions of which describe these peptides are incorporated herein by reference) that can bind specifically to BTNL3 and inhibit the biological activity of BTNL3 proteins are encompassed by the invention. Further, BTNL3 antagonists include the nucleic acids described above that are useful for modulating expression of BTNL3 protein and/or mRNA, such as, for example, interfering RNAs (or DNAs that encode them) or antisense RNAs or DNAs.

Antagonists further include proteins that comprise amino acid sequences selected in vitro to bind to BTNL3 or its receptor and that can, optionally, interfere with the interaction of BTNL3 and its receptor. In some embodiments such proteins can be variant forms of BTNL3 that lack the normal activity of BTNL3 and essentially act as decoys. Alternatively, such proteins can be BTNL3 agonists that promote or mimic the biological function of BTNL3. Proteins that bind to BTNL3 or its receptor can be screened for their ability to interfere with the interaction of BTNL3 with its receptor, or, alternatively, a selection can be designed to obtain such proteins directly. Alternatively, a BTNL3 antagonist can be a variant BTNL3 protein that interferes with the biological activity of the wild type BTNL3 protein, for example, a soluble, biologically inactive BTNL3 variant that blocks the interaction of wild type BTNL3 with its receptor.

Proteins may be selected by a number of methods such as, for example, phage display or display of the surface of a bacterium. See e.g. Parmley and Smith (1989), Adv. Exp. Med. Biol. 251: 215-218; Luzzago et al. (1995), Biotechnol. Annu. Rev. 1: 149-83; Lu et al. (1995), Biotechnology (NY) 13(4): 366-372. In these methods, each member of a library of binding domains can be displayed on individual phage particles or bacterial cells, and bacteria or phage that bind to a protein of interest under chosen conditions can be selected. Nucleic acids encoding the selected binding domains can be obtained by growing the selected phage or bacteria and isolating nucleic acids from them.

Alternatively, a protein can be selected entirely in vitro. For example, each individual polypeptide in a library of potential binding domains can be attached to nucleic acids encoding it, and those that bind to the protein of interest under chosen conditions can be selected. Since the polypeptides are attached to nucleic acids encoding them, subsequent operations, such as amplifying, cloning, or sequencing nucleic acids encoding effective binding domains are facilitated. Various schemes for such selections are known in the art, including antibody-ribosome-mRNA particles, ribosome display, covalent RNA-peptide fusions, or covalent DNA-RNA-peptide fusions. He and Taussig (1997), Nucleic Acids. Res. 25(24): 5132-5134; Hanes and Pluckthun (1997), Proc. Natl. Acad. Sci. 94: 4937-4942; Roberts and Szostak (1997), Proc. Natl. Acad. Sci. 94: 12297-12302; Lohse and Wright (2001), Curr. Opin. Drug Discov. Devel. 4(2): 198-204; Kurz et al. (2000), Nucleic Acids Res. 28(18): E83; Liu et al. (2000), Methods Enzymol. 318: 268-93; Nemoto et al. (1997), FEBS Lett. 414(2): 405-08; U.S. Pat. No. 6,261,804; International Applications WO 00/32823; and WO 00/34784. The portions of these publications that describe how such selections can be done are incorporated by reference herein. Such proteins can be selected to be antagonists or agonists.

Therapeutic Uses

Figure 2:
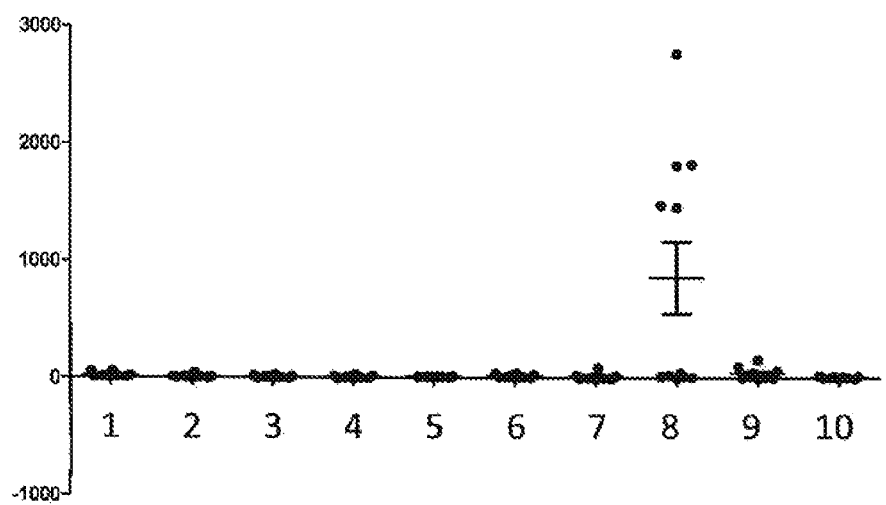
FIG. 2: This figure indicates relative amount of BTNL3 mRNA present in various primary human immune cells derived from the blood of healthy donors. The vertical axis indicates the intensity value for expression of BTNL3 mRNA generated using ROSETTA RESOLVER®. The various cell types tested are indicated along the x axis as follows: 1, peripheral blood mononuclear cells; 2, T cells; 3, CD4+ T cells; 4, CD8+ T cells; 5, B cells; 6, monocytes; 7, macrophages; 8, neutrophils; 9, eosinophils; 10, natural killer (NK) cells. The horizontal line plus error bar in lane 8 indicates the average intensity value obtained for BTNL3 expression in neutrophils plus the standard deviation. Methods are described in detail in Example 1.
Figure 4:
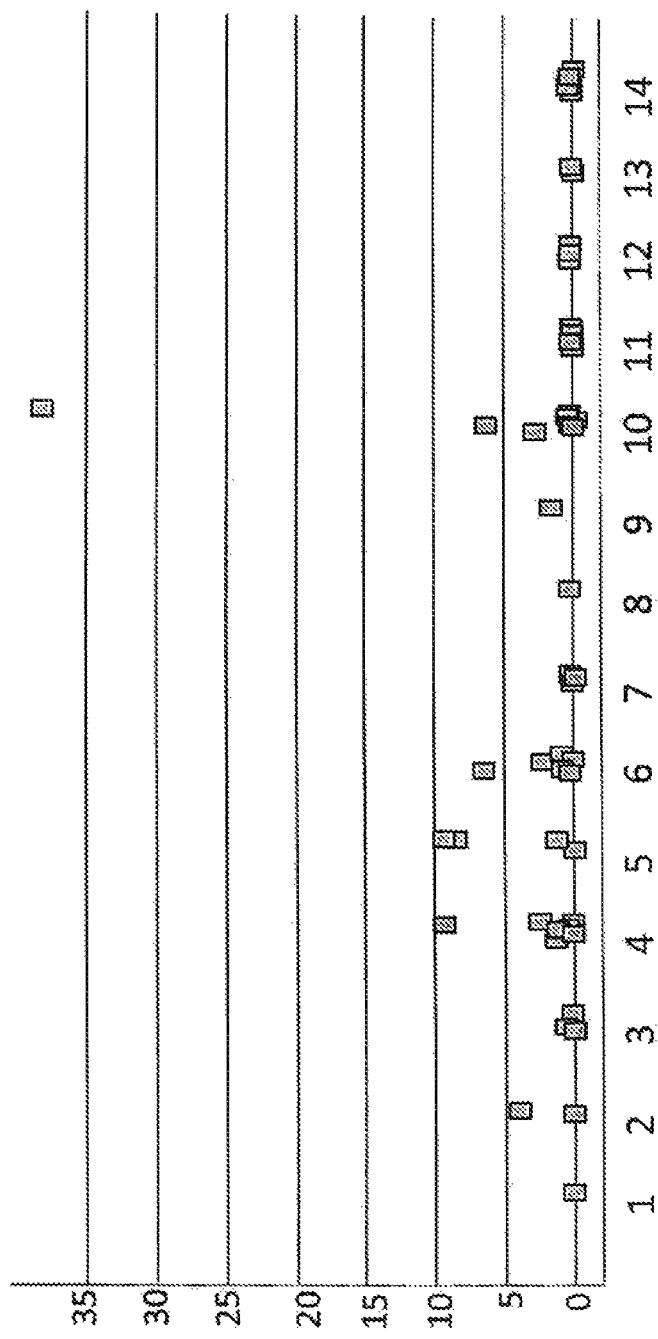
FIG. 4: This figure shows the amount of expression of BTNL3 as measured by next generation RNA sequencing analysis of samples of various human disease tissues. The x axis indicates the nature of each sample as follows: 1, metastatic adenocarcinoma; 2, adenocarcinoma, metastatic colon cancer; 3, adenocarcinoma, metastatic gastric cancer; 4, adenocarcinoma, moderately differentiated; 5, adenocarcinoma, not otherwise specified; 6, adenocarcinoma, poorly differentiated; 7, small cell carcinoma, not otherwise specified; 8, small cell carcinoma, oat cell; 9, carcinoma, undifferentiated; 10, type II diabetes sample; 11, acute myelogenous leukemia; 12, acute myeloid leukemia; 13, malignant melanoma; and 14, malignant, metastatic melanoma. The y axis indicates the amount of expression, shown as the number of BTNL3 transcript per cell.
Figure 5:
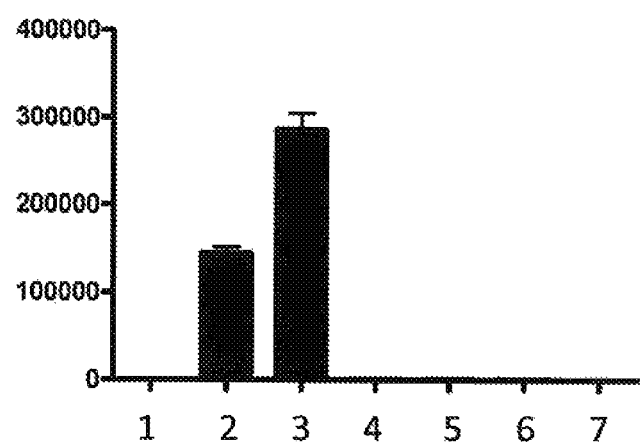
FIG. 5: The y axis indicates the levels of proliferation of mouse CD4$^+$T cells that have been activated, in some cases, with a protein immobilized on a microtiter dish, sometimes in the presence of various other proteins in solution. The lanes marked along the x axis represent samples treated as follows: lane 1, no immobilized activating protein or other protein used; lane 2, immobilized anti-CD3 antibody used to activate the cells, and human IgG included in the reaction; lane 3, immobilized anti-CD3 antibody used to activate the cells, and recombinant B7-2.Fc included in the reaction; lane 4, immobilized anti-CD3 antibody used to activate the cells, and recombinant BTNL2.Fc included in the reaction; lane 5, immobilized anti-CD3 antibody used to activate the cells, and recombinant BTNL3.Fc included in the reaction; lane 6, immobilized human IgG used to activate the cells, and recombinant BTNL2.Fc included in the reaction; and lane 7, immobilized human IgG used to activate the cells, and recombinant BTNL3.Fc included in the reaction.
Figure 6:
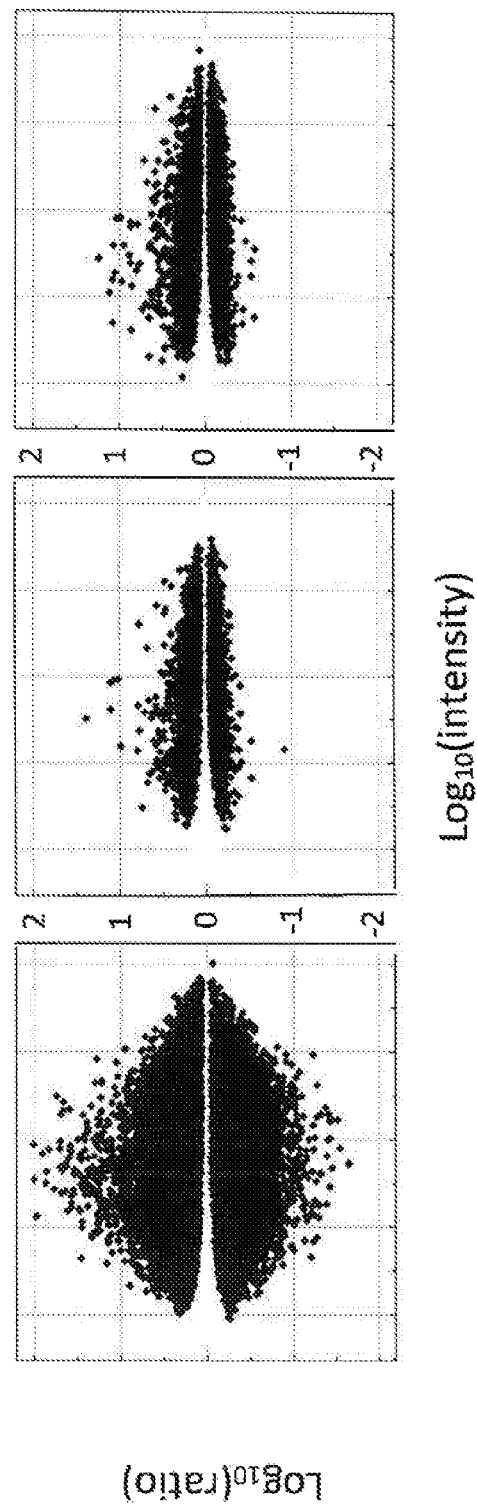
FIG. 6: In this figure, each black dot reflects data on RNA expression of a particular sequence in murine $CD4^+$T cells, where the expression of the sequence is significantly up- or down-regulated by the stimulus the cells were subjected to. Sequences whose expression was unaffected by the stimulus are not represented in the figure. The x axis indicates the $log_{10}$ of the signal intensity average of both the unstimulated and stimulated for each particular sequence detected in the array analysis. They axis indicates the $log_{10}$ of the ratio of expression after 24 hours of stimulation compared to expression of same sequence in unstimulated cells cultured for 24 hours. The stimulations used were as follows: left, stimulation with an anti-CD3 antibody alone; middle, stimulation with an anti-CD3 antibody plus a murine BTNL2.Fc fusion protein; and right, stimulation with an anti-CD3 antibody plus a human BTNL3.Fc fusion protein.

It is demonstrated herein that a BTNL3.Fc fusion protein can inhibit proliferation of activated T cells. See Example 4; FIG. 5. BTNL3 also reduces the activation state of $CD4^+$ T cells in response to an immobilized anti-CD3 antibody as reflected in a changed gene expression profile. See Example 5; FIG. 6. Also, it is shown herein that BTNL3 is relatively highly expressed on neutrophils and some kinds of cancer cells. FIGS. 2 and 4. In some situations, polymorphic forms of BTNL3 expressed on neutrophils could possibly alter immune homeostasis. Hence, BTNL3, or a molecule with the ability to agonize the BTNL3 pathway, may be useful as a therapeutic to treat autoimmune or inflammatory diseases that are mediated by T cells or neutrophils. These diseases include, for example, arthritis including rheumatoid arthritis, juvenile idiopathic arthritis, and psoriatic arthritis, Addison's disease, asthma, polyglandular endocrinopathy syndromes, systemic lupus erythematosus, chronic active hepatitis, thyroiditis, lymphocytic adenohypophysitis, premature ovarian failure, idiopathic phyoparathyroidism, pernicious anemia, glomerulonephritis, autoimmune neutropenia, Goodpasture's syndrome, myasthenia gravis, scleroderma, primary Sjogren's syndrome, polymyositis, autoimmune hemolytic anemia, an inflammatory bowel disease, such as Crohn's disease or ulcerative colitis, psoriasis, dermatitis, sarcoidosis, multiple sclerosis, chronic obstructive pulmonary disease, asthma, type 1 and type 2 diabetes, transplantation-related conditions such as graft rejection or graft versus host disease, gout and related inflammatory crystal deposition diseases, or a fibrotic disease, such as atherosclerosis, chronic obstructive pulmonary disease (COPD), cirrhosis, scleroderma, kidney transplant fibrosis, kidney allograft nephropathy, pulmonary fibrosis, including idiopathic pulmonary fibrosis, autoimmune thrombocytopenic purpura, pemphigus vulgaris, acute rheumatic fever, mixed essential cryoglobulinemia, and warm autoimmune hemolytic anemia, among many others.

BTNL3 antagonists that block or inhibit the BTNL3 pathway can find use in oncology settings. As explained above, BTNL3 antagonists can include, for example, anti-BTNL3 antibodies or variant forms of a BTNL3 protein that interfere with binding of endogenous BTNL3 proteins expressed on a cell membrane and their receptors. As shown below, BTNL3 is relatively highly expressed in certain cancer cells. Example 3; FIG. 4. This suggests that the ability of BTNL3 to inhibit activation of T cells might play a role in the ability of cancer cells to evade elimination by the immune system.

An antibody that binds to either BTNL3 or its receptor and can block or inhibit the interaction between these molecules can be used as a therapeutic to treat cancer. Other antagonists of BTNL3 described above could also be used. Some of the various cancers that might be treated with a BTNL3 pathway blocker include acute or chronic leukemias, lymphoma, non-Hodgkin's lymphoma, Hodgkin's disease, lymphocytic leukemias, lymphocytic or cutaneous lymphomas, carcinomas, adenocarcinomas, sarcomas, thymomas, neoplasms of the mediastinum, breast cancer, prostate cancer, cancers of the head and neck, lung cancer, non-small cell lung cancer, small cell lung cancer, various kinds of skin cancer, cancer of the bladder, malignant gliomas, cancers of the gastrointestinal system including cancer of the esophagus, stomach, small intestine, colon, or rectum, cancer of the pancreas, adenocarcinomas, hepatobiliary neoplasms, cancer of the kidney or ureter, testicular cancer, cancer of the urethra or penis, gynecologic tumors, ovarian cancer, sarcomas of the bone, cancers of the endocrine system, cutaneous melanoma, intraocular melanoma, neoplasms of the central nervous system, and plasma cell neoplasms, among many other cancers.

Similarly, BTNL3 antagonists, including anti-BTNL3 antibodies, can be used as a therapeutic to treat infection by a wide variety of pathogens. This may be particularly important where a pathogen can suppress T cell response. Pathogenic infections that can be treated with a BTNL3 antagonist include, without limitation, infections by viruses, bacteria, fungi, and various eukaryotic pathogens including malaria, i.e., members of the species *Plasmodium*, the species *Leishmania, nematodes*, and *helminths*, e.g., the species *Ascarus*, among many others. In some embodiments, the BTNL3 antagonist can be administered before, concurrently with, or after administration of an antigen that is all or some portion of the pathogen or is similar enough to all or some portion of the pathogen that it can elicit an immune response to the pathogen.

A BTNL3 antagonist can also find use as an agent to make a vaccine more effective. BTNL3 could be used with a vaccine to induce a response against any antigen. Among these antigens are antigens that are highly expressed on cancer cells, such as cells from the cancers mentioned above. Among these cancer antigens are the following human proteins: WT1, MUC1, LMP2, EGFRvIII, HER-2/neu, MAGE-A3, NY-ESO-1, PSMA, GM2/GD2 synthase, CEA, MLANA/MART1, gp100, survivin, prostate-specific antigen (PSA), telomerase reverse transcriptase (hTERT), sarcoma translocation breakpoints, EPHA2, prostatic acid phosphatase (PAP), melanoma inhibitor of apoptosis (ML-IAP), α-fetoprotein (AFP), epithelial cell adhesion molecule (EpCAM), ERG, NA17.A2 peptide ($V_L$ PDVFIRC), paired box 3 (PAX3), anaplastic lymphoma kinase (ALK), androgen receptor, cyclin B1, polysialic acid, rho-related GTP-binding protein RhoC, v-myc myelocytomatosis viral related oncogene (MYCN), TRP-2, GD3 ganglioside, fucosyl GM1, mesothelin, prostate stem cell antigen (PSCA), MAGE-A1, CYP1B1, PLAC1, GM3, BORIS, tetranectin (TN), ETV6-AML1 (especially peptides including the breakpoint), NY-BR-1, RGS5, SART3, STn, carbonic anhydrase IX, PAX5, proacrosin binding protein sp32 precursor (OY-TES-1), sperm protein 17 (Sp17), LCK, high molecular weight melanoma-associated antigen (HMWMAA, also known as melanoma chondroitin sulfate proteoglycan), AKAP-4, SSX2, XAGE-1, B7H3 (also known as CD276), legumain, TIE2, prostate-associated gene 4 protein (PAGE-4), vascular endothelial growth factor receptor 2 (VEGFR2), protamine 2 (also known as MAD-CT-1), glomulin (also known as FAP), PDGFR-β, SSX2, SSX5, Fos-related antigen 1, CD20, integrin αvβ3, 5T4 oncofetal antigen, CA IX, CD5, CD19, CD22 (also known as Siglec-2), CD30 (also known as TNFRSF1), CD33 (also known as Siglec-3), CD40, CD44V6, CD55, CD56 (also known as NCAM), CTLA-4 (also known as CD152), EGFR, GD2, HER2, HLA-DR10 (MHC II), IGF1R, IL-6, sialyl Lewis Y, TAG-72, TAL6, TRAILR2, VEGF, CD52 (also known as CAMPATH-1), CD4, CD73, CA125 (also known as MUC16), CD66e, CD80 (also known as B7-1), PDGFRβ, prostate specific membrane antigen (PSMA, also known as glutamate carboxypeptidase 2, among many other names). Cancer antigens also include the human herpes virus 4 protein LMP2, the human papillomavirus proteins E6 and E7, and the glycoceramide globo H (as described in Gilewski et al. (2001), Proc. Natl. Acad. Sci. 98(6): 3270-3275, the portions of which describe globo H are incorporated herein by reference), the α4 subunit of the α4β1 and α4β7 integrins, the a4I37 integrin, BAFF, APRIL, CD2, CD3, CD20, CD52, CD73, CD80, CD86, the $C_5$ complement protein, IgE, IL-1β, IL-5, IL-6R, IL-12, IL-23, and tumor necrosis factor a (TNF α).

When used to make a vaccine more effective, a BTNL3 antagonist, for example, an anti-BTNL3 antibody, can be administered before, concurrently with, or after an antigen. The antigen can be a part or all of a cancer antigen as described above. An antigen can also be part or all of a pathogen, or a molecule similar to part or all of a pathogen, part or all of a molecule that is expressed specifically on the surface of any cell that mediates a disease, a soluble antigen secreted by cells, or a molecule that can elicit a immune response to a pathogen.

A molecule that agonizes intracellular signaling through BTNL3, can serve as a treatment for a cancer where the cancer cells express BTNL3 Similarly, an inflammatory disease mediated by immune cells expressing BTNL3, for example neutrophils, can be treated with a molecule that agonizes intracellular signaling through BTNL3. Such an agonist can be an anti-BTNL3 antibody, and the intracellular signaling may be mediated through the B30.2 domain of BTNL3.

Thus, molecules that can bind to BTNL3 expressed on a neutrophil, thereby downregulating or inhibiting proliferation of the neutrophil, can be useful treatments in conditions where there is an excess of neutrophils or excessive neutrophil activity, for example, in congestive obstructive pulmonary disease (COPD), asthma, inflammatory bowel disease, including ulcerative colitis and Crohn's disease, and gout and related inflammatory crystal deposition diseases. Such molecules can include anti-BTNL3 antibodies.

On the other hand, molecules that encourage neutrophil proliferation can be useful in patients with neutropenia, who are susceptible to infection. Such patients include patients that have received chemotherapy or radiation for cancer, patients that have been exposed to toxic chemicals or drugs, or patients that have certain autoimmune diseases. Molecules that bind to BTNL3 on the surface of a neutrophil in such a way as to prevent intracellular signals of downregulation or inhibition of proliferation can be useful treatments for such patients. Such molecules can include anti-BTNL3 antibodies. Further, molecules that act as decoys, thereby preventing the interaction of BTNL3 expressed on a neutrophil with a ligand that ordinarily binds to BTNL3 thereby downregulating or inhibiting proliferation of the neutrophil on which BTNL3 is expressed, can be treatments for such conditions. Such molecules can include a BTNL3 protein or variants thereof.

In addition, an antibody conjugated to a cytotoxic, cytostatic, luminescent, and/or radioactive moiety as described above can be used to treat a cancer in which the cancer cells express BTNL3 or can be used to treat an inflammatory or autoimmune disease characterized by increased numbers of neutrophils, for example, asthma, COPD, inflammatory bowel disease, including ulcerative colitis and Crohn's disease, and gout and related inflammatory crystal deposition diseases.

"Treatment" of any disease mentioned herein encompasses an alleviation of at least one symptom of the disease, a reduction in the severity of the disease, or the delay or prevention of disease progression to more serious symptoms that may, in some cases, accompany the disease or lead to at least one other disease. Treatment need not mean that the disease is totally cured. A useful therapeutic agent needs only to reduce the severity of a disease, reduce the severity of one or more symptoms associated with the disease or its treatment, or delay the onset of more serious symptoms or a more serious disease that can occur with some frequency following the treated condition. For example, if the disease is an inflammatory bowel disease, a therapeutic agent may reduce the number of distinct sites of inflammation in the gut, the total extent of the gut affected, reduce pain and/or swelling, reduce symptoms such as diarrhea, constipation, or vomiting, and/or prevent perforation of the gut. A patient's condition can be assessed by standard techniques such as an x-ray performed following a barium enema or enteroclysis, endoscopy, colonoscopy, and/or a biopsy. Suitable procedures vary according to the patient's condition and symptoms.

A "therapeutically effective amount" of a drug used to treat a disease is an amount that can reduce the severity of a disease, reduce the severity of one or more symptoms associated with the disease or its treatment, or delay the onset of more serious symptoms or a more serious disease that can occur with some frequency following the treated condition.

The invention encompasses a method of treating inflammatory diseases such as arthritis including rheumatoid arthritis, juvenile idiopathic arthritis, and psoriatic arthritis, Addison's disease, asthma, polyglandular endocrinopathy syndromes, systemic lupus erythematosus, chronic active hepatitis, thyroiditis, lymphocytic adenohypophysitis, premature ovarian failure, idiopathic phyoparathyroidism, pernicious anemia, glomerulonephritis, autoimmune neutropenia, Goodpasture's syndrome, myasthenia gravis, scleroderma, primary Sjogren's syndrome, polymyositis, autoimmune hemolytic anemia, an inflammatory bowel disease, such as Crohn's disease or ulcerative colitis, psoriasis, dermatitis, sarcoidosis, multiple sclerosis, chronic obstructive pulmonary disease, asthma, type 1 and type 2 diabetes, transplantation-related conditions such as graft rejection or graft versus host disease, gout and related inflammatory crystal deposition diseases, or a fibrotic disease, such as atherosclerosis, chronic obstructive pulmonary disease (COPD), cirrhosis, scleroderma, kidney transplant fibrosis, kidney allograft nephropathy, pulmonary fibrosis, including idiopathic pulmonary fibrosis, autoimmune thrombocytopenic purpura, pemphigus vulgaris, acute rheumatic fever, mixed essential cryoglobulinemia, and warm autoimmune hemolytic anemia, among many others.

Such treatment involves using a therapeutically effective amount of a BTNL3 protein, or an agonistic antibody that binds to BTNL3 or its receptor, for a time sufficient to induce a sustained improvement over baseline of an indicator that reflects the severity of a particular disorder or the severity of symptoms caused by the disorder or to delay or prevent the onset of a more serious disease that follows the treated condition in some or all cases. The treatments of the invention may be used before, after, or during other treatments for the disorder in question that are commonly used, or they may be used without other treatments. For example, Crohn's disease and ulcerative colitis are commonly treated with sulfasalazine, 5-aminosalicylic acid, or corticosteroids. These treatments may be used before, during, or after treatments using a BTNL3 protein or an agonist or antagonist thereof.

Similarly, cancer is often treated with chemotherapeutic agents and such agents can be used along with the BTNL3 antagonist therapeutics, such as anti-BTNL3 antibodies, described herein. In some embodiments, the BTNL3 antagonist can be administered before, concurrently with, or after a chemotherapeutic agent. Chemotherapeutic agents include, for example, the following therapeutics: alkylating agents (e.g. busulfan, temozolomide, cyclophosphamide, lomustine (CCNU), methyllomustine, streptozotocin, cis-diamminedi-chloroplatinum, aziridinylbenzo-quinone, and thiotepa); inorganic ions (e.g. cisplatin and carboplatin); nitrogen mustards (e.g. melphalan hydrochloride, ifosfamide, chlorambucil, and mechlorethamine HCl); nitrosoureas (e.g. carmustine (BCNU)); anti-neoplastic antibiotics (e.g. adriamycin (doxorubicin), daunomycin, mitomycin C, daunorubicin, idarubicin, mithramycin, and bleomycin); plant derivatives (e.g. vincristine, vinblastine, vinorelbine, paclitaxel, docetaxel, vindesine, VP-16, and VM-26); antimetabolites (e.g. methotrexate with or without leucovorin, 5-fluorouracil with or without leucovorin, 5-fluorodeoxyuridine, 6-mercaptopurine, 6-thioguanine, cytarabine, 5-azacytidine, hydroxyurea, deoxycoformycin, gemcitabine, and fludarabine); podophyllotoxins (e.g. etoposide, irinotecan, and topotecan); as well as actinomycin D, dacarbazine (DTIC), mAMSA, procarbazine, hexamethylmelamine, pentamethylmelamine, L-asparaginase, and mitoxantrone, among many known in the art. See e.g. Cancer: Principles and Practice of Oncology, $4^{th}$ Edition, DeVita et al., eds., J. B. Lippincott Co., Philadelphia, Pa. (1993), the relevant portions of which are incorporated herein by reference.

Cancer is also commonly treated by a variety of methods with a variety of forms of radiation. It is contemplated herein that the administration of a BTNL3 antagonist to a cancer patient can occur before, concurrently with, or after radiation treatment or any other anti-neoplastic treatment.

For autoimmune or inflammatory conditions, T cells can be removed from a patient, for example, through apheresis, and stimulated ex vivo using BTNL3, optionally plus other proteins, such that the T cells attain a regulatory or inhibitory phenotype. The T cells can then be transferred back into the patient. To stimulate the T cells to attain a regulatory or inhibitory phenotype, they can be incubated in the presence of a surface, for example, with beads or in microtiter plate well, that is coated with human T cell agonistic anti-CD3 antibody, rBTNL3.Fc, and rB7-1.Fc or rB7-2.Fc in the presence of TGF-beta and IL-2. Alternatively, the surface could be coated with a combination of proteins that includes rBTNL3 or BTNL3.Fc plus an agonistic anti-CD3 antibody or a combination that includes only these proteins. In one embodiment, the agonistic anti-CD3 antibody, rBTNL3.Fc, and rB7-1.Fc or rB7-2.Fc can be, for example, at a molecular weight ratio of 2:10:2.5. The TGF-beta and IL-2 can be at appropriate concentrations, such as, for example, from about 0.05 to 5 ng/ml for TGF-beta and from about 0.5 to 10 ng/ml for IL-2. This can program the T cells to become inhibitory or regulatory, resulting in an "expansion" of regulatory T ("T reg") cells. "Expansion" of T reg cells means that the ratio of T reg cells (CD3$^+$FOXP3$^+$) to T cells as a whole (CD3$^+$FOXP3$^-$) becomes greater. This ratio can be determined by FACS analysis using antibodies to detect cell proteins, a method well known in the art. See, e.g., Swanson et al. (2013), J. Immunol. 190: 2027-2035, the relevant portions of which are incorporated herein by reference. The T cells can be incubated in such a setting for, e.g., three to seven days and then harvested and delivered back to the same patient. Optionally, the T cells can be incubated about three, four, five, six, or seven days. In some embodiments, the T cells can also be rested, i.e., cultured in the presence of, for example, IL-2, without T cell receptor or costimulatory stimulus, and then restimulated as explained above one to four more times. The autoimmune or inflammatory conditions treatable with such a regime include, for example, arthritis including rheumatoid arthritis, juvenile idiopathic arthritis, and psoriatic arthritis, Addison's disease, asthma, polyglandular endocrinopathy syndromes, systemic lupus erythematosus, chronic active hepatitis, thyroiditis, lymphocytic adenohypophysitis, premature ovarian failure, idiopathic phyoparathyroidism, pernicious anemia, glomerulonephritis, autoimmune neutropenia, Goodpasture's syndrome, myasthenia gravis, scleroderma, primary Sjogren's syndrome, polymyositis, autoimmune hemolytic anemia, an inflammatory bowel disease, such as Crohn's disease or ulcerative colitis, psoriasis, dermatitis, sarcoidosis, multiple sclerosis, chronic obstructive pulmonary disease, asthma, type 1 and type 2 diabetes, transplantation-related conditions such as graft rejection or graft versus host disease, gout and related inflammatory crystal deposition diseases, or a fibrotic disease, such as atherosclerosis, chronic obstructive pulmonary disease (COPD), cirrhosis, scleroderma, kidney transplant fibrosis, kidney allograft nephropathy, pulmonary fibrosis, including idiopathic pulmonary fibrosis, autoimmune thrombocytopenic purpura, pemphigus vulgaris, acute rheumatic fever, mixed essential cryoglobulinemia, and warm autoimmune hemolytic anemia, among many others.

Any of the above-described therapeutic agents can be administered in the form of a composition, that is, with one or more additional components such as a physiologically acceptable carrier, excipient, or diluent. For example, a composition may comprise a soluble BTNL3 protein, an anti-BTNL3 antibody, or a BTNL3 agonist or antagonist as described herein plus a buffer, an antioxidant such as ascorbic acid, a low molecular weight polypeptide (such as those having less than 10 amino acids), a protein, amino acids, carbohydrates such as glucose, sucrose, or dextrins, chelating agent such as EDTA, glutathione, and/or other stabilizers, excipients, and/or preservatives. The composition may be formulated as a liquid or a lyophilizate. Further examples of components that may be employed in pharmaceutical formulations are presented in Remington's Pharmaceutical Sciences, 16$^{th}$ Ed., Mack Publishing Company, Easton, Pa., (1980), the relevant portions of which are incorporated herein by reference.

Compositions comprising therapeutic molecules described above can be administered by any appropriate means including, but not limited to, parenteral, topical, oral, nasal, vaginal, rectal, or pulmonary (by inhalation) administration. If injected, the composition(s) can be administered intra-articularly, intravenously, intraarterially, intramuscularly, intraperitoneally, or subcutaneously by bolus injection or continuous infusion. Localized administration, that is, at the site of disease, is contemplated, as are transdermal delivery and sustained release from implants, skin patches, or suppositories. Delivery by inhalation includes, for example, nasal or oral inhalation, use of a nebulizer, inhalation in aerosol form, and the like. Administration via a suppository inserted into a body cavity can be accomplished, for example, by inserting a solid form of the composition in a chosen body cavity and allowing it to dissolve. Other alternatives include eye drops, oral preparations such as pills, lozenges, syrups, and chewing gum, and topical preparations such as lotions, gels, sprays, and ointments. In most cases, therapeutic molecules that are polypeptides can be administered topically or by injection or inhalation.

The therapeutic molecules described above can be administered at any dosage, frequency, and duration that can be effective to treat the condition being treated. The dosage depends on the molecular nature of the therapeutic molecule and the nature of the disorder being treated. Treatment may be continued as long as necessary to achieve the desired results. The periodicity of treatment may or may not be constant throughout the duration of the treatment. For example, treatment may initially occur at weekly intervals and later occur every other week. Treatments having durations of days, weeks, months, or years are encompassed by the invention. Treatment may be discontinued and then restarted. Maintenance doses may be administered after an initial treatment.

Dosage may be measured as milligrams per kilogram of body weight (mg/kg) or as milligrams per square meter of skin surface (mg/m$^2$) or as a fixed dose, irrespective of height or weight. These are standard dosage units in the art. A person's skin surface area is calculated from her height and weight using a standard formula. For example, a therapeutic BTNL3 protein or an antibody that binds to BTNL3 or its receptor can be administered at a dose of from about 0.05 mg/kg to about 10 mg/kg or from about 0.1 mg/kg to about 1.0 mg/kg. Alternatively, a dose of from about 1 mg to about 500 mg can be administered. Or a dose of about 5 mg, 10 mg, 15 mg 20 mg, 25 mg, 30 mg, 35 mg, 40, mg, 45, mg, 50 mg, 55 mg, 60 mg, 100 mg, 200 mg, or 300 mg can be administered.

The invention is described below with reference to specific examples. These examples are not meant to limit the invention in any way. It is understood for purposes of this disclosure, that various changes and modifications may be made to the invention that are well within the scope of the invention. Numerous other changes may be made which will readily suggest themselves to those skilled in the art and which are encompassed in the spirit of the invention disclosed herein and as defined in the appended claims.

EXAMPLES

Example 1

Expression of mRNA Encoding Human BTNL3 Protein in Human Immune Cells

The following experiments were done in order to gather information on expression of mRNA encoding human BTNL3 in primary human immune cells.

Primary immune cells were isolated from whole blood or leukopaks via various commercially available selection methods from Stem Cell Sciences (Palo Alto, Calif.) or Miltenyi Biotech (Germany). For example, the EASYSEP® Human T cell enrichment kit and/or the CD4$^+$T cell enrichment kit (both from Stem Cell Sciences), was used to isolate CD4$^+$T cells, while monocytes were isolated using the Miltenyi Monocyte Isolation Kit II. Such cell separations using such commercially available reagents are routine in the art. Macrophages were obtained through the ex vivo maturation of negatively-selected monocytes for seven days. Each isolated cell population was analyzed by fluorescence activated cell sorting (FACS) to determine whether the isolated cell population was expressing the expected cell surface proteins. RNA was isolated and assessed by Affymetrix array (Affymetrix GENECHIP™ HG-U1333 Plus 2.0). Data normalization and analysis for human BTNL3 transcript detection was performed using ROSETTA RESOLVER® software (Rosetta Biosoftware, Cambridge, Mass., USA).

The results of these analyses are shown in FIG. 2. The cells type tested included peripheral blood mononuclear cells, T cells, CD4+ T cells, CD8+ Tcells, B cells, monocytes, macrophages, neutrophils, eosinophils, and NK cells. Among cell types tested, neutrophils (lane 8 in FIG. 2) expressed the highest amounts of BTNL3.

Example 2

Preparation of Human BTNL3.Fc

The following describes how a fusion protein containing the extracellular region of human BTNL3, a linker, and the Fc portion of a human IgG1 antibody was made. A cDNA in an appropriate vector was constructed encoding the extracellular domain of human BTNL3, that is amino acids 1 to 236 of SEQ ID NO:2, fused to a linker plus a human IgG1 Fc fragment. SEQ ID NO:5 provides the sequence of this cDNA, and SEQ ID NO:6 provides the amino acid sequence of the BTNL3.Fc protein encoded by this cDNA, including the signal sequence. The mature BTNL3.Fc protein sequence, that is, lacking the signal sequence, is provided in SEQ ID NO:7. Cos PKB cells were transfected with the BTNL3.Fc mammalian expression construct using LIPO- FECTAMINE™ 2000 (Invitrogen) and cultured in complete Dulbecco's Modified Eagle Medium (DMEM) with 0.5% Low Ig Serum. These methods are described in detail by Ettehadieh et al., OVEREXPRESSION OF PROTEIN KINASE Bα ENHANCES RECOMBINANT PROTEIN EXPRESSION IN TRANSIENT SYSTEMS in Animal Cell Technology: From Target to Market: Proceedings of the 17th ESACT Meeting, Tylösand, Sweden, Jun. 10-14, 2001, Vol. 1, Lindner-Olsson et al., eds., pp. 31-35, Springer, 2001. The portions of this reference describing how to make a recombinant protein are incorporated herein by reference. Seven days post transfection, supernatants were harvested, and the BTNL3.Fc protein was purified by Protein A column chromatography (MABSELECT™ SuRe column, GE Healthcare).

The size of the resulting protein was determined by gel electrophoresis and size exclusion chromatography (SEC). It was expected that the protein would be dimeric because of the presence of the Fc region, which causes dimerization due to noncovalent interactions between $C_H3$ regions and disulfide bonds formed between hinge regions. If the protein were a dimer, its expected molecular weight would likely be in excess of about 120 kD due to variable glycosylation. Similarly, its expected molecular weight under reducing conditions, in which it would be expected to be monomeric, would be at least about 60 kD. On a reducing gel, a number of bands were observed, most of which were between about 50 and 64 kD. The observed molecular weight of the main peak by SEC under non-reducing conditions was about 140 kD, although both higher and lower molecular weight species were also observed. These data indicate that the protein is at least dimeric under non-reducing conditions and that it likely also forms higher order multimers.

Example 3

Expression of BTNL3 in Human Normal and Tumor Tissue

Figure 3:
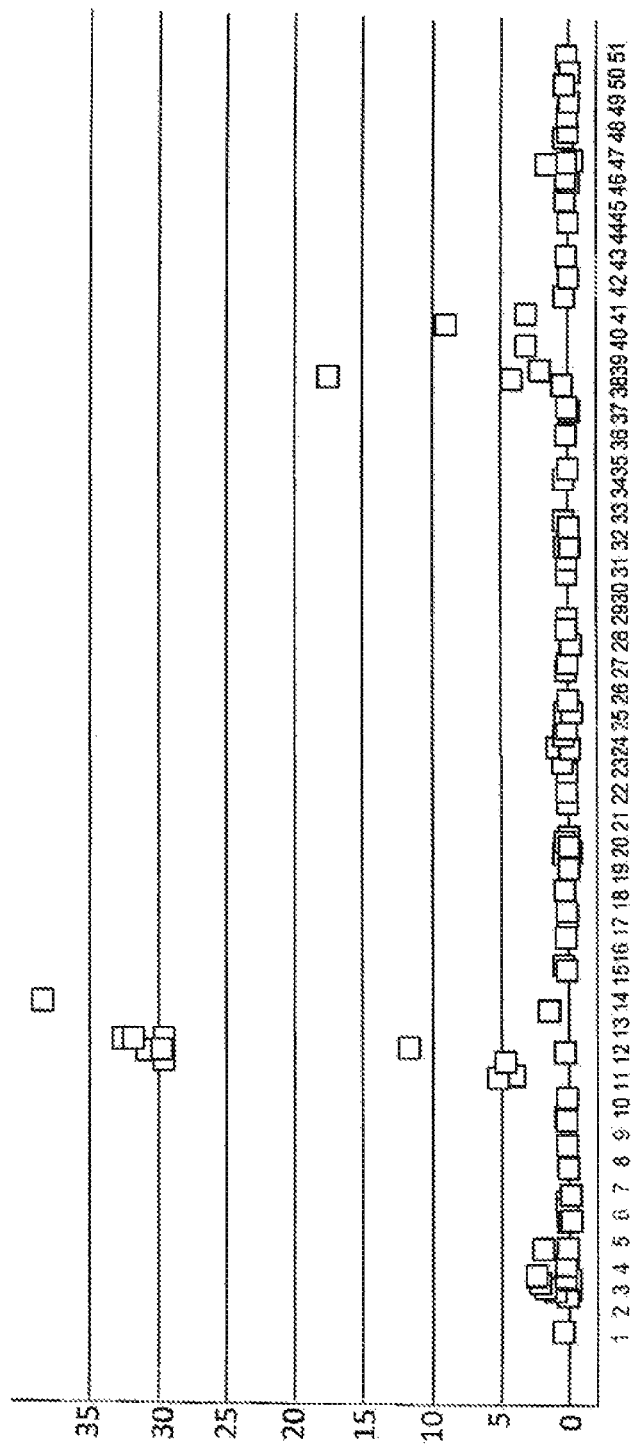
FIG. 3: This figure shows the amount of expression of BTNL3 as measured by next generation RNA sequencing of RNA extracted from normal human tissues identified on the X axis as follows: 1, adrenal, not otherwise specified; 2, artery, aorta; 3, blood; 4, bone marrow, not otherwise specified; 5, brain, anterior cingulate; 6, brain, cerebellum; 7, brain, frontal cortex; 8, brain, not otherwise specified; 9, breast; 10, bronchus; 11, ascending colon; 12, colon, not otherwise specified; 13, sigmoid colon; 14, duodenum; 15, esophagus; 16, abdominal fat; 17, heart, not otherwise specified; 18, heart, ventricle; 19, heart, left ventricle; 20, islet cell; 21, kidney, cortex; 22, kidney, medulla; 23, kidney, not otherwise specified; 24, liver; 25, lung; 26, mesenteric lymph node; 27, lymph node, not otherwise specified; 28, skeletal muscle, not otherwise specified; 29, optic nerve; 30, ovary; 31, head of pancreas; 32, pancreas, not otherwise specified; 33, peripheral blood mononuclear cells; 34, prostate; 35, rectum; 36, retina; 37, skin, not otherwise specified; 38, small intestine, duodenum; 39, small intestine, ileum; 40, small intestine, jejunum; 41, spinal cord, cervical; 42, spinal cord, lumbar; 43, spinal cord, thoracic; 44, spleen; 45, stomach, body; 46, stomach, not otherwise specified; 47, stomach, pylorus; 48, testis; 49, thyroid gland; 50, tongue; and 51, urinary bladder, detrusor muscle. The y axis indicates the amount of expression, shown as the number of BTNL3 transcripts per cell.

To determine the level of expression of BTNL3 at the RNA level in human normal and tumor tissue, RNA was isolated and assessed by next-generation sequencing analysis. In particular, the TruSeq® (Illumina, Inc., San Diego, Calif.) reagents were used to prepare samples and reactions that were processed in a HiSeq® 2000 (Illumina, Inc., San Diego, Calif.) sequencing system. Data was analyzed to quantify the number of BTNL3 RNAs per cell. The results of this analysis for normal human tissues are shown in FIG. 3. Little or no BTNL3 expression was detected in most tissues, but higher levels of expression were detected in samples from colon and small intestine. Thus, BTNL3, like BTNL2, is expressed primarily in the gut.

Similar methods were used to determine levels of BTNL3 RNA expression in various human tumor tissue samples. These results are shown in FIG. 4. Moderate levels of BTNL3 expression were detected in several different adenocarcinoma samples, but not in all tumor tissues. In addition, moderate and high levels of BTNL3 expression were detected in some samples from type II diabetes patients, suggesting that BTNL3 could play a role in mediating or responding to this disease in some cases.

Example 4

In Vitro Analysis of Murine CD4+ T Cell Proliferation

The following experiment was done to determine the effects of a human BTNL3:Fc fusion protein on the proliferation of mouse CD4+ T cells in vitro.

A single cell splenocyte suspension, which was prepared from spleens harvested from at least five female C57BL/6 mice per experiment, was used to purify CD4+T cells with the mouse EASYSEP™ CD4+negative selection kit (Stem Cell Sciences). Purity of CD4+T cells was greater than 90% as assessed by FACS analysis. Tissue culture-treated microtiter plates were coated with variable concentrations of an anti-mouse CD3 monoclonal antibody (Clone 2C11, BD Biosciences Pharmingen, San Diego, Calif., USA) and the Fc fusion protein indicated in the brief description of FIG. 5. Each well was equalized for total protein content using human IgG (Sigma). All coatings/dilutions were done in PBS. Plates were incubated overnight. Wells were then washed with PBS, and then $1-2\times10^5$ purified CD4+ splenocytes/well were added. Proliferation of the CD4+ T cells was determined by incorporation of ³H-thymidine (1 μCi/well) during the last 6 hours of the 72 hour culture. Human IgG was used as a negative control. As positive controls, mouse BTNL2.Fc, which had been previously shown to inhibit proliferation of T cells, and human B7-2-Fc (R & D Biosystems), a known positive costimulator of T cells, were also included.

The results are shown in FIG. 5. Lane 1 in FIG. 5 represents a negative control assay containing no immobilized protein and no additional protein. Lanes 2 and 3 show results from positive control assays containing immobilized anti-mouse CD3 antibody plus either human IgG (lane 2) or a human B7-2-Fc protein. Lane 4 shows results from an assay containing immobilized anti-mouse CD3 antibody plus mouse BTNL2.Fc, a negative costimulatory molecule. Lane 5 shows results of an assay containing immobilized anti-mouse CD3 antibody plus human BTNL3.Fc. Lanes 6 and 7 show results from an assay using immobilized human IgG plus either mouse BTNL2.Fc (lane 6) or human BTNL3.Fc (lane 7). These data confirm the stimulatory effect of human B7-2-Fc and the inhibitory effect of mouse BTNL2.Fc on mouse T cell proliferation and indicate that human BTNL3.Fc can inhibit mouse T cell proliferation. These data suggest that a human BTNL3.Fc fusion protein can have effects on murine T cells similar to those observed using a murine BNTL2.Fc fusion protein. Furthermore, these data suggest that human BTNL3 can interact with a receptor on murine T cells, despite the fact that a close murine homolog of human BTNL3 has not been isolated Example 5

Effects of BTNL3.Fc on Gene Expression of Mouse CD4+ T Cells

In a standard anti-CD3 proliferation assay, mouse CD4+T cells were isolated as described above and stimulated with an immobilized anti-CD3 antibody plus no additional protein, immobilized mouse BTNL2.Fc, or immobilized human BTNL3.Fc. Proliferation was measured by ³H-thymidine incorporation. After 24 hours of stimulation, RNA was isolated from the cells and analyzed by Affymetrix cDNA chips to determine levels of expression of a large variety of sequences. Results are shown in FIG. 6 and Table 4 below. Stimulation of murine CD4+ cells with an immobilized anti-CD3 antibody upregulated the expression many immunoregulatory and inflammatory genes as expected. Inclusion of murine BTNL2.Fc or human BTNL3.Fc dampened this response.

In FIG. 6, a black dot represents the relative amount of expression of a particular sequence observed in stimulated as compared to unstimulated cells. Sequences with no significant difference in expression between stimulated and un-stimulated cells are not represented in FIG. 6. In FIG. 6, the left panel shows data from cells stimulated with an anti-CD3 antibody alone, the middle panel shows data from cells stimulated with an anti-CD3 antibody plus a murine BTNL2.Fc fusion protein, and the right panel shows data from cells stimulated with an anti-CD3 antibody plus a human BTNL3.Fc fusion protein. These data show that the expression of many genes is significantly up- or down-regulated by 24 hours of stimulation with anti-CD3 antibody. However, addition of either murine BTNL2.Fc or human BTNL3.Fc substantially reduces this number of genes. These data confirm that BTNL2.Fc is a negative costimulator and indicate that BTNL3.Fc is also a negative costimulator. Thus, these results indicate that both molecules inhibit the activation of murine $CD4^+$ T cells by anti-CD3 antibody.

Table 4 below provides additional numeric data from this experiment. Out of 45,060 sequences assayed, expression of many (26,530) sequences was not changed in a statistically significant manner by stimulation with an anti-CD3 antibody alone. However, expression of 8,631 and 9,899 sequences was significantly up- or down-regulated, respectively, upon stimulation with anti-CD3 antibody alone. These numbers were substantially decreased when either murine BTNL2.Fc or human BTNL3.Fc was added. Hence, both BTNL2 and BTNL3 inhibit the activation of T cells.

TABLE 4

Effects of BTNL3 on the Gene Expression Signature of anti-CD3 Antibody

| | | # Data Points | | |
|---|---|---|---|---|
| Growth Conditions | Unchanged | Up-Regulated ($p \leq 0.01$) | Down-Regulated ($p \leq 0.01$) | Total # Data Points |
| Anti-CD3 24 h/No Stim 24 h | 26,530 | 8,631 | 9,899 | 45,060 |
| Anti-CD3 + rBTNL2 Fc 24 h/No Stim 24 h | 40,752 | 2,056 | 2,252 | 45,060 |
| Anti-CD3 + rBTNL3 Fc 24 h/No Stim 24 h | 39,161 | 2,831 | 3,068 | 45,060 |

What is claimed is:

1. A in vivo method of inhibiting T cell proliferation comprising administering a BTNL3 protein comprising
   (a) the amino acid sequence of amino acids 18-236 of SEQ ID NO:2 or the amino acid sequence of amino acids 18-166 of SEQ ID NO:9,
   (b) an amino acid sequence at least 90% identical to amino acids 18-236 of SEQ ID NO:2 or amino acids 18-166 of SEQ ID NO:9, wherein the alignment window of the amino acid sequence with amino acids 18-236 of SEQ ID NO:2 or amino acids 18-166 of SEQ ID NO:9 is at least 80 amino acids long, or
   (c) an amino acid sequence that has no more than 20 insertions, deletions, or substitutions of a single amino acid relative to the sequence of amino acids 18-236 of SEQ ID NO:2 or amino acids 18-166 of SEQ ID NO:9,
   wherein the BTNL3 protein retains the ability to attenuate T cell proliferation as measured by the proliferation of mouse T cells stimulated by an immobilized anti-CD3 antibody.

* * * * *